United States Patent [19]

Fritzberg et al.

[11] Patent Number: 5,120,526
[45] Date of Patent: Jun. 9, 1992

[54] METHOD OF PRODUCING METAL RADIONUCLIDE LABELED PROTEINS FOR DIAGNOSIS AND THERAPY

[75] Inventors: Alan R. Fritzberg, Edmonds; Sudhakar Kasina; Ananthachari Srinivasan, both of Kirkland; Daniel S. Wilbur, Edmonds, all of Wash.

[73] Assignee: NeoRx Corporation, Seattle, Wash.

[21] Appl. No.: 650,834

[22] Filed: Feb. 4, 1991

Related U.S. Application Data

[60] Division of Ser. No. 423,180, Oct. 18, 1989, which is a division of Ser. No. 065,011, Jun. 19, 1987, Pat. No. 4,897,255, which is a continuation-in-part of Ser. No. 817,321, Jan. 9, 1986, abandoned, which is a continuation-in-part of Ser. No. 692,000, Jan. 14, 1985, abandoned.

[51] Int. Cl.⁵ .................. A61K 49/02; A61K 39/395
[52] U.S. Cl. .................. 424/1.1; 530/391.5; 530/404; 530/405; 530/388.85; 530/866; 424/9
[58] Field of Search .............. 424/1.1; 530/390, 391, 530/404, 405

[56] References Cited

U.S. PATENT DOCUMENTS 4,673,562 6/1987 Davison et al. .............. 424/1.1

OTHER PUBLICATIONS

Fritzberg et al., "Labeling of Proteins by Chelate Conjugation", *Amer. Chem. Soc. Abstracts*, Apr. 84, Abstract No. 70.

*Primary Examiner*—John S. Maples

[57] ABSTRACT

Protein conjugated chelated metal radionuclides are provided for use in vivo. Intermediates are provided for preparing the polypeptide compositions efficiently.

20 Claims, 12 Drawing Sheets

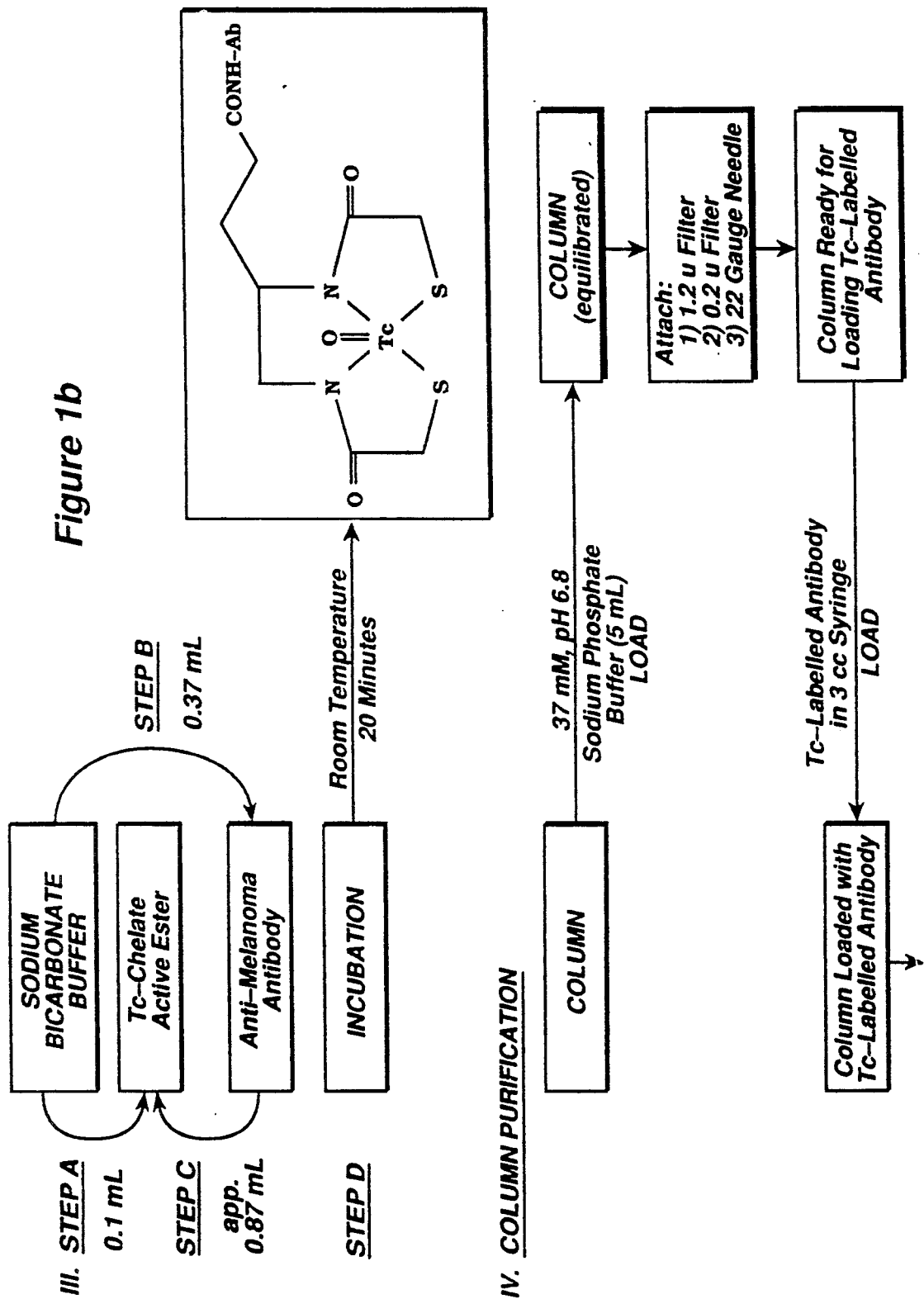

METHOD A

I. Stannous Citrate Vial, lyophilized, (Citric Acid = 75 mg. Stannous Chloride = 750 ug. Gentisic Acid = 250 ug. Lactose = 100 mg.) →  $ReO_4^-$ 1st 3.0 mL of the GENERATOR, Room Temperature, 10 Minutes → Re–CITRATE

II. STEP A

- 0.5 mL ISOPROPYL ALCOHOL
- CHELATING COMPOUND, 500 ug.
- 0.3 mL Re–CITRATE

→ 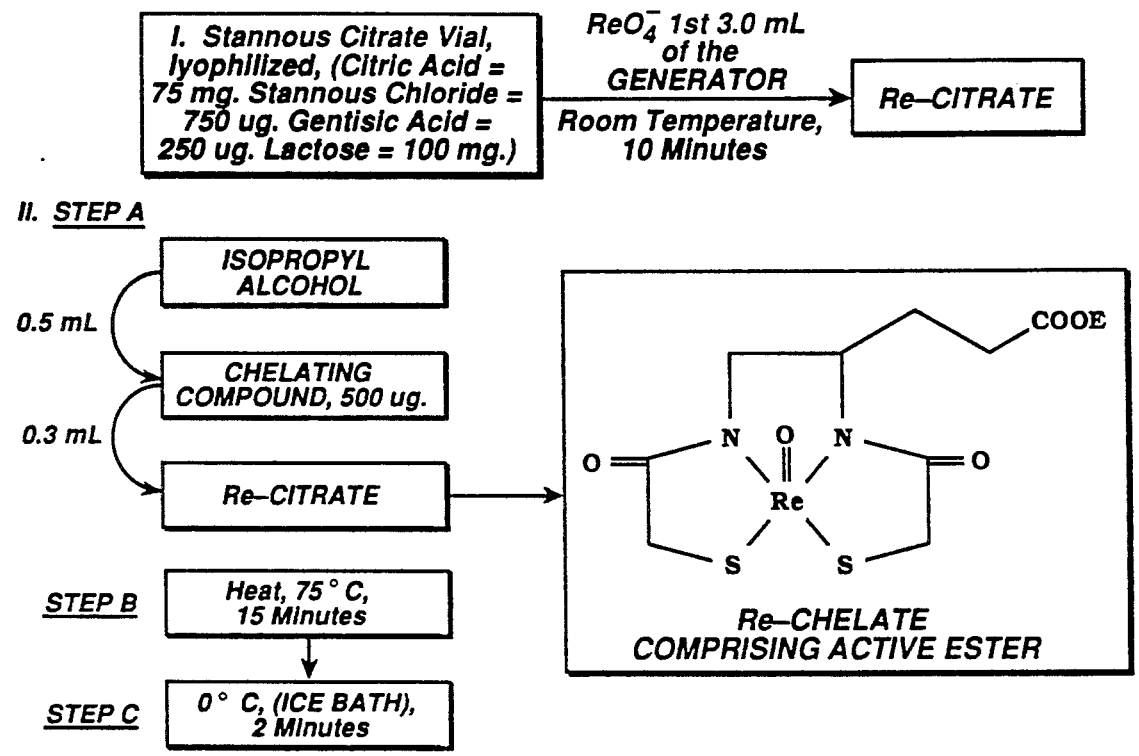

Re–CHELATE COMPRISING ACTIVE ESTER

STEP B — Heat, 75° C, 15 Minutes

STEP C — 0° C, (ICE BATH), 2 Minutes

III. C-18 BAKER PURIFICATION OF Re–CHELATE ACTIVE ESTER

STEP A — Column Conditioning:
1) 2 mL EtOH
2) 2 mL Water

STEP B — Sample Loading

STEP C — Washes:
1) 3x2 mL Water
2) 3x2 mL 20% EtOH – 0.01 M Phosphate Buffer

STEP D — Column Drying

STEP E — Elution:
1) 2x1 mL Acetonitrile

STEP F — $N_2$ flow to dry Acetonitrile

*Figure 2a*

IV. CONJUGATION WITH ANTIBODY

1) ANTIBODY, [Ab] during conjugation = 2.5 mg/mL
2) 0.5 M Carbonate/Bicarbonate Buffer, pH 9.50

ADD Re – CHELATE ACTIVE ESTER
    Incubate at Room Temperature, 15 minutes
3) L-Lysine, 25 mg. (250 mg/mL 0.5 M $CO_3^=$/$HCO_3^-$)., R.T., 15'
4) SEPHADEX G-25 Column PURIFICATION.

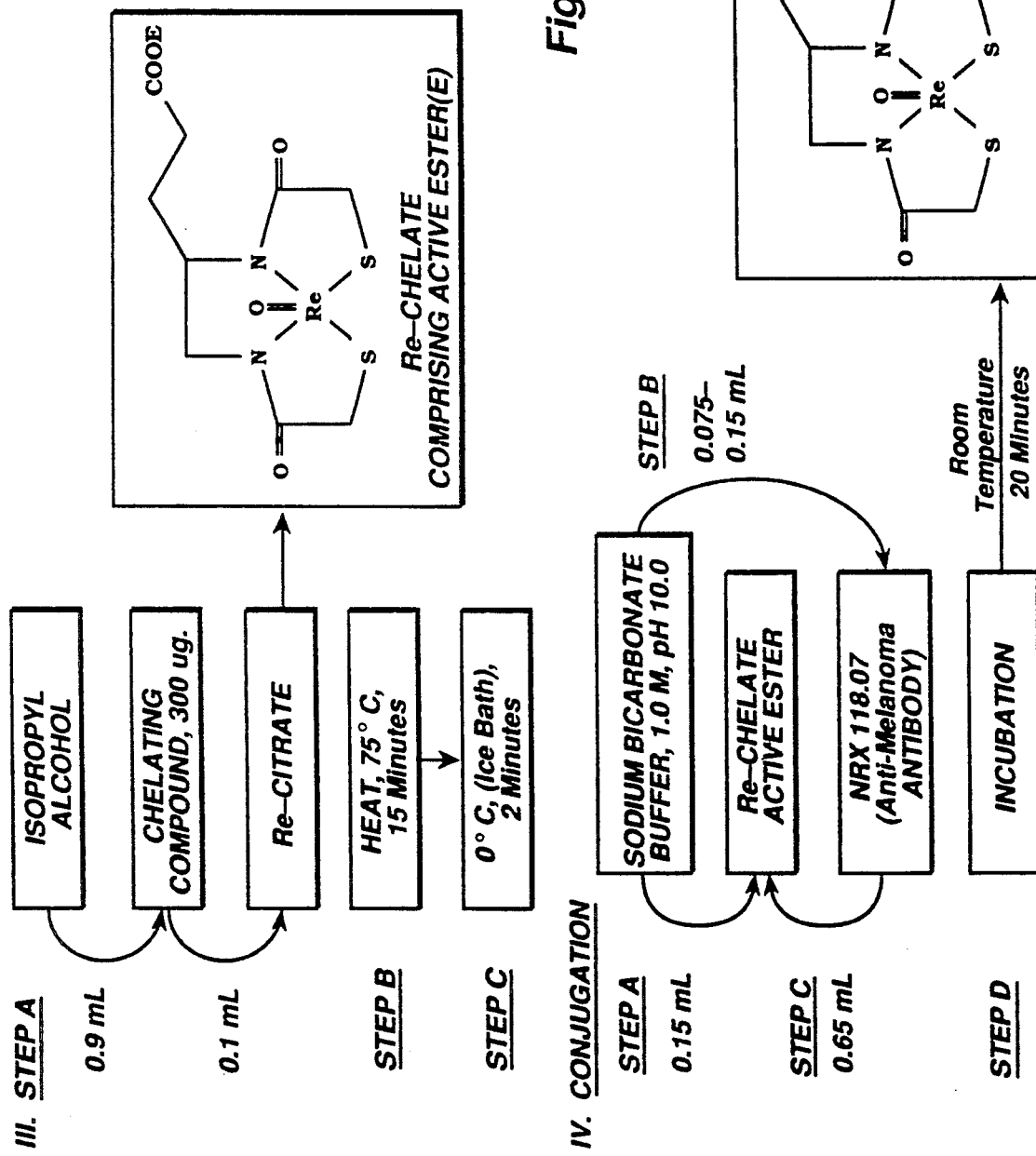

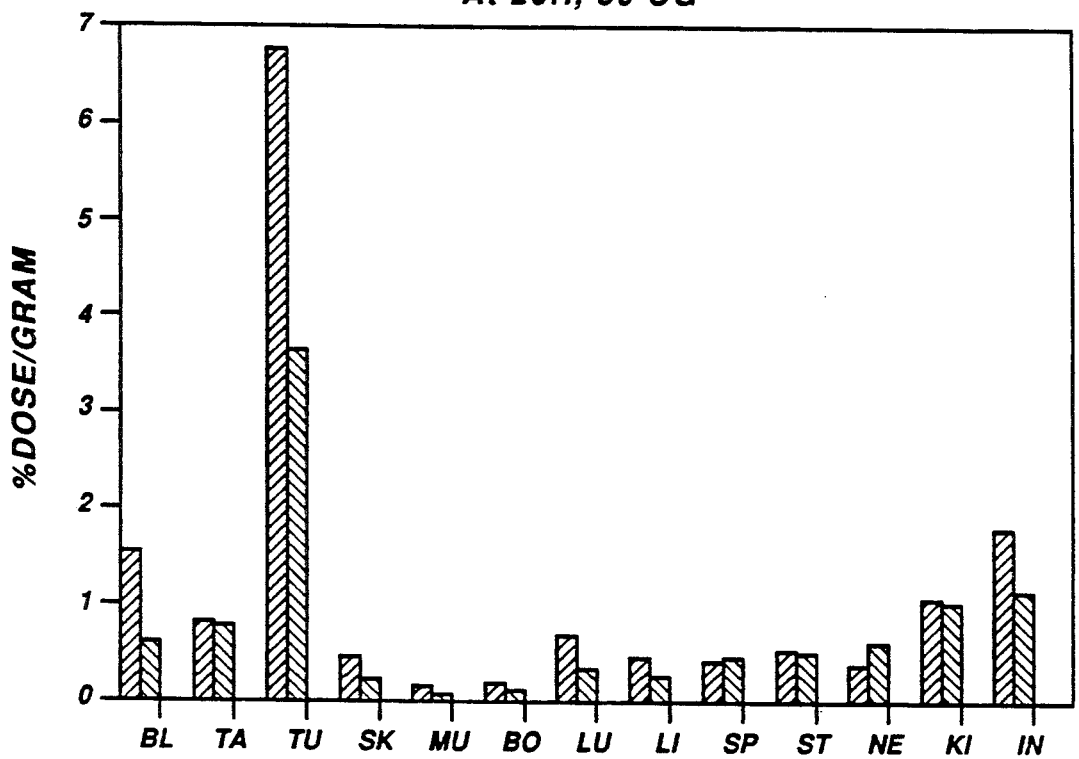
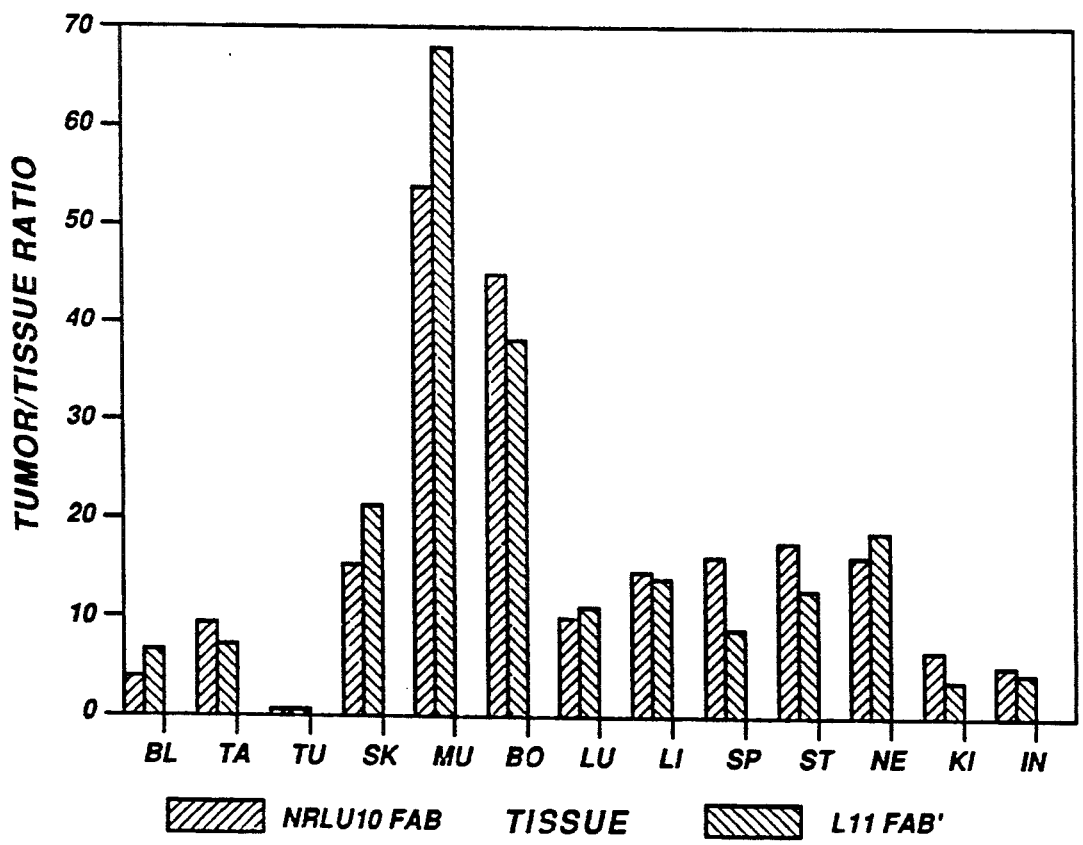

METHOD OF PRODUCING METAL RADIONUCLIDE LABELED PROTEINS FOR DIAGNOSIS AND THERAPY

CROSS-REFERENCE TO RELATED APPLICATIONS

This application is a divisional of prior application Ser. No. 07/423,180, filed Oct. 18, 1989, which is a divisional of prior application Ser. No. 07/065,011, filed June 19, 1987 and now issued as U.S. Pat. No. 4,897,255, which is a continuation-in-part of application Ser. No. 817,321, filed Jan. 9, 1986 now abandoned, which is a continuation-in-part of application Ser. No. 692,000, filed Jan. 14, 1985, now abandoned

BACKGROUND OF THE INVENTION

1. Field of the Invention

Radiolabeled compounds are important tools in medical diagnosis and treatment. Such compounds are employed in a variety of techniques including the diagnosis of deep venous thrombi, the study of lymph node pathology, and the detection, staging and treatment of neoplasms. A number of these compounds employ metal radionuclides such as Technetium-99m. When employing radionuclides for in vivo administration it is desirable that the radionuclide localize in a target organ or cancer site. Therefore, radionuclides are usually formulated to provide preferential binding to or absorption by the particular organ or tissue. There is considerable interest in being able to accurately direct a radionuclide to a preselected site to reduce background radiation directed to surrounding or distant tissue, reduce the dosage, minimize background for in vivo imaging and minimize undesirable side effects. Toward this end, methods involving specific ligands or receptors to which the radionuclide may be conjugated are of interest.

Publications of interest include Khaw, et al., *J. Nucl. Med.* (1982) 23:1011; Rhodes, B. A., *Sem. Nucl. Med.* (1974) 4:281; Davidson, et al., *Inorg. Chem.* (1981) 20:1629; and Byrne and Tolman, *J. Nucl. Med.* (1983) 24:126. See particularly Fritzberg, et al., *J. Nucl. Med.* (1982) 23:592; Fritzberg, et al., ibid. (1981) 22:258; and Fritzberg, et al., ibid. (1982) 23:17 for descriptions of mercaptoacetyl derivatives of ethylene diamine carboxylic acid derivatives. See also U.S. Pat. Nos. 4,434,151, 4,444,690, and 4,472,509 whose disclosures are incorporated herein by reference.

SUMMARY OF THE INVENTION

Metal radionuclide labeled proteins are provided for the diagnosis and treatment of a variety of pathologic conditions. Specifically, chelated radionuclide protein conjugates are employed for the diagnosis of conditions including lymph node pathology and deep venous thrombi and the detection and staging of neoplasms. Also, chelated radionuclides as protein conjugates are employed for radiotherapy of tumors.

DETAILED DESCRIPTION OF THE INVENTION

Figure 1A:
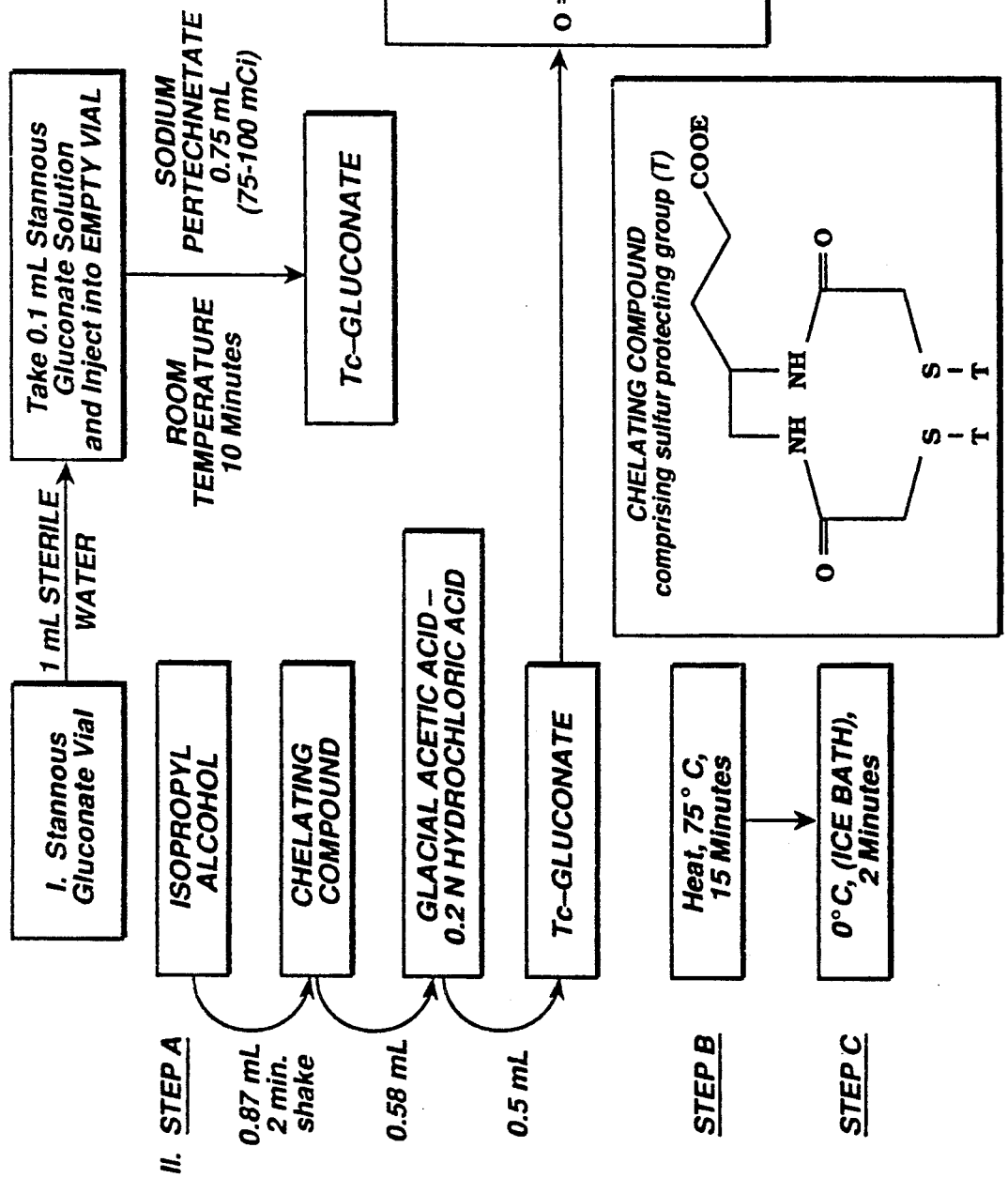
FIG. 1 (a-c) is a flow chart representing the preparation of a $^{99m}$Tc-radiolabeled polypeptide using a kit in accordance with one embodiment of the invention.

Improved methods and compositions are provided related to metal radionuclide chelates, their active esters for conjugating to proteins, and the resulting peptide conjugates, as well as the use of the conjugates in radioimaging and radiotherapy.

The metal chelating compounds will be dithio, diamino-or diamidocarboxylic acids or amines or derivatives thereof, e.g., a N,N'-bis-mercaptoacetyl ,(w-x)-diamino carboxylic acid, (x is 1 or 2), esters capable of forming an amide bond in an aqueous medium with a polypeptide, and intermediates to the chelate. The chelating compounds are referred to as $N_2S_2$ ligands or chelates.

The compounds of this invention will for the most part have the following formula:

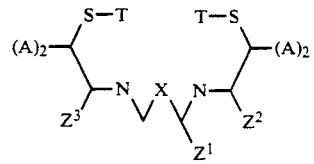

wherein:

one of $Z^1$, $Z^2$, $Z^3$ or $Z^4$ is RCW-(HNV)$_n$Y, and the others are $=$O or H$_2$;

R is a divalent organic radical of at least 1 carbon atom and typically not more than about 10, usually not more than 6 carbon atoms, usually from 1 to 3 carbon atoms having from 0 to 2 heteroatoms which are chalcogen (O, S) or nitrogen and is aliphatic, alicyclic, aromatic or heterocyclic, preferably aliphatic having from 0 to 2, usually 0 to 1 site of aliphatic unsaturation (e.g., ethylenic) and of from 1 to 2 carbon atoms;

W is oxygen or imino ($=$O or $=$NH), with the proviso that when Y is —NH$_2$ or —NHNH$_2$, the W bonded to the carbon atom bonded to Y is H$_2$;

V is RCW, where the two RCWs may be the same or different, usually being of from 1 to 8, more usually of from 1 to 6 carbon atoms, preferably of from 2 to 3 carbon atoms;

n is 0 or 1;

T is an acyl or acylthio radical of from 2 to 10, usually 2-8 carbon atoms, either a hydrocarbyl acyl or substituted acylradical, usually aryl e.g., phenyl) or alkyl (e.g., methyl), an organic sulfhydryl radical of from 1 to 10 carbon atoms, either substituted or unsubstituted hydrocarbyl; a heterocycle, particularly a chalcogen (0, S) heterocycle; an acylamidomethylene, where the acyl group is as defined above; hydrogen; sulfonato; an alkali metal ion; or the two T's may be taken together to define a polyvalent metal radionuclide, as the metal ion or metal ion oxide;

Substituents include nitro, cyano, inert halo (aryl or polyhalo), non-oxo-carbonyl (carboxylic acid, amide and ester), and the like;

Y is hydroxyl, an oxy salt, particularly an alkali metal salt (e.g., lithium, sodium and potassium), an organic oxy compound forming an ester, usually lower alkoxy of from 1 to 6 carbon atoms or a group which permits amide formation in an aqueous medium, particularly with a polypeptide, —NH$_2$, —NHNH$_2$, or a polypeptide of at least two amino acids which may be 2 MDal (megadalton) or more. With polypeptides, particularly polypeptides over 1 KDal (kilodalton)., there may be more than one chelating compound bound to the polypeptide, usually not more than about one per 0.5 KDal;

A's are the same or different and are hydrogen or lower alkyl of from 1 to 6 carbon atoms, usually of from 1 to 3 carbon atoms, particularly methyl, usually hydrogen; and X is a bond, methylene or CHZ$^4$;

where T is other than M or H, Y will be other than a polypeptide.

The link between CW and the polypeptide will vary depending upon the nature of CW—Y. Where CW—Y includes a bond formed by reaction with a free amine group on the polypeptide Y, the linkage will be either a carboxamide or amidine depending on whether W is =O or =NH. If, however, CW-Y defines a methyleneamine or methylenehydrazine, then reductive amination may be required with a sugar-substituted-polypeptide which has been cleaved to the oxo group (e.g., glycol cleavage with periodate). Reductive amination may be achieved by combining the oxo-substituted polypeptide with the amino- or hydrazino-substituted N$_2$S$_2$ ligand in the presence of a reducing agent, such as sodium cyanoborohydride.

A preferred group of compounds will have one of the following formulas:

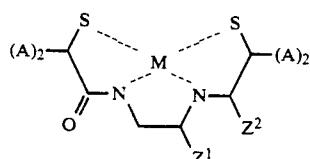

or

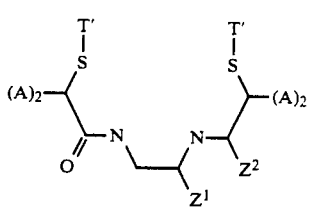

wherein all of the symbols have been defined previously except for M and T', and wherein:

M is a radionuclide capable of being chelated as the metal ion or metal ion oxide; and T' is a sulfur protective group, which includes acyl, acylthio, hydrocarbylthio or substituted-hydrocarbylthio or heterocyclicthio, where the acyl and hydrocarbyl groups may be aliphatic, alicyclic, aromatic or combinations thereof and the acyl group further includes heterocyclic, wherein acyl is normally carboxyacyl; T' will generally be of from 2 to 10 carbon atoms, usually 2 to 8 carbon atoms when acyl, where substituents will include non-oxo-carbonyl (carboxy), halo (aryl), particularly fluoro and chloro, cyano and nitro.

In one embodiment of the invention, in accordance with this preferred group of compounds, one of Z$_1$ or Z$_2$ is RCW—(HNV)$_n$Y, and the other is=O or H$_2$; wherein R is the divalent radical —(CH$_2$)$_2$—, W is oxygen (=O), n is 0 and Y is the leaving group of an ester. The other symbols are as previously defined. Thus, these preferred compounds comprise aliphatic esters of five carbon atoms, and RCW—(HNV)$_n$Y may be represented as

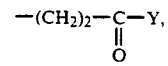

where the other two carbons which are part of the 5-carbon c comprising the ester group are in the formulae presented above. The carbon atom which is β to the carboxyl carbon in the chain may be substituted with groups other than hydrogen, as long as the reactivity of the ester toward a protein is not diminished through steric hindrance. Permissible substituents on this carbon atom include, for example, oxygen (=O) and straight-chain lower alkyl groups (e.g., methyl and ethyl groups . The chain length of five carbons is preferred because it has been found to be long enough to minimize steric hindrance of the reaction of the ester with a polypeptide, yet short enough so that the chelate compound retains the desirable water solubility (described above). Thus, these preferred compounds generally are more reactive toward polypeptides than are compounds having one or more carbons deleted from the chain, due to the increasing steric hindrance that accompanies decreasing chain length. Water solubility has been found to decrease as carbons are added to the chain. Increasing chain length also increases hepatobiliary excretion of the carboxylate form of the metal complex. Thus, metabolic release of the complex with longer side chains increases the likelihood of undesirable localization in the liver and subsequently the lower abdomen (gut). These preferred compounds of 5-carbon chain length may be referred to as C$_5$N$_2$S$_2$ chelating compounds or chelate compounds.

A group of chelate compounds according to this invention will for the most part have the following formula:

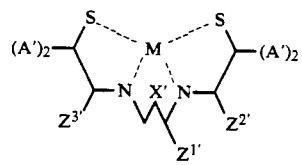

wherein:

one of Z$^{1'}$, Z$^{2'}$, Z$^{3'}$or Z$^{4'}$ is R'CW'(HNV')$_{n'}$Y', and the others are=O or H$_2$;

(A')'s are the same or different and are hydrogen or lower alkyl of from 1 to 6, usually 1 to 3 carbon atoms, particularly methyl, usually hydrogen;

n' is 0 or 1;

V' is R'CW', where the (R'CW')'s may be the same or different, usually being of from 1 to 8, more usually of from 1 to 6 carbon atoms, preferably of from 2 to 3 carbon atoms;

W' is oxygen or imino (=N or =O), with the proviso that when Y' is =NH$_2$ or NHNH$_2$, the W' bonded to the carbon atom bonded to Y is H$_2$;

M is a radionuclide capable of being chelated as the metal ion or metal ion oxide;

X' is a bond, methylene or CHZ$^4$;

R' is an aliphatic divalent radical of from 1 to 6, usually from 1 to 3 carbon atoms, having from 0 to 1 site of aliphatic unsaturation and 0 to 2 heteroatoms, usually straight chain and preferably methylene or polymethylene of from 2 to 3 carbon atoms; and Y' is hydroxyl, an oxy salt, particularly an alkali metal salt, such as sodium, an ester of an hydroxylic compound, where the ester is capable of forming an amide bond with a polypeptide in an aqueous medium without denaturation of the polypeptide; —NH$_2$; —NHNH$_2$; an amino acid, or a polypeptide usually of at least about 1000 molecular weight, more usually at least about 2000 molecular weight, generally less than about 1.6 MDal, more usually less than about 800 KDal. Of particular interest are immunoglobulins or specific binding fragments thereof.

The dashed lines in the formulae presented for the chelate compounds of the invention represent four coordinate covalent bonds between the metal radionuclide M and each of the two sulfur and the two nitrogen atoms shown in the formulae. Thus, the metal radionuclide is bound through relatively stable bonds in the chelate compounds of the invention.

A variety of metals may be employed as the radionuclide. These metals include copper (e.g., $^{67}$Cu and $^{64}$Cu); technetium (e.g., $^{99m}$Tc); rhenium (e.g., $^{186}$Re and $^{188}$Re); lead (e.g., $^{212}$Pb); bismuth (e.g., $^{212}$Bi); and palladium (e.g., $^{109}$Pd). Methods for preparing these isotopes are known. Molybdenum/technetium generators for producing $^{99m}$Tc are commercially available. Procedures for producing $^{186}$Re include the procedures described by Deutsch et al, (*Nucl. Med. Biol.* Vol. 13:4:465–477, 1986) and Vanderheyden et al. (*Inorganic Chemistry*, Vol. 24:1666–1673, 1985), and methods for production of $^{188}$Re have been described by Blachot et al (*Intl. J. of Applied Radiation and Isotopes* Vol. 20:467–470, 1969) and by Klofutar et al (*J. of Radioanalytical Chem.*, Vol. 5:3–10, 1970). Production of $^{109}$Pd is described in Fawwaz et al., *J. Nucl. Med.* (1984), 25:796. Production of $^{212}$Pb and $^{212}$Bi is described in Gansow et al., *Amer. Chem. Soc. Symp. Ser.* (1984), 241:215–217, and Kozah et al., *Proc. Nat'l. Acad. Sci.* USA (January 1986) 83:474–478.

The esters are those esters which provide for the reaction with a polypeptide in aqueous medium. One or another of the esters may be preferred, depending upon the particular radionuclide, the protein and the conditions for conjugation. As used herein, the term "aqueous medium" is meant to include not only totally aqueous media but also mixed aqueous/organic media, wherein the organic component is present only in a relatively low concentration, i.e., a concentration low enough to minimize damage to (e.g., denaturation of) polypeptides in the aqueous medium. A variety of esters may be used, including aromatic esters containing electron-withdrawing groups, or α-substituted methyl esters (in which the substituents are electron withdrawing groups, such as, but not limited to, —CH$_2$CN,

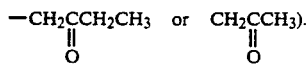

Preferred esters for use as Y or Y' groups in the present invention have several structural features which impart the desired stability and reactivity to the esters. For example, preferred esters should be relatively stable, especially with respect to hydrolysis in aqueous solutions. Chelating compounds comprising such esters may be added to aqueous reaction mixtures or mixed aqueous/organic reaction mixtures (i.e., for the radiolabeling and protein conjugation reactions) with relatively little hydrolysis of the ester group. Thus, such hydrolysis-resistant esters are particularly useful in reactions with proteins, since such reactions preferably are conducted under aqueous conditions to prevent denaturation of the proteins, which may occur in organic solvents. Advantageously, the ester is sufficiently stable to allow preparation of the chelating compound ahead of time and storage, even under humid conditions, until needed, with the ester group remaining substantially intact.

In addition, preferred esters are active esters. The term "active ester" is known to refer to esters which are highly reactive in nucleophilic substitution reactions. Preferred active esters for use in the present invention are highly reactive toward groups on polypeptides such that the ester-containing chelate compounds are bound to the polypeptides through the reaction. These active esters comprise leaving groups (i.e., the —OR' portion of an ester

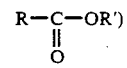

which are sufficiently electron-withdrawing to increase the susceptibility of the carbonyl

of the ester to attack by nucleophilic groups on the protein to form bonds. The kinetics of the reaction preferably are such that the ester reacts quickly with nucleophilic groups on the polypeptide to form bonds. Thus, the esters are free (i.e., unreacted) ester groups, potentially susceptible to hydrolysis (especially if the reaction is conducted at a basic pH), for only a short time. relatively high ratio of the desired aminolysis reaction to hydrolysis of the ester results.

Another consideration in choosing a suitable ester group is avoidance of esters which would have decreased reactivity toward the polypeptide due to steric hindrance. For example, increasing the size of the leaving group of the ester may cause steric hindrance of the reaction between the ester and the polypeptide.

The leaving group also should not render the chelating compound or chelate derived therefrom (i.e., after radiolabeling) insoluble in water. As described above, an important property of the chelating and chelate compounds of the invention is that they are sufficiently water soluble to allow the compounds to be reacted with proteins in aqueous or mixed organicaqueous solutions in which the organic solvent concentration is low enough to prevent damage to the protein (e.g., denaturation). Examples of leaving groups which may render the chelating compound relatively insoluble in water include large nonpolar groups such as long chain hydrocarbons.

Common esters which find use are the o- and p-nitrophenyl, 2-chloro-4-nitrophenyl, cyanomethyl, 2-mercaptopyridyl, hydroxybenztriazole, N-hydroxysuccinimide, trichlorophenyl, tetrafluorophenyl, 2- fluorophenyl, 4-fluorophenyl, 2,4-difluoro-phenyl, o-nitro-p-sulfophenyl, N-hydroxyphthalimide, N,N-diethylamino, N-hydroxypyrrolidone, tetrafluorothiophenyl, and the like. For the most part, the esters will be of activated phenols, particularly nitro-activated phenols and cyclic compounds based on hydroxylamine. As other hydroxylic compounds become available, these also may find use in this invention.

Especially good results have been achieved by using a 2,3,5,6-tetrafluorophenyl ester, which is an active ester having the above-described properties of stability and high reactivity. As shown in the examples below, chelate compounds of the present invention comprising the tetrafluorophenyl ester as the Y' group demonstrated relatively efficient amide bond formation when reacted with compounds (including antibodies) containing free amines. Good results also have been achieved by using a thiophenyl ester as demonstrated in Example 18 below.

The use of esters comprising nitro groups may be disadvantageous in certain circumstances. For example, the nitro group may be reduced by stannous ion which may be present when the stannous ion is added as a pertechnetate or perrhenate reducing agent, as described below.

The polypeptide compounds may be varied widely, depending upon the nature of the use of the radionuclide. Thus, the polypeptides may be, among others, receptors, hormones, lymphokines, growth factors, substrates, particularly compounds binding to surface membrane receptors, where the complex may remain bound to the surface or become endocytosed. Among receptors are surface membrane receptors, antibodies (including monoclonal antibodies) enzymes, naturally occurring receptors, lectins, and the like. Of particular interest are immunoglobulins or their equivalent, which may involve Fab fragments, Fab' fragments, F(ab')$_2$, F$_v$, T-cell receptors, etc.

Thus, "Y" may be a protein, a polypeptide or a fragment thereof. As used herein, the term "polypeptide" includes polypeptides, proteins, or fragments thereof. These proteins and polypeptides may be modified as long as the biological activity necessary for the intended diagnostic or therapeutic application of the radiolabeled polypeptide is retained. For example, a modified antibody or fragment thereof may be used as long as binding to the desired antigen still occurs. The amino acid sequence of a protein may be varied (e.g., by known mutation techniques or deletion of portions thereof) as long as the desired biological activity (e.g., binding of the protein to specific target cells, tissues or organs) is retained. Methods of modifying proteins also may include, among others, attachment of bifunctional linker compounds which react with both a group on a protein and with the "Y" group on the chelating compounds, thereby binding the chelating compound to the protein through the linking compound. The polypeptide may be purified from a natural source or may be synthetic (e.g., produced by recombinant DNA technology or chemical synthesis procedures).

Polypeptides which bind to the desired target site are said to be "specific for" the target site. For example, antibodies which bind to a particular antigen are said to be specific for that antigen. It is to be understood that such polypeptides or antibodies are rarely 100% specific for a target site, and a certain degree of cross-reactivity with other tissues is common, as discussed more fully below. An example of a target site is a cancer site.

Many antigens associated with various types of cancer cells have been identified, and monoclonal antibodies specific for a number of these cancer cell-associated antigens also are known. Such antibodies are examples of the many polypeptides suitable for use as the "Y" or "Y'" component, which bind to a desired target site.

Proteins generally contain a variety of functional groups which may react with a Y or Y' group on the chelate compounds of the invention to bind the compounds to the protein. For example, when Y or Y' is the leaving group of an ester, the ester may react with hydroxy groups (e.g., on serine residues) or with sulfhydryl groups (e.g., on cysteine residues, although the resulting bond may not be very stable). However, the active ester groups are believed to react preferentially with free amino groups (generally those on lysine residues) in an aminolysis reaction. The resulting amide bond between the chelate compound and the protein is relatively strong, stable and essentially irreversible under the conditions which preserve the biological activity of the protein. Alternatively, when Y or Y' is an —NH$_2$ or —NHNH$_2$ group, an imine or hydrazine bond is formed between the chelating compound and the protein through reaction with oxo groups on the protein (e.g., oxo groups produced on glycoproteins as described above).

The $\omega,(\omega x)$-diamino aliphatic carboxylic acids, particularly alkanoic acids, generally will be of from 4 to 10, usually from 4 to 7 carbon atoms and are known compounds, or can be readily prepared in conventional ways or as described herein. For example, vicinal dibromides may be combined with aqueous ammonia under mild conditions. The amino groups may then be derivatized by reacting the hydrochloride salt of the diamino ester (e.g., lower alkyl ester) with an $\alpha$-haloacyl chloride (e.g., chloroacetyl chloride) in an inert hydrocarbon solvent (e.g., toluene), followed by substitution of the chloro groups with a mercapto group employing an appropriate derivative of hydrogen sulfide (e.g., sodium benzthiolate, sodium thioacetate, t-butyl mercaptan or the like). The ester may now be hydrolyzed to the acid and the metal chelate formed or the thioether reacted with an activated sulfonyl chloride followed by treatment with thioglycolate. Alternatively $\alpha$-alkylthio substituted acyl compounds may be used with carbodiimide for acylation, followed by cleavage of the thioether with formation of disulfide and reduction of the disulfide to mercapto, as described above.

An alternative approach, employed for the 4,5-diaminopentanoate, employs the readily available glutamate. After forming the 5-carboxy ester, the amino group is protected and the acid group (1-carboxyl) preferentially reduced to the alcohol. The alcohol is transformed into an-active cleaving group (e.g., halide or pseudohalide), followed by displacement with a nitrogen anion (e.g., azide), which serves as an intermediate to the amino group. After catalytic reduction of the amino intermediate to amino and hydrolysis of the ester, the amino groups are acylated with S-protected $\alpha$-mercaptoacyl groups. The protective groups may be removed, exchanged or otherwise modified (e.g., by introduction of water solubilizing groups).

Various synthetic procedures may be employed for preparing the different N$_2$S$_2$ chelate rings. Carboxamides may be formed and reduced using aluminum or borohydrides to form the amine. Amines may be alkylated with aliphatic halides. Ethylene or propylene diamines or carboxyalkylalkylene diamines may be used to link thioglycolic acids. Other synthetic procedures may also be employed depending on the $N_2S_2$ ligand of interest.

The imidate may be employed by preparing the nitrile of the amino protected w,(w-x)-diaminoalkyl halide or pseudohalide by displacement with nitrile, mercaptoacylation of the deprotected amino groups as described previously and imidoester formation by conventional techniques, e.g., acidic (HCl) anhydrous alkanol.

The S-protective groups may be varied widely, being acyl groups, thio groups or other compound which provides protection of the thio group during the subsequent manipulations and can be readily removed without deleterious effect on the peptide conjugate.

The sulfur-protective groups also serve to stabilize the chelating compounds by preventing reaction of the sulfurs with groups which are part of the chelating compound itself. For example, if protecting groups T or T' were replaced with hydrogens, the sulfurs may displace an active ester group (Y or Y') from the chelating compound.

Illustrative groups include benzoyl, acetyl, m- or p-phthaloyl, thioglycolic, o-carboxythiophenol, ethylthiocarbonate, α-mercaptopropionic, tetrahydropyranyl, sulfonato, etc. Alternatively cyclic di- or polysulfides may be formed. Disulfides may be prepared using sulfinyl halides, dinitrothiophenoxide substituted mercaptans, with mild oxidation in the presence of excess of the protective group, etc.

The protective groups may be removed in a variety of ways. Thioesters may be hydrolyzed using aqueous ammonia, sodium alkoxide in alkanol, or any conventional technique. Disulfides may be cleaved with dithiothreitol, glutathione, α-mercaptoethylamine or other conventional reagent. Cleavage of the disulfide may occur prior to or after conjugation to the polypeptide.

In a preferred embodiment of the invention, the sulfur-protecting groups T and T', when taken together with the two sulfur atoms to be protected, represent thioacetals or hemithioacetals. When such sulfur-protecting groups are used, radiolabeling of the chelating compound with technetium or rhenium may be accomplished efficiently under conditions of temperature and pH which leave the ester group on the chelating compound intact. The radiolabeling step may be accomplished in an exchange reaction under acidic pH conditions. When other types of protecting groups are employed, the radiolabeling step generally is conducted at a basic pH and/or relatively high temperatures. Such conditions may destroy the ester group. In addition, the reaction mechanisms may be other than an exchange reaction in other radiolabeling procedures.

The use of thioacetal or hemithioacetal S-protecting groups has the advantage of simplifying the preparation of the radiolabeled chelate compounds of the invention and the radio-labeled polypeptides prepared therefrom. For example, a separate step for removal of the sulfur-protecting groups is not necessary. The protecting groups are displaced from the compound during the radiolabeling in what is believed to be metal-assisted acid cleavage; i.e., the protective groups are displaced in the presence of the metal radioisotope at an acidic pH, and the radioisotope is bound by the chelating compound. In general, the hemithioacetal protective groups are somewhat more acid labile in the radiolabeling reaction than the thioacetal protective groups and, therefore, are generally preferred.

In addition, base-sensitive functional groups on the chelating compound survive the radiolabeling step intact. This is especially advantageous when Y or Y' is an ester group. When radiolabeling is conducted at basic pH (especially at a pH above about 9 or 10), such ester groups are substantially hydrolyzed and must be generated (or regenerated) after the radiolabeling step. Generation of the ester group generally involves a multistep procedure (e.g., by using a carbodiimide and a hydroxylic compound, as described below and in Example 3). These extra steps, and the need to remove carbodiimide and phenolic compounds (which may damage the protein when it is added) from the reaction mixture, are avoided when thioacetal and hemithioacetal protecting groups are used. Chelating compounds comprising esters thus are ready for conjugation to proteins immediately after radiolabeling without any esterification steps.

Thioacetals and hemithioacetals which may be used in the present invention include those groups which effectively maintain the sulfurs in a nonreactive state until the radio-labeling step, at which time the protective groups are displaced in the presence of the metallic radioisotope under acidic conditions When a thioacetal group is used, a single protecting group protects both sulfurs shown in the formula for the chelating compound. Thus, the two Ts in the formula are taken together to represent a group which, together with the sulfur atoms to be protected, defines a thioacetal group. Suitable thioacetals generally have the following formula in which the two sulfur atoms shown are the sulfur atoms of the chelating compound:

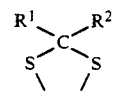

wherein $R^1$ and $R^2$ are the same or different and are selected from hydrogen; lower alkyl groups (preferably of from one to three carbon atoms, most preferably a methyl group); or an aromatic (phenyl) ring with an electron donating group (e.g., a methoxy, ethoxy, or hydroxy group, with methoxy being preferred) bonded directly to the ring, preferably in the para position. When either $R^1$ or $R^2$ comprises a phenyl ring, the other preferably is hydrogen so that the desired degree of water solubility is retained. Alkyl groups comprising longer carbon chains generally would decrease the water solubility of the chelating compound. Examples of suitable thioacetals include, but are not limited to, p-anisylidine:

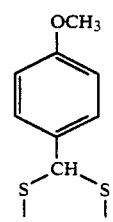

and acetonyl:

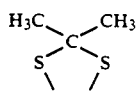

When hemithioacetal protective groups are used, each T or T', when taken together with a sulfur atom to be protected, defines a hemithioacetal group.

Suitable hemithioacetals include, but are not limited to, those having the following formulae, wherein the sulfur atom is a sulfur atom of the chelating compound, and a separate protecting group is attached to each of the two sulfur atoms on the chelating compound:

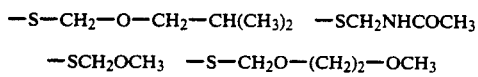

Preferred hemithioacetals generally are of the following formula, wherein the sulfur atom is a sulfur atom of the chelating compound and a separate protecting group (T or T') is attached to each of the two sulfur atoms on the chelating compound:

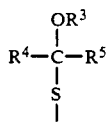

wherein $R^3$ is a lower alkyl group, preferably of from two to five carbon atoms, and $R^4$ is a lower alkyl group, preferably of from one to three carbon atoms. Alternatively, $R^3$ and $R^4$ may be taken together with the carbon atom and the oxygen atom shown in the formula to define a nonaromatic ring, preferably comprising from three to seven carbon atoms in addition to the carbon and oxygen atoms shown in the formula. $R^5$ represents hydrogen or a lower alkyl group wherein the alkyl group preferably is of from one to three carbon atoms. Examples of such preferred hemithioacetals include, but are not limited to:

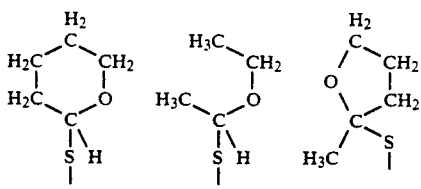

In general, the above-described thioacetals and hemithioacetals should not comprise long hydrocarbon chains. Such chains would diminish the desired water solubility of the chelating compounds of the invention and may decrease the ease of synthesis thereof.

Depending upon the particular metal, various conditions and techniques will be employed for preparing the metal chelate. To prepare the technetium chelate, the chelating compound as carboxylate or active ester may be combined with a pertechnetate solution in the presence of a reducing agent (e.g., stannous ion or dithionite under conventional conditions), whereby the technetium chelate is formed as a stable salt. The rhenium chelate may be formed by reducing perrhenate with stannous ion in the presence of citrate and the $N_2S_2$ ligand. Yields generally are 50% or greater after 1 hour at 50° C. Chelates of $^{212}Pb$, $^{212}Bi$ and $^{109}Pd$ may be prepared by combining the appropriate salt of the radionuclide with the chelating compound and incubating the reaction mixture at room temperature or at higher temperatures. It is not necessary to treat the lead, bismuth, palladium, and copper isotopes with a reducing agent prior to chelation, as such isotopes are already in an oxidation state suitable for chelation.

The chelating agent may be already esterified or esterified in accordance with conventional ways. If already esterified, a labile complex such as Tc-99m gluconate or glucoheptonate may be prepared which will allow exchange to the $N_2S_2$ active ester ligand, forming a complex suitable for protein conjugation. Alternatively, the carboxylic acid may be activated by employing a water soluble carbodiimide (e.g., EDCI) in an aqueous medium in the presence of at least a stoichiometric amount, preferably an excess, of the hydroxylic compound. A suitably buffered aqueous medium may be employed. Excess carbodiimide can be converted to urea by adding acetate. The aqueous medium may then be used directly without further purification for conjugation to the polypeptide. Desirably, the polypeptide will be added to the ester containing aqueous medium at a convenient concentration at a mildly alkaline pH, generally in excess of about 7.5 and less than about 9 and the reaction allowed to proceed for a sufficient time for virtually all of the active ester to either react with the polypeptide or be substantially completely hydrolyzed. Usually, the time will be less than about 6 hours and more than about 30 minutes, with temperatures ranging from about 0° to 50° C., usually not exceeding about 40° C. In general, the reaction time may be decreased when more highly active esters are used. For example, when a chelate comprising a tetrafluorophenyl ester is used, the reaction of the chelate with a protein may be substantially complete in 20 minutes, as described below (e.g., in Example 15). The particular conditions will be selected in accordance with the particular active ester, the pH, the activity of the polypeptide, and the like.

If desired, the number of free amino groups (i.e., those available for reaction with the chelate) on a particular polypeptide or fragment thereof may be estimated by known methods See, for example, Snyder and Sobocinski (Analytical Biochemistry, 64:284–288 [1975]) and Habeeb (Analytical Biochemistry, 14:328–336 [1966]). Basically, an assay using trinitrobenzene sulfonic acid (TNBS) with glycine as the standard may be performed. Either the standard or a sample of the polypeptide is dissolved in 0.1 M sodium borate, pH 9.2. TNBS is added to a final concentration of 0.75 mM, and the solution is allowed to stand for 30 minutes at room temperature. The absorbance at 420nm is then read. The assay is linear over the range $1 \times 10^{-8}$ to $2 \times 10^{-7}$ moles of free amine groups. The amount of antibody added to the conjugation reaction may be adjusted to give the desired stoichiometry (e.g., a 1:1 ratio of chelate to free amine groups).

It is also feasible but less preferable to conjugate the chelating agent ($N_2S_2$) to the polypeptide in the absence of the metal ion. The Y or Y' group would be linked to the polypeptide to form a stable covalent link (e.g., an amide linkage), followed by the addition of the metal in a reduced, chelated, exchangeable form. As chelates, α- or β-dioxo compounds are useful. Conveniently, the metal ion could be added as a weakly chelated ion or in the presence of a weakly chelating group, such as a uronate (e.g. gluconate).

A disadvantage of conjugating the chelating compound to a polypeptide before the radiolabeling step is that the radioisotope may bind to other sites on the polypeptide in addition to binding to the chelating compound. The non-specifically bound (i.e., unchelated) radioisotope may be only weakly attached and may later detach from the antibody and interfere with the diagnostic or therapeutic technique for which the radiolabeled polypeptide is to be used.

The subject chelate polypeptide conjugates (i.e., radiolabeled polypeptides having a chelate compound of the invention bound thereto) will be administered to the mammalian host, normally by injection, intravenously, intra-arterially, peritoneally, intratumorally, or the like, depending upon the particular site at which the radionuclide is desired. Generally, from about 0.1 to 2 mL will be injected into a host for diagnostic purposes, depending upon the size of the host, with about 0.001 to 50 uCi/kg of host. For human hosts the dosage will usually be about 10-50 mCi/70 kg host, more usually about 25-35 mCi/70 kg host. When the chelate polypeptide conjugates are to be injected into the bloodstream of a human, the total volume injected may be larger, e.g., 20 to 30 mls administered by intravenous infusion, as described in Example 15. For lower mammals (e.g., mice), about 1 to 50 uCi is administered for biodistribution studies, while up to or greater than 500 uCi is administered for imaging studies. After administration of the radionuclide, depending upon its purpose, the host may be treated in various ways for detection or therapy.

The diagnostic uses of the chelate-polypeptide conjugates of the invention thus provide a method for detecting the presence or absence of a particular target site within a human or mammalian host. In general, such a conjugate (e.g., a compound as shown in the formula above in which M is a $^{99m}$Tc radionuclide and Y' is a polypeptide which binds to said target site) is administered to the host, and the biodistribution of the $^{99m}$Tc is detected after waiting a predetermined length of time to allow accumulation of the compound at the target site. The diagnostic procedures may vary according to the polypeptide component of the conjugate and other factors. One such procedure is described in more detail in Example 17 below.

Technetium-99m ($^{99m}$Tc) has a physical half-life of 6 hours. Whole immunoglobulins have a biological half-life in serum of approximately 24 hours (wide range), and thus the clearance of $^{99m}$Tc-labeled antibody from the circulation is slow compared to the physical half-life of 99mTc. A 99mTc-labeled F(ab')$_2$ fragment has a shorter circulation time (T$\frac{1}{2}$ 9-20 hours) than whole immunoglobulin, which is more compatible with tumor localization and background clearance for the $^{99m}$Tc-labeled antibody fragment to provide sufficient tumor:-background ratios to image lesions successfully. Smaller fragments such as Fab', Fab and Fv have shorter circulation times (T $\frac{1}{2}$ less than 180 minutes) that are more compatible with the physical T $\frac{1}{2}$ of $^{99m}$Tc and are thus preferred for imaging applications. Choice of molecular species of antibody for imaging with other radionuclides will similarly depend on the relationship of the physical half-life of the radionuclide and the circulation time of the molecular species of antibody. $^{67}$Cu, with a physical half-life of 58.6 hours can be used with whole, F(ab')$_2$ or smaller fragments.

Choice of molecular species of antibody for therapy applications of radionuclides is more complex. In addition to physical and biologic half-lives, residence time of the labeled antibody in the tumor, energy of the emission and contribution of total body to specific organ dose are critical issues that dictate the optimal size of antibody or fragment. With monoclonal antibodies, the particular antibody will also be a factor influencing the choice.

Rhenium-188 ($^{188}$Re) has a 17-hour physical half-life, for which F(ab')$_2$ and Fab antibody fragments have suitable serum half-lives for tumor localization and background clearance. The $^{188}$Re-labeled Fab would be expected to cause less toxicity to the bone marrow, but it will usually have a shorter residence time in tumor due to the lower affinity of univalent compared to bivalent fragments. A $^{188}$Re-labeled Fab fragment with a suitably high affinity to maximize tumor residence of the delivered counts is especially useful.

Rhenium-186 ($^{186}$Re has a 3.67 day physical half-life. It can be used with whole antibody or F(ab')$_2$ or smaller fragments thereof. Because the beta energies are decreased compared to $^{188}$Re, the labeled antibody will need to have a longer residence time in the tumor.

$^{109}$Pd has a half life of 14 hours. Antibody fragments, as opposed to whole antibodies, are expected to generally be most suitable for radiolabeling in accordance with the invention.

$^{212}$Pb has a physical half-life of 10.8 hours. Fab', Fab or Fv fragments radiolabeled with $^{212}$Pb would provide the greatest tumor uptake and background clearance in that period. $^{212}$Pb decays to $^{212}$Bi which has an alpha emission with a physical half-life of 60 minutes. $^{212}$Bi itself is not a feasible label unless compartmental administration (e.g., intraperitoneal) is used. $^{212}$Pb will transmute to $^{212}$Bi in situ, and it is necessary to use a ligand that can withstand the recoil from B-decay.

$^{67}$Cu has a physical half-life of 2.44 days In general, whole antibodies or F(ab')$_2$ fragments thereof are most suitable for radiolabeling with this isotope for therapeutic use.

Delivery of the radiolabeled polypeptide may occur intravenously or by intraperitoneal, intralymphatic, intrathecal, or other intracavitary routes. Advantageously, an unlabeled (non-radiolabeled) antibody reactive with the same epitope as a radiolabeled antibody of the invention is administered prior to administration of the radiolabeled antibody, as described in the co-pending U.S. patent application having Ser. No. 917,176. The non-radiolabeled antibody functions as an "unlabeled specific blocker" to decrease binding of the later-administered radiolabeled antibody to cross-reactive sites which may be present on non-target tissue. Blocking of such cross-reactive sites is important because antibodies generally have some cross-reactivity with tissues other than a particular target tissue. In the case of antibodies directed again tumor-specific antigens, for example, virtually all such antibodies have some cross-reactivity with normal (i.e., non-tumor tissues with the exception of anti-idiotypes to B-cell lymphoma.

Antibodies to the 250 Kd glycoprotein/proteoglycan melanoma-associated antigen have been labeled with $^{99m}$Tc as disclosed in Examples 14 and 15 below. It has been discovered, for example, that prior injection of unlabeled anti-250 Kd antibody as an unlabeled or cold specific blocker decreases uptake of labeled antibody in spleen and bone marrow (see co-pending U.S. patent application having Ser. No. 917,176), and thus improves tumor localization.

The unlabeled (cold) specific blocker polypeptide advantageously is administered from about 5 minutes to about 48 hours, most preferably from about 5 minutes to about 30 minutes, prior to administration of the radiolabeled polypeptide. The length of time may vary according to such factors as the nature of the antibody and the relative accessibility of target sites versus cross-reactive binding sites. The unlabeled specific blocker and the radiolabeled antibody may be the same (except for the radiolabeling) or different, as long as both recognize the same epitope. In one embodiment of the invention, the unlabeled specific blocker is a bivalent form of an antibody (e.g., a whole antibody or a F[ab']$_2$ fragment thereof) and the radiolabeled polypeptide is a monovalent fragment of the same antibody (e.g., a F[ab]', F[ab], or Fv fragment . Use of a bivalent form of an antibody as the cold specific blocker and a monovalent form for the radiolabeled antibody has the advantage of minimizing displacement of the blocker from cross-reactive sites by the later administered radiolabeled antibody due to the greater affinity of the bivalent form. The unlabeled specific blocker polypeptide is administered in an amount effective in binding with (blocking at least a portion of the cross-reactive binding sites in a patient. Thus, binding of a radiolabeled polypeptide to cross-reactive binding sites may be reduced, thereby improving diagnostic imaging of target sites, and in general, reducing somewhat the amount of radiolabeled antibody to be administered. The amount may vary according to such factors as the size of the patient and the nature of the polypeptide. In general, about 5 mg or more of the unlabeled specific blocker is administered to a human.

Advantageously, a second antibody, termed an "irrelevant" antibody, also is administered to a patient prior to administration of the radiolabeled polypeptide. The irrelevant antibody is an antibody which does not bind to sites within the patient by a specific (e.g., antigen-binding) mechanism but which may bind to target and non-target sites through non-specific mechanisms (e.g., adsorption or binding of the Fc portion of the irrelevant antibody to Fc receptors on cells in the reticuloendotheial system). The irrelevant antibody blocks certain non-target sites in a patient and thus decreases non-specific binding of the radiolabeled polypeptide to these non-target sites, as described in copending U.S. patent application, Ser. No. 917,176. Diagnostic imaging of target sites thus may be improved, and the amount of radiolabeled antibody to be administered may be somewhat reduced. For example, prior administration of an irrelevant antibody which is not specific for any human tissues, as far as is known, effectively reduced the non-specific uptake of whole and F(ab')$_2$ radiolabeled antibody into liver and spleen in human patients.

The irrelevant antibody advantageously is administered from 5 minutes to 48 hours, most preferably from 15 minutes to one hour, prior to administration of the radiolabeled polypeptide. The length of time may vary according to such factors as the nature of the antibody. Many suitable antibodies which may be used as the irrelevant antibody are known. For example, there are many known antibodies which are not specific for any human tissues, which may be used as the irrelevant antibody. In one embodiment of the invention, a murine monoclonal antibody to a B-cell lymphoma idiotype (i.e., specific for the lymphoma cells only of one individual human) is administered as the irrelevant polypeptide. In one embodiment of the invention, the irrelevant polypeptide is a whole antibody or a F(ab)'$_2$ d fragment thereof. The irrelevant polypeptide is administered in an amount effective in blocking at least a portion of the sites at which non-specific binding (i.e., binding through non-specific mechanisms of the radiolabeled polypeptide occurs in the absence of the irrelevant polypeptide. The amount may vary according to such factors as the nature of the polypeptides and the size of the patient. In general, about 15 mg or more (preferably less than 200 mg of the irrelevant antibody is administered.

In another embodiment of the invention, the above-described chelating compounds may be included in a kit for producing a chelate-polypeptide conjugate of the invention for radiopharmaceutical use. Preferably, a specific polypeptide to be radiolabeled as described above) also is included in the kits. Reagents useful in reactions to radiolabel the chelating compound with a radionuclide and to conjugate the resulting chelate compound to the polypeptide also may be included. Such kits also may comprise a means for purifying the radiolabeled polypeptide from the reaction mixture, as well as specific instructions for producing the radiolabeled polypeptide using the kit components. Such kits generally will be used in hospitals, clinics or other medical facilities. Since such facilities generally have ready access on a daily basis to radionuclides such as isotopes of technetium, and since isotopes of rhenium, lead, bismuth, palladium, and copper may be prepared as described above, inclusion of the radionuclide in the kit is optional. Exclusion of the radionuclide permits storage of the kit, whereas kits containing the radionuclide (either as a separate component or as the radiolabeled chelate compound) would have to be used within a narrow time frame (depending on the half-life of the particular isotope); otherwise, radioactive decay of the radioisotope would diminish the effectiveness of the diagnostic or therapeutic technique for which the radiolabeled protein is used. For $^{186}$Re, on-site radiolabeling would avoid radiolytic degradation of the labeled antibody due to the beta particle emission.

The kits may be diagnostic or therapeutic kits, depending on which radioisotope is used for labeling the chelating agent. When the radionuclide is to be reduced to a lower oxidation state (e.g., technetium and rhenium, as discussed above , the kits may additionally comprise a reducing agent effective in reducing a particular metal radionuclide, to be chelated by the chelating compound, to an oxidation state at which an exchange complex of the radionuclide may be formed, and a complexing agent with which said reduced radionuclide will form said exchange complex. The kit components and instructions will be somewhat different when the chelating agent is to be radiolabeled with a technetium isotope (i.e., a diagnostic kit) than when the chelating agent is to be radiolabeled with a rhenium, lead, bismuth, palladium, or copper isotope (i.e., a therapeutic kit). The different components and procedures are discussed in more detail below.

Since the chelating compounds preferably are radiolabeled with a radionuclide prior to conjugation to a protein, a kit preferably includes a chelating compound comprising sulfur-protecting groups and a polypeptide in separate containers instead of a single container containing a chelating compound already conjugated to the protein. The term "separate containers" as used herein is meant to include not only separate, individual containers (e.g., vials) but also physically separate compartments within the same container. Thus, the radiolabeled chelate is prepared by the procedures described below, then conjugated to the polypeptide.

As discussed above, the procedures for preparing a radiolabeled protein according to the present invention may be simplified by using the above-described hemiacetals and hemithioacetals as sulfur-protecting groups. Thus, the chelating compound included in a kit preferably comprises thioacetal or hemithioacetal S-protecting groups. Preferred chelating compounds also comprise the above-described active esters, which remain intact and are reactive with the polypeptide after radiolabeling in an exchange reaction under acidic conditions, as explained above.

In accordance with one embodiment of the invention, a diagnostic kit comprises the following reagents (in separate containers unless otherwise noted), presented in the general order of use.

1. A reducing agent effective in reducing pertechnetate ($^{99m}TcO_4-$ which is in the $+7$ oxidation level) to a lower oxidation state at a neutral to acidic pH so that a technetium exchange complex can be formed. Many suitable reducing agents are known, including but not limited to stannous ion, (e.g., in the form of stannous salts such as stannous chloride or stannous fluoride), metallic tin, formamidine sulfinic acid, ferric chloride, ferrous sulfate, ferrous ascorbate, and alkali salts of borohydride. Preferred reducing agents are stannous salts.

2. A complexing agent with which the reduced $^{99m}Tc$ will form an exchange complex, thus protecting the $^{99m}Tc$ from hydrolysis. In order to achieve efficient transfer or exchange of the $^{99m}Tc$ from this complex to the chelating compound, the complexing agent advantageously binds the radionuclide more weakly than the chelating agent will. Complexing agents which may be used include, but are not limited to, gluconic acid, glucoheptonic acid, methylene diphosphonate, glyceric acid, glycolic acid, mannitol, oxalic acid, malonic acid, succinic acid, bicine, N,N'-bis(2-hydroxyethyl) ethylene diamine, citric acid, ascorbic acid and gentisic acid. Good results are obtained using gluconic acid or glucoheptonic acid as the Tc-complexing agent (or "exchange agent" in these cases), as they efficiently transfer the $^{99m}Tc$ to the $N_2S_2$ chelating agent at a pH at which the active ester is stable.

3. A chelating compound of the invention suitable for binding to the polypeptide component of the kit, as described above.

4. A protein, polypeptide or fragment thereof specific for the desired target organ, tissue, antigen or other target site within a mammalian body, as discussed above.

5. Means for purifying the desired chelate-polypeptide conjugate from the reaction mixture. Any suitable known protein purification technique may be used which effectively separates the desired radiolabeled protein conjugate from other compounds in the reaction mixture. The purification step may, for example, separate the desired conjugate from impurities due to differences in size or in electrical charge. One suitable purification method involves column chromatography, using, for example, an anion exchange column or a gel permeation column. good results have been achieved by column chromatography using an anion exchange column, e.g., a quaternary amino ethyl Sephadex (QAE-Sephadex) column or a diethyl aminoethyl Sephadex (DEAE-Sephadex) column. Since virtually all the impurities to be removed (e.g., Tc-gluconate, sodium pertechnetate, technetium dioxide and the hydrolyzed—i.e., carboxylate—form of the chelate) are negatively charged, they are substantially retained on the positively charged column. Purification thus may be accomplished by this one-step column procedure.

6. Additional reagents for use in the radiolabeling and protein conjugation reaction mixtures (e.g., the buffers, alcohols, acidifying solutions, and other such reagents, as described below) are generally available in medical facilities and thus are optional components of the kit. However, these reagents preferably are included in the kit to ensure that reagents of sufficient purity and sterility are used, since the resulting protein conjugates are to be administered to mammals, including humans, for medical purposes.

7. Optionally, a container of a polypeptide to be administered in non-radiolabeled form to a human or mammal is included in the kit. This polypeptide is reactive with essentially the same target site as the polypeptide to be radiolabeled and reduces binding of the radiolabeled polypeptide to cross-reactive binding sites on non-target tissues. The two polypeptides may be the same, or the polypeptide to be radiolabeled may, for example, be a fragment of the polypeptide which is to be administered in non-radiolabeled form. The latter polypeptide is administered as an unlabeled specific blocker (prior to administration of the radiolabeled polypeptide) in an amount effective in improving diagnostic imaging of the desired target sites (e.g., tumors as described above.

8. Optionally, the kit also comprises a container of a polypeptide which does not bind through specific mechanisms to sites within the human or mammal to which the radiolabeled polypeptide is to be administered. This polypeptide is administered as an "irrelevant" polypeptide (prior to administration of the radiolabeled polypeptide) in an amount effective in decreasing nonspecific uptake of certain radiolabeled polypeptides, as described above.

In one embodiment of the invention, a radiolabeled polypeptide may be produced using such a kit according to the following general procedure. The procedure is conducted under sterile conditions. In this particular embodiment of the invention, the kit comprises reagents in amounts suitable for preparation of an amount of radiolabeled polypeptide suitable for injection into one human for diagnostic purposes.

An aqueous solution comprising a reducing agent and a complexing agent is prepared. Good results are achieved by combining stannous chloride dihydrate (comprising the stannous ion reducing agent) and sodium gluconate (a complexing agent) to form a stannous gluconate complex. This stannous gluconate complex may be provided in a single container in the kit. In one embodiment of the invention, the stannous gluconate complex is provided in the kit in dry solid form. Optionally, one or more stabilizer compounds may be added to the stannous gluconate complex. Many such stabilizer compounds are known and are discussed in connection with the therapeutic kits below. For example, gentisic acid may be added to a container of the stannous gluconate complex to stabilize (minimize oxidation of) the stannous ion reducing agent, and the resulting mixture may be provided in the kit in dry solid form or as a lyophilized preparation. A filler compound advantageously is added prior to lyophilization, as described for the therapeutic kit below. For example, lactose may be added as a filler compound in an amount effective in facilitating lyophilization. The amounts of stannous chloride and sodium gluconate preferably are not so large as to have adverse effects on the desired reactions and product. For example, excessively large amounts of non-reacted (free) stannous chloride dihydrate may harm the polypeptide added in a later step, e.g., by adversely affecting the immunoreactivity of an antibody. An excessively large amount of free sodium gluconate may slow the transchelation step and require addition of excessive amounts of buffer necessary to raise the pH in subsequent steps, and the reaction mixtures would then be undesirably dilute. An acceptable ratio of stannous chloride dihydrate to sodium gluconate (by weight) is from about 1:10 to about 1:100, preferably from about 1:25 to about 1:70, most preferably about 1:41.6.

The amount of $^{99m}Tc$ added may vary. When the diagnostic kit is designed for preparation of a radiolabeled protein to be injected into a single human patient, the amount of pertechnetate to be added to the following reaction mixture may be from about 50 to about 200 mCi, preferably from about 75 to about 100 mCi of the radioisotope. Greater amounts may interfere with the reaction and produce low yields, as well as being an excessive amount of radioactivity for administration to a single patient, as described in the examples below. When about 75 to 100 mCi of $TcO_4-$ are to be added, the stannous gluconate complex preferably comprises (i.e., is formed from) about 3 to about 10 mg of sodium gluconate and about 0.075 to about 0.250 mg of stannous chloride dihydrate; preferably from about 4 to about 6 mg of sodium gluconate and about 0.075 to about 0.125 mg of stannous chloride dihydrate.

Sodium pertechnetate is combined with the reducing agent and complexing agent. When the sodium pertechnetate is added to stannous gluconate, the radioisotope is effectively reduced to a lower oxidation state and complexed with gluconate to form an exchange complex. The stannous gluconate and pertechnetate may be combined in various ways. In one embodiment of the invention, sterile water is added to a vial containing a stannous gluconate preparation in dry solid form. A portion of the resulting solution is combined with about 0.75 mL sodium pertechnetate (about 75 to 100 uCi). In another embodiment of the invention, sodium pertechnetate (about 1 mL) is added directly to a lyophilized preparation comprising stannous gluconate, gentisic acid as a stabilizer, and lactose as a filler compound. In either case (both of which are described more fully in example 15 below), the reaction mixture is incubated at about 25° C. to about 50° C., preferably at about 25° C. to about 37° C. for a minimum of 10 minutes. Incubation for 10 minutes generally gives sufficient yields of the desired technetium exchange complex (e.g., technetium gluconate) while minimizing the formation of insoluble technetium dioxide, which may increase with increased incubation time.

A chelating compound of the invention, comprising a thioacetal or hemithioacetal S-protecting group, as described above, is added to an organic solvent effective in dissolving the chelating compound and suitable for the exchange reaction that follows. Suitable solvents should be nontoxic in mammals and inert toward the reactants in the reaction mixture. Organic solvents which may be used include acetonitrile, ethyl acetate, and methylethyl ketone. When the radiolabeled protein is to be injected into humans, however, suitable organic solvents include, but are not limited to, alcohols such as ethanol, butanol, t-butyl alcohol and propanol, and polar aprotic solvents such as DMSO and dimethylformamide. The choice of solvent may vary according to the particular chelating agent included in the kit. For example, when the chelating compound comprises a tetrafluorophenyl ester group, ethanol will react with the ester in a transesterification reaction, producing ethyl ester as a by-product, which is much less reactive toward free amine groups on proteins. A preferred organic solvent is isopropyl alcohol. The concentration of the organic solvent in the following Tc-labeling exchange reaction mixture should be between about 10% and about 30%, preferably between about 15% and about 25%.

The solution comprising the chelating agent in the organic solvent is then acidified to a pH of about 2.0 to about 5.0, preferably 2.8 to 3.3. At these acidic pH conditions, the formation of insoluble $TcO_2$ will be minimized, and, as explained above, hemithioacetal and thioacetal sulfur-protecting groups will be displaced by a metal-assisted acid cleavage during the technetium labeling exchange reaction to form the corresponding technetium chelate compound. Also, hydrolysis of ester groups on the chelating compound is minimized under acidic conditions when compared to basic conditions. Suitable acids are added in amounts sufficient to displace the sulfur-protective groups in the presence of the metal radionuclide (i.e., in amounts sufficient to adjust the reaction mixture to the above-described pH values range). Suitable acids include, but are not limited to, phosphoric acid, sulfuric acid, nitric acid, glacial acetic acid, hydrochloric acid and combinations thereof. Also included are solutions comprising such acids and buffers (e.g., acetate and phosphate buffers). Good results have been achieved using a solution comprising glacial acetic acid and 0.2 N HCl at a ratio of 2:14.

The acidified chelating compound solution is combined with the previously prepared technetium exchange complex solution, to form the corresponding chelate compound, such that about 100 ug to about 150 ug, preferably about 135 ug of chelating compound is combined with the Tc-gluconate complex prepared from the 75 to about 100 mCi of technetium as described above. The reaction mixture is heated to between about 50° C. and 100° C. for from about 5 minutes to about 45 minutes. Good results have been achieved by heating at about 75° C. for about 15+2 minutes. Heating the reaction mixture accelerates the exchange reaction to form the $N_2S_2$ chelate. Upon completion of the reaction, the mixture is transferred immediately to a 0° C. ice bath for a minimum of 2 minutes to stop the reaction quickly and minimize hydrolysis of the ester group.

An aqueous solution comprising a buffer then is added to the reaction mixture to reduce the concentration of the organic solvent (e.g., isopropanol) and to raise the pH before adding the polypeptide to be radiolabeled. Suitable buffers include nontoxic buffers which are inert toward the reactants, such as, but not limited to, sodium phosphate buffer and sodium bicarbonate buffer, preferably at a concentration of about 1.0 M and a pH of about 10. Buffers such as TRIS are not suitable because the free amine groups of TRIS are reactive with the ester group on the chelate compound. Sufficient buffer is added to reduce the organic solvent concentration to from about 10% to about 15%, preferably from about 7.5% to about 12.5%, and to raise the pH of the Tc-chelate solution to about 5.5. If the pH were raised to higher levels (e.g., pH 9 or above) before addition of the polypeptide, the polypeptide would not be available to react with the ester, which would remain as a free ester group subject to hydrolysis at the higher pH. A buffer, preferably the same buffer, is added to a solution of the desired polypeptide. The polypeptide may be provided in the kit in any form in which the desired biological activity is preserved. The polypeptide may, for example, be provided in a buffered solution having a biologically acceptable pH, i.e., a pH at which the polypeptide may be stored in the kit without significant loss of biological activity. In one embodiment of the invention, the polypeptide is provided in the kit in phosphate buffered saline (PBS) at a pH of about 7.0 to about 7.4. The buffered polypeptide solution is added to the buffered Tc-chelate prepared above. Sufficient buffer is added to the protein solution so that the final pH of the protein conjugation reaction mixture is from about 9 to about 11. The concentration of the protein in the conjugation reaction mixture should be at least about 1 mg/mL to achieve adequate yields of radiolabeled protein. Increasing the final protein concentration above about 8 mg/mL generally does not increase the yield significantly. Preferably, the final protein concentration is about 5 mg/mL. The reaction is incubated at 0° C. to 37° C. for about 10 minutes to about 35 minutes, preferably at about 20° C. to 25° C. for about 20 minutes. The pH and temperature of the reaction mixture should be kept within physiologically acceptable limits to prevent loss of biological activity of the protein. The resulting radiolabeled protein is purified by known methods, as described above. The method chosen may vary according to such factors as the size of the protein or protein fragment.

In accordance with another embodiment of the invention, a therapeutic kit comprises the following reagents.

1 A reducing agent effective in reducing $ReO_4-$, which is in the +7 oxidation level, to a lower oxidation state at a neutral to acidic pH so that a rhenium exchange complex can be formed. Many suitable reducing agents are known, including but not limited to stannous ion (e.g., in the form of stannous salts such as stannous chloride or stannous fluoride), metallic tin, formamidine sulfinic acid, ferric chloride, ferrous sulfate, ferrous ascorbate, and alkali salts of borohydride. Preferred reducing agents are stannous salts.

2. A complexing agent with which the reduced Re will form an exchange complex, thus protecting the Re from hydrolysis. In order to achieve efficient transfer or exchange of the Re from this complex to the $N_2S_2$ chelating compound, the complexing agent advantageously binds the radionuclide more weakly than the chelating agent will. Complexing agents which may be used include, but are not limited to, methylene diphosphonate, glyceric acid, glycolic acid, mannitol, oxalic acid, malonic acid, succinic acid, bicine, N,N'-bis(2-hydroxyethyl) ethylene acid, succinic diamine, citric acid, ascorbic acid, gentisic acid, tartric acid, and gluconic acid. Good results are obtained using citric acid as the Re-complexing agent (or "exchange agent" in these cases).

3. A chelating compound of the invention suitable for binding to the polypeptide component of the kit, as described above.

4. A protein, polypeptide or fragment thereof specific for the desired target organ, tissue, antigen or other site within a mammalian body, as discussed above.

5. Means for purifying the desired chelate-polypeptide conjugate from the reaction mixture. Any suitable known protein purification technique may be used which effectively separates the desired radiolabeled protein conjugate from other compounds in the reaction mixture. The purification step may, for example, separate the desired conjugate from impurities due to differences in size or in electrical charge. One suitable purification method involves column chromatography. Good results have been achieved by column chromatography using a gel permeation column or an anion exchange column (e.g., a QAE-Sephadex or DEAE-Sephadex column). Since virtually all the impurities to be removed (e.g., Re-citrate, perrhenate and the hydrolyzed [i.e., carboxylate]form of the chelate) are negatively charged, they are substantially retained on the positively charged column. Purification thus may be accomplished by this one-step column procedure.

6. Optionally, the kit may contain another column for purification of the chelate after the radiolabeling step. Any suitable reverse-phase column may be used, such as a C-18 or C-8 Baker column.

7. Additional reagents for use in the radiolabeling and conjugation reaction mixtures (e.g., the buffers, alcohols, acid solutions, etc., as described below) are generally available in medical facilities and thus are optional components of the kit. However, these reagents preferably are included in the kit to ensure that reagents of sufficient purity and sterility are used, since the resulting protein conjugates are to be administered to mammals, including humans, for medical purposes.

8. The kit also may include a container of an antibody to be administered as an unlabeled specific blocker, as well as a container of an appropriate antibody to be administered as an irrelevant antibody. The unlabeled specific blocker and irrelevant antibodies are administered as described above to improve localization of the radiolabeled polypeptide at the desired target site.

In one embodiment of the invention, a polypeptide radiolabeled with either $^{188}Re$ or $^{186}Re$ may be prepared using such a kit, according to the following general procedure. The procedure is conducted under sterile conditions.

Perrhenate (the $ReO_4-$ form of the $^{186}Re$ or $^{188}Re$ isotope) is reacted with a reducing agent and a complexing agent. Good results are achieved by combining citric acid (a complexing agent) with stannous chloride (a reducing agent) in a single container (in which a stannous citrate complex is believed to form) and adding the perrhenate thereto.

The amounts of stannous chloride and citric acid added should not be so large as to have adverse affects on the desired reactions. For example, excessively large amounts of non-reacted (free) stannous chloride may harm the polypeptide added in a later step (e.g., by adversely affecting the immunoreactivity of an antibody). An excessively large amount of free citric acid may lower the pH to a level which makes addition of large quantities of buffer necessary to raise the pH in subsequent steps, and the reaction mixtures would be undesirably dilute. An acceptable ratio of stannous chloride to citric acid (by weight) generally is from about 1:10 to about 1:5500, preferably from about 1:20 to about 1:200, most preferably about 1:100.

One or more stabilizer compounds may be added to the stannous citrate complex. Many such stabilizer compounds are known. See, for example, U.S. Pat. Nos. 4,440,738 and 4,510,125. Advantageously, gentisic acid is added to the stannous citrate to stabilize (e.g., to prevent oxidation of) the stannous ion. The stabilizer is added to a solution comprising the stannous chloride reducing agent (and the complexing agent) in an amount effective in stabilizing the stannous ion such that the shelf life (stability) of the stannous ion is increased. The solution may be lyophilized and provided in the kit as a lyophilized powder.

When the stannous citrate solution is to be lyophilized, a "filler compound" may be added to the solution to provide bulk or mass and to aid in the lyophilization process. Good results have been achieved using lactose as the filler compound.

In one particular embodiment of the invention, an aqueous solution of stannous citrate was prepared by combining about 75 mg citric acid with about 750 ug stannous chloride. About 250 ug gentisic acid was added. When 50 ug of gentisic acid was added, the stabilizing effect was not as efficient, whereas 1 mg gentisic acid was found to be too large an amount, having a negative affect on yields. About 100 mg lactose (a preferred amount) is then added to the preparation, although about 20 mg is generally adequate. The final solution (about 2 mLs volume) then is lyophilized.

Perrhenate is added to the stannous citrate preparation. Perrhenate can be introduced into the preparation as an aqueous solution of the sodium salt (e.g., eluted from a rhenium generator) or as an aqueous solution of the tetrabutylammonium ion pair, as described in Example 16 below. Either way, perrhenate is incubated with a solution comprising a reducing agent and a complexing agent. The reaction mixture is incubated at about 25° C. to about 50° C, preferably at about 25° C. to 37° C., for a minimum of 10 minutes. Incubation for 10 minutes generally gives sufficient yields of the desired rhenium exchange complex (e.g., rhenium-citrate), while minimizing the formation of insoluble rhenium dioxide.

A chelating compound of the invention comprising thioacetal or hemithioacetal sulfur-protecting groups, as described above, is dissolved in an organic solvent effective in dissolving the chelating compound and suitable for the exchange reaction that follows. Suitable solvents should be non-toxic in mammals and inert toward the reactants in the reaction mixture. Organic solvents which may be used include acetonitrile, ethyl acetate, and methyl ethyl ketone. When the radiolabeled protein is to be injected into humans, however, suitable organic solvents include but are not limited to alcohols such as ethanol, butanol, t-butyl alcohol, and propanol and polar aprotic solvents such as DMSO and dimethylformamide. The choice of solvent may vary according to the particular chelating agent included in the kit. For example, when the chelating compound comprises a tetrafluorophenyl ester group, ethanol will react with the ester in a transesterification reaction, producing ethyl ester by-products which are undesirably lipophilic and which are much less reactive toward free amine groups on proteins. A preferred organic solvent is isopropyl alcohol.

The solution comprising the chelating compound is combined with the rhenium exchange complex solution prepared above to form the corresponding rhenium chelate compound. The reaction advantageously is conducted at a pH of from about 1.5 to about 5.0, preferably from about 1.7 to about 2.0. At these acidic pH conditions, the formation of insoluble $ReO_2$ will be minimized; and as explained above, hemithioacetal and thioacetal sulfur-protecting groups will be displaced by a metal-assisted acid cleavage during the rhenium labeling exchange reaction to form the corresponding rhenium chelate compound. Also, hydrolysis of ester groups on the chelating compound is minimized under acidic conditions when compared to basic conditions. If adjustment of the pH of the reaction mixture is necessary, suitable acids may be added in amounts sufficient to displace the sulfur-protective groups in the presence of the metal radionuclide (i.e., in amounts sufficient to adjust the reaction mixture to the above-described pH values range). Suitable acids include but are not limited to phosphoric acid, sulfuric acid, nitric acid, glacial acetic acid, hydrochloric acid, and combinations thereof. Also included are solutions comprising such acids and buffers (e.g., acetate and phosphate buffers).

The amount of chelating agent reacted with the Re-citrate intermediate may vary according to the reaction volume, which in turn varies according to the volume in which perrhenate was added in an earlier step (e.g., perrhenate may be added as an eluate from the generator or may first be concentrated. In one embodiment of the invention, good results have been achieved when the concentration of chelating compound in the reaction mixture (in which the chelate is formed) is about 100 ug to about 200 ug of chelating compound per mL of reaction mixture.

The reaction mixture is heated between about 50° C. and 100° C. for from about 5 to about 45 minutes. Good results have been achieved by heating at about 75° C. for about 10 minutes. Upon completion of the reaction, the mixture is transferred immediately to a 0° C. ice bath for a minimum of 2 minutes to stop the reaction and minimize the hydrolysis of the ester group.

The next step (protein conjugation) may vary according t the volume of the reaction mixture in which the chelate was formed, which may vary according to the volume of the perrhenate solution added earlier. When the perrhenate was added in a relatively large volume (e.g., about 3 mLs as an eluate from a generator as in Example 16 below), the chelate may be purified from the chelation reaction mixture using a preparative reversed phase column. Suitable columns include but are not limited to Baker C18 and C8 columns. The desired chelate is retained by the column packing material, while most impurities (e.g., starting reagents such as citric acid, gentisic acid, stannous chloride, and lactose) may be washed off the column. Good results have been achieved by washing the column (after sample loading) several times with water, then several times with a 2% to 20% ethanol/phosphate buffer solution. The column then is dried, and the chelate compound is eluted with an organic solvent, preferably $CH_3CN$, that can be dried off under mild conditions. Usually, a flow of nitrogen dispensed through needles evaporates all the solvent, leaving a white residue in the elute vial. An aqueous solution comprising a buffer is added to the protein to be radiolabeled, which in turn is added to the vial containing the chelate. Sodium bicarbonate buffers are preferred. The other parameters for the protein conjugation step are as presented above for the diagnostic kit.

Alternatively, when perrhenate is added to the stannous citrate preparation in a smaller volume (e.g., when the perrhenate has been concentrated as a tetrabutylammonium ion pair [see Example 16]), an aqueous solution comprising a buffer is directly added to the chelation reaction mixture to raise the pH to about 5.5 before adding the protein to be radiolabeled. The choice of the buffer is as presented for the diagnostic kit. The same buffer is added to the polypeptide to be radiolabeled, which in turn is added to the buffered Re-chelate. Sufficient buffer is added to the protein solution so that the final pH of the conjugation reaction is from about 9 to about 11. The concentration of the protein and the temperature during conjugation are similar to those already presented for the diagnostic kit.

After the protein conjugation step, L-lysine may be added to the reaction mixture to displace the ester containing chelate compound which may be associated with (e.g., adsorbed to) but not covalently bound to the protein. It is believed that reaction of the ester group on the chelate with the free amine group of L-lysine helps displace non-covalently bound chelate from the protein.

The desired radiolabeled polypeptide (i.e., the chelate-polypeptide conjugate) then is purified from the reaction mixture using any suitable means. Good results may be achieved using an anion exchange column (e.g., a DEAE Sephadex or QAE Sephadex column) or a gel permeation column. A QAE-Sephadex column is generally preferred.

The following examples are offered by way of illustration and not by way of limitation.

EXAMPLES

Example 1

Synthesis of N,N'-bis(benzoylmercaptoacetyl)-3,4-diamino Butyrate.

In a dry flask under nitrogen is placed 1.54g (0.010 mole) of 3,4-diaminobutyric acid hydrochloride and 250 mL of absolute ethanol. Dry HCl gas is then bubbled into the solution. The mixture is refluxed for one to two days until formation of the ethyl ester is complete. The product is then concentrated to a dry solid and the hydrochloride ester dissolved by rapid stirring at ice bath temperature in a mixture of 50 mL toluene and 50 mL of saturated sodium bicarbonate. To this solution is added 5.0 g 0.044 mole) of chloroacetyl chloride in 10 mL of toluene by dropwise addition. After addition is complete, the mixture is allowed to come to room temperature and stirred for an additional 30 minutes. Layers are separated, and the aqueous portion is extracted twice with ethyl acetate. The organic layers are combined, washed with water and brine, and dried (magnesium sulfate). Removal of the solvent leaves the product as a white solid, which may be used without further purification.

A solution of 1.41 g (about 4.45 mmole) of the bis-chloroacetamide is prepared in 10 mL of dry ethanol under nitrogen. To this is added a solution of sodium thiobenzoate in dry ethanol, prepared from sodium methoxide (0.204 g of sodium, 8.87 mmole, and ethanol), which is reacted with 1.23 g (8.90 mmole) of thiobenzoic acid. After a few minutes at room temperature, precipitation occurs. The reaction is heated to reflux for 30 minutes. It is then allowed to cool, diluted with ethyl acetate, washed with water and brine and dried (magnesium sulfate). Removal of solvent leaves a cream-colored solid which may be recrystallized from toluene.

Example 2

Radiolabeling with Tc-99m.

1. The product prepared in Example 1 (0.1 mg) is dissolved in 0.3 mL of ethanol by heating and 30 ul of 5 N sodium hydroxide and 0.3 mL of water added in succession. After heating for 15 minutes at 95oC during which time the ethanol evaporated, an essentially aqueous solution of the hydrolyzed ligand is left. To the mixture is then added generator pertechnetate in saline (0.5 mL or less which includes about 30 mCi or less of Tc-99m and 0.5 mg of freshly dissolved sodium dithionite; or (2) after allowing the mixture to stand for a short period at room temperature, the mixture is heated to 95° C. for an additional 15 minutes and the pH adjusted to about 8.

2. The protected thiol, free carboxylic acid ligand of Example 1, 0.10 mg, is added to 20 mg of sodium gluconate and 0.010 mg of $SnCl_2 \cdot 2H_2O$, pH adjusted to 5 The Tc-99m as pertechnetate is added to the mixture and the mixture heated at 95° C. for 5 minutes.

The product mixture may be purified by preparative HPLC, using a 25cm octadecylsilane column (Altex Model 312 chromatograph; 4.6×250mm ODS ultrasphere, 5u) and eluting with 95% 0.01 M sodium phosphate (pH 6) and 5% ethanol with a flow rate of 1.0 mL/minute. The preparations are analyzed for reduced hydrolyzed technetium on silica gel thin-layer strips.

Example 3

Formation of Activated Esters.

The conditions for formation of the activated esters are as follows: Into a reaction flask is introduced the carboxylic acid ligand or tracer level of metal complex carboxylate and an equimolar amount of the hydroxylic compound and a small excess, about 25% excess, of 1-ethyl-3-dimethylaminopropyl carbodiimide hydrochloride (ECDI and 400 ul of dimethylformamide (DMF). Upon completion of the reaction, sodium acetate is added to quench unreacted ECDI and the solution is ready for use for conjugation.

The protein to be conjugated is dissolved in 0.2 M borate buffer, pH 8.5 to 9.0, to a protein concentration of about 2 to 5 mg/mL. The mixture is allowed to stand at 4° C. until all of the protein has dissolved. To the aqueous protein solution at a pH adjusted to 8.5-9.0 is added the ester solution and the pH readjusted if necessary. The resulting conjugate is then preparatively chromatographed on an HPLC gel filtration column with 0.05 M phosphate, pH 7.4, buffer as eluant.

In the following study, various conditions were employed, employing activated esters of technetium chelate prepared as described above for reaction with immunoglobulin under varying conditions of time, temperature, concentration and pH. The following Table 1 indicates the results.

TABLE 1

Reactions of Activated Esters of N,N'-bis(mercaptoacetyl)-3,4-diaminobutanoate (Tc-99m) with Immunoglobulin under Different Conditions

| Activated Exter | pH | Protein mg/ml | T(°C.) | t(min) | % Labeled Protein | % Ester Hydrolyzed | % Ester Unreacted |
|---|---|---|---|---|---|---|---|
| p-nitrophenyl | 6.94 | 1.0 | 23 | 22 | 0.5 | 3.7 | 95.8 |

TABLE 1-continued

Reactions of Activated Esters of N,N'-bis(mercaptoacetyl)-3,4-diaminobutanoate (Tc-99m) with Immunoglobulin under Different Conditions

| Activated Ester | pH | Protein mg/ml | T(°C.) | t(min) | % Labeled Protein | % Ester Hydrolyzed | % Ester Unreacted |
|---|---|---|---|---|---|---|---|
| | 6.94 | 1.0 | 23 | 77 | 1.7 | 8.2 | 90.1 |
| | 6.94 | 1.0 | 37 | 60 | 4.3 | 17.5 | 78.2 |
| | 6.94 | 1.0 | 37 | 105 | 6.4 | 24.9 | 68.7 |
| | 8.70 | 1.0 | 23 | 105 | 12.0 | 33.0 | 68.7 |
| | 8.70 | 1.0 | 34 | 120 | 15.0 | 69.0 | 8.0 |
| | 8.70 | 1.0 | 23 | 320 | 20.0 | 50.0 | -23.0 |
| | 9.69 | 1.0 | 23 | 120 | 13.0 | 76.0 | 7.0 |
| 2-chloro-4-nitrophenyl | 8.55 | 1.0 | 23 | 240 | 34.0 | 62.0 | 4.0 |
| | 8.55 | 1.0 | 0 | 240 | 37.0 | 60.0 | 3.0 |
| | 9.22 | 1.0 | 23 | 300 | 26.0 | 72.0 | 2.0 |
| | 9.22 | 1.0 | 0 | 330 | 30.0 | 66.0 | 4.0 |
| | 8.61 | 3.0 | 23 | 30 | 46.0 | 39.0 | 15.0 |
| | 8.61 | 3.0 | 0 | 60 | 38.0 | 46.0 | 16.0 |
| | 8.61 | 3.0 | 23 | 75 | 51.0 | 38.0 | 11.0 |
| | 8.61 | 3.0 | 0 | 100 | 44.0 | 42.0 | 14.0 |
| hydroxybenztriazole | 6.80 | 1.0 | 23 | 30 | 8.4 | 45.4 | 46.0 |
| | 6.80 | 1.0 | 23 | 60 | 10.3 | 48.3 | 39.0 |
| | 6.80 | 1.0 | 23 | 120 | 10.8 | 53.3 | 35.8 |
| | 8.50 | 1.0 | 23 | 90 | 10.3 | 61.0 | 23.0 |
| | 8.70 | 1.0 | 5 | 120 | 32.0 | 30.0 | 32.0 |
| | 8.70 | 1.0 | 5 | 240 | 34.0 | 30.0 | 30.0 |
| | 9.25 | 1.0 | 5 | 45 | 12.0 | 33.0 | 53.0 |
| | 9.25 | 1.0 | 5 | 90 | 13.0 | 32.0 | 53.0 |
| | 9.40 | 1.0 | 23 | 60 | 4.3 | 66.0 | 21.0 |

Example 4

Synthesis of 4,5-diaminopentanoate.

To a solution of 50.5 g of sodium bicarbonate in 200 mL of water was added 85.0 g of glutamic acid gamma-ethyl ester and the mixture cooled in an ice-salt bath. While maintaining the temperature between 0°-5° C., 40 g of carbobenzoxy chloride was added and the mixture stirred for 5 hours followed by warming to room temperature and stirring for an additional 2 hours. After extraction 2×100 mL of ether, the mixture was acidified with 6 N HCl to Congo red (pH 3). The separated oil was extracted with 3×100 mL methylene dichloride, the combined organic layers washed with brine and water and then dried over anhydrous sodium sulfate. Evaporation and crystallization from 200 mL carbon tetrachloride gave a yield of 46.3 g (77%). MP86°-88° C.

To a solution of 46 g of the above product in 45 mL of THF at 35°-40° C. was rapidly added BH$_3$-THF (0.18 mmol in 178 mL). After 3 hours, an aliquot on TLC (ethyl acetate hexane 4:1) showed substantially complete conversion to the alcohol.

Fifty mL of ethanol was added to the reaction mixture and the mixture evaporated to dryness. After repeating the procedure twice with 100 mL of ethanol, the residue was suspended in water, extracted with ethyl acetate and the organic layer washed successively with 2×100 mL of 2% aqueous bicarbonate and water, followed by drying over anhydrous sodium sulfate. The organic solvent was then evaporated, the residue dissolved in hexane and upon cooling gave 30.8 g (71%) yield of a low-melting solid. MP86°-88° C.; TLC (R$_f$ ethyl acetate-hexane 0.19).

The alcohol (29.5 g) prepared above was dissolved in 90 mL of pyridine (0°-5° C.) and 19.5 g of tosyl chloride added at once. Precipitation of pyridinium-hydrochloride was observed after 1 hour and the mixture stirred for 2 hours more, followed by storage at 4° C. overnight. The solution was poured with stirring into a liter of ice-water and the resulting solid isolated by filtration, washed with water and dried in a desiccator overnight to yield 35 g (80%) of the tosyl ester. MP73° C.-76° C.

To the tosyl ester (22.45 g) in 150 mL of DMF was added 3.9 g of sodium azide and the mixture heated at 50°-55° C. for 3 hours. At the end of this time, the DMF was removed in vacuo at 5-10 torr., cold water added and filtered. The resulting azide was dried in a desiccator overnight to yield 14.56 (91%) of the desired product. MP60° C.-63° C.

Into 227 mL of 1 N HCl-ethanol (abs) was dissolved 14 g of the above zide and the solution carefully added to 1.4 g of platinum oxide in a hydrogenation bottle. The mixture was hydrogenated at 50° -55° C. for 48 hours and the course of the reduction followed by TLC. At completion of the reaction, the catalyst was removed by filtration, the filtrate evaporated to dryness and the residue dissolved in 325 mL of 6 N HCl and the mixture refluxed for 36 hours. After filtration and evaporation to dryness, the residue was dissolved in 100 mL of water, the water evaporated and the process repeated twice. The residue was triturated with ethanol to yield 8.3 g (91%) of the diamino acid product. MP 250° C.

Example 5

Synthesis of Antibody N$_2$S$_2$ Conjugate Using o-Nitrophenyl Disulfide Protected Ligand.

To 2.05 g of the above diamino acid dissolved in 50 mL of DMF was added triethylamine (3 mL) and succinimidyl S-benzoyl trioglycolate (5.86 g) and the mixture stirred for 15 minutes. Dimethylformamide was removed in vacuo and 100 mL of cold water was added. The precipitated oil solidified on standing. The solid was filtered, dried and crystallized from ethyl acetate. MP 126°-127° C.

To sodium ethoxide (140 mg sodium) in 30 mL ethanol was added 0.966 of the above product and the mixture stirred overnight at room temperature. After evaporating the solvent in vacuo, the residue was dissolved in glacial acetic acid, the solvent evaporated and the process repeated twice. The residue was redissolved in 30 mL of glacial acetic acid and 0.77 g of o-nitrophenylsulfenyl chloride added and the mixture stirred at room temperature for 24 hours. The reaction was monitored by TLC (acetonitrile-water 95:5), and at completion of the reaction, the acetic acid was removed in vacuo and cold water added. The solid precipitate was filtered, washed with cold ethanol (10–15 mL) and dried in vacuo for 12 hours over $P_2O_5$. The yield was 1.03 g (88%). MP 200° C. TLC:acetonitrile:water 95:5 $R_f$0.39.

To the bis-(di-o-nitrophenyldisulfide (0.293 g) suspended in 50 mL THF (anhydrous) was added N-hydroxysuccinimide (63 mg) followed by dicyclohexylcarbodiimide (113 mg) and the mixture stirred for 48 hours at room temperature. The solution was concentrated to about 15–20 mL and cooled, the precipitate removed by filtration and the filtrate diluted with 25–30 mL of ethyl acetate, followed by washing the organic layer with water. The organic layer was dried over magnesium sulfate, concentrated to 20 mL and cooled. The resulting precipitate was filtered, the filtrate concentrated to about 10 mL and cooled to about 10° C.–15° C. After filtration, the filtrate was maintained at about 4° C. for 2–3 hours. Addition of anhydrous ether to the cold solution resulted in a yellow precipitate (about 95 mg), followed by a second crop of about 90 mg of an impure product.

The antibody conjugation reaction was contained in a final volume of 40 mL: 1.8 mg ($1.72 \times 10^{-5}$ moles) bis-(di-o-nitrophenyldisulfide) $N_2S_2$ ligand, 178 mg of mouse monoclonal antibody (IgG, $1.2 \times 10^{-6}$ moles), 4.0 mL of redistilled DMF, 0.05 M sodium borate buffer pH 8.5. After stirring 90 minutes at room temperature, 4.4 mL of 5 N sodium chloride and 1.9 mL of 100 mM dithiothreitol were added. After an additional 30 minutes the reaction mixture was centrifuged to remove any particulates and the supernatant fractionated by gel filtration column chromatography. The column eluent was monitored at 280 nm, and the fractions containing the monomeric antibody conjugate were pooled and concentrated in an Amicon stirred cell (30,000 molecular weight cutoff). Final yield was 141 mg (82%).

Example 6

Technetium-99m Labeling of Antibody-Ligand Conjugate with Tc-Tartrate.

Stannous tartrate kits were prepared from degassed solutions of 0.5 mL disodium tartrate (150 mg/mL) and 0.1 mL stannous chloride (1.0 mg/mL in ethanol) in an evacuated vial under nitrogen atmosphere. To a stannous tartrate kit, sodium pertechnetate 0.5 mL (about 15 mCi) was added and heated at 50° C. for 10–15 minutes. After cooling to room temperature, quality control for Tc-99m tartrate and insoluble Tc-99m was carried out on Gelman ITLC using methyl ethyl ketone and 0.01 M sodium tartrate pH 7.0 eluents, respectively. Tc-99m tartrate formation was typically 98–99% with soluble Tc-99m values ranging from 0.1 to 0.2%.

In an evacuated vial, 100 ul saline, 200 ul of sodium phosphate (0.2 M, pH 8.0) and 200 ul of antibody-ligand conjugate (1.9 mg/mL were added successively. Immediately after adding the conjugate, 250 ul of Tc-99m tartrate (about 3 to 5 mCi was added and heated at 50° C. for 1 hour. Percent technetium bound to protein and the formation of pertechnetate were determined by ITLC using 50% MeOH:10% ammonium acetate (1:1) and 1-butanol eluents, respectively. Technetium incorporation typically ranged from 70–88% on a ligand -Ab conjugate with a ligand per antibody ratio of 1.5 to 3.0.

TABLE 2

Comparative Biodistribution of Tc-99m and Iodine-125 Anti-melanoma Antibody 9.2.27 in Mice Bearing Melanoma Tumors from FEMX Cell Line.

| | Organ | | | | | | |
|---|---|---|---|---|---|---|---|
| | Tumor | Liver | Spleen | Lung | Stomach | Thyroid | Kidney |
| Tc-99m | 5.78* | 1.54 | 1.34 | 1.79 | 0.26 | 0.61 | 1.72 |
| | ±0.32 | ±0.19 | ±0.14 | ±0.67 | ±0.15 | ±0.05 | ±0.12 |
| I-125 | 3.97 | 1.07 | 1.59 | 1.81 | 2.99 | 7.79 | 1.33 |
| | ±0.61 | ±0.17 | ±0.03 | ±0.12 | ±1.89 | ±4.50 | ±0.04 |

*Data are mean ± S.D. percent injected dose per gram for three mice at 48 hours post injection. The method of Hwang, et al., Cancer Res. (1985) 45:4150–4155 was employed.

Example 7

Labeling of Antibody with Preformed Tc-99m Pentanoyl $N_2S_2$ Chelate.

A Tc-99m chelated derivative was conjugated to an antibody as follows. Tc-99m (75 mCi) chelated by N,N'-bismercaptoacetyl 4,5-diaminopentanoic acid was prepared by dithionite reduction of Tc-99m pertechnetate at basic pH with 25 ug of the $N_2S_2$ ligand. The acid was activated by adding the above complex at pH 7 in 0.5 mL water to 100 ul of water:acetonitrile (1:9) containing 3.0 mg of 2,3,5,6-tetrafluorophenol and 100 ul of $H_2O$: acetonitrile (1 9) containing 7.5 mg of 1-cyclohexyl-3-(2-morpholinoethyl)carbodiimide (morpho CDI) added. After storing for 18 hours at room temperature, the mixture was purified using a Baker-10 SPE reversed phase $C_{18}$column. The column was conditioned with 2 mL of ethanol followed by washing with HPLC grade water. The reaction mixture was then added to the column, the column washed 4 times with 2 mL volumes of 10% methanol in 0.01 M sodium phosphate, pH 7.0, and the ester complex eluted with 2.5 mL portions of acetonitrile. The first eluent contained 8.5 mCi and the second 0.18 mCi. The yield was 86% after accounting for decay.

To a 2 mL vial was added 4.5 mCi of activated ester complex in acetonitrile, the solvent evaporated in a nitrogen stream and 0.40 mL of sodium borate (0.5 M, pH 9.0) added. With stirring, 30 1 (9.14 mg/mL) of antimelanoma antibody (9.2.27 was added. The final protein concentration was 0.52 mg/mL. The reaction was followed with TLC using Gelman ITLC SG strips and eluting with 50% aqueous methanol:10% ammonium acetate (1:1), indicating that 47% protein bound Tc-99m at 15 minutes and 59% at 30 minutes at room temperature. The Tc-99m labeled protein was purified by Centricon-10k filter centrifugation. A sample of 92.4% protein bound Tc-99m showed 84.0% binding to FEMX melanoma cells.

Example 8

Preparation of Re-186 4,5-dimercaptoacetamidopentanoyl-antibody (anti-melanoma antibody 9.2.27).

In an evacuated vial is combined 100 ul of $H_2O$, 100 ul acetonitrile, 100 ul of citric acid solution (28.8 mg, $1.5 \times 10^{-4}$ mol), 50 ul of ligand (tetrafluorophenyl 4,5-di-(tetrahydropyranylmercapto-acetamido)pentanoate (0.40 mg; $6.5 \times 10^{-7}$ mol), 50 ul of stannous chloride (0.5 mg, $2.6 \times 10^{-6}$ mol and 50 ul of Re-186 perrhenate in acetonitrile (4.25 ug, $2.3 \times 10^{-8}$ mol). The mixture is heated at 50° C. for 1 hour, and then 0.30 mL of 1 N NaOH is added.

The tetrafluorophenyl ester product of the Re-186 $N_2S_2$ complex is purified on a $C_{18}$ Baker-10 SPE column. After application to the column, impurities are washed off with $2 \times 3$ mL of $H_2O$ and $4 \times 3$ mL of 10% $CH_3OH/.01$ M phosphate, pH 7. The product is eluted with 2 mL of acetonitrile, and then the solution is reduced to dryness under a stream of nitrogen. Yields of product are about 60%.

Conjugation of Re-186 $N_2S_2$ complex is done by addition of antibody (160 ul of 5 mg/mL) (Morgan, et al., *Hybridoma* (1981) 1:27), in 340 ul of borate buffer (0.5 M, pH 9). After 30 minutes at room temperature, 58% of the radioactivity was protein bound. Immunoreactivity determined by binding of radioactivity to FEMX melanoma cells was 80% after correction for nonprotein bound material.

Example 9

Synthesis of Imidate Form of $N_2S_2$ Ligand, Conjugation
to Antibody and Radiolabeling with Tc-99m.

2,3-(Bis-carbobenzyloxy)diaminopropan-1-ol (2)

A 500 mL hydrogenation bottle was charged with 55 g (0.25 mol) of 2,3-dibromopropanol (Aldrich and 300 mL of 28-30% aqueous $NH_4OH$ solution. The mixture was stoppered with an internal thermometer and heated to 75°-85° C. while shaking on a Parr shaker for 23 hours. When cool, shaking was stopped and the mixture was carefully opened. The mixture was evaporated to a volume of 50 mL by passing $N_2$ gas through it while heating on an oil bath. While hot, 50 mL of EtOH was added and the mixture was allowed to cool. The hydrogen bromide salt of 2,3-diaminopropan-1-ol was collected by filtration and dried in vacuo to yield 50 g of hard chunks of white solid which was used without further purification.

A solution of 25 g of the crude salt in 110 mL of 4 N NaOH was cooled to 0° C. (ice bath, and to the solution was added a solution of 31.4 mL (0.22mol, 37.5 g) of benzylchloroformate in 100 mL of $CH_2Cl_2$. The mixture was stirred rapidly for 30 minutes at 0° C. and 16 hours at room temperature. The $CH_2Cl_2$ phase was collected, washed with 75 mL of brine, dried ($MgSO_4$), filtered and concentrated. The resulting solid was washed with 100 mL of $Et_2O$, collected by filtration and dried in vacuo to give 10.7 g (24%) of 2 as a white solid which could be recrystallized from $CHCl_3$/hexane to give tiny needles. MP 119°-120° C.

2,3-(Bis-carbobenzyloxy)diaminopropyl-1-methanesulfonate (3)

To a suspension of 10.68 g (30 mmol of 2 and 6.27 mL (4.55 g, 45 mmol) of $Et_3N$ in 150 mL of $CH_2Cl_2$ cooled to 0° C. under $N_2$ atmosphere was added 2 55 mL (3.78 g, 33 mmol) of methanesulfonyl chloride, and the mixture was stirred for 30 minutes at 0° C. The resulting clear solution was washed successively with 75 mL of 5% HCl, 75 mL of $H_2O$, 75 mL of 5% $NaHCO_3$ and 75 mL of sat. aq. NaCl (all chilled in ice). The $CH_2Cl_2$ phase was dried ($MgSO_4$, filtered, concentrated and crystallized from $CHCl_3$/hexane to yield 12.33 g (94%) of white crystals. MP 92°-93° C.

3,4-(Bis-carbobenzyloxy)diaminobutyronitrile (4)

A mixture of 6.56 g (15 mmol) of 3, 1.08 g (16.5 mmol) of KCN, 0.40 g (1.5 mmol of 18-crown-6 and 75 mL of anhydrous acetonitrile (stored over 3A molecular sieves) was refluxed in a nitrogen atmosphere for 19 hours. When cool, the mixture was partitioned between 100 mL of 10% $NaHCO_3$ solution and 200 mL of $CH_2Cl_2$. The $CH_2C_{12}$ layer was washed successively with 100 mL portions of 5% HCl, water and brine. The $CH_2C_{12}$ phase was dried ($MgSO_4$, filtered and concentrated to give 5.47 g of brown oil. Two recrystallizations from $CHCl_3$/hexane yielded 2.68 g of 4 as a white solid. MP 111°-112° C.

3,4-Diaminobutyronitrile dihydrogeniodide salt (5)

To 3 38 g 13.3 mmol) of 12 in a 100 mL flask under $N_2$ atmosphere was added 5.42 mL (3.87 g, 26.5 mmol) of hexamethyl-disilane. The mixture was immersed in a 45°-50° C. oil bath until solid 12 dissolved 30 minutes). The temperature was raised to 100° C. and held for 5 minutes until the color disappeared. The solution was cooled to 0° C. with an ice bath and diluted with 13.3 mL of $CH_2Cl_2$. To the 0° C. solution was added dropwise over 5 minutes a solution of 1 96 g (5.3 mmol) of 4 in 13.3 mL of $CH_2Cl_2$. The cooling bath was removed, and the mixture was stirred in the dark for 3 hours at room temperature. To the mixture was added 2 15 mL (1.70 g, 53 mmol) of MeOH, and stirring was continued overnight 16 hours). The mixture was cooled to 0° C., and the solid was collected by filtration and dried in vacuo to give 1.75 g (100%) of a tan solid 5 which was characterized as its dibenzoyl derivative.

3,4-Dibenzoylmercaptoacetamidobutyronitrile (6)

To a mixture of 3.27 g (10 mmol) of 5, 7.33 g (25 mmol) of N-succinimidyl S-benzoylmercaptoacetate and 10 mL of DMF was added at 0° C. under $N_2$ atmosphere, 3.48 mL (2.52 g, 25 mmol) of triethyl amine. The cooling bath was removed, and the mixture was stirred for 1 hour. The mixture was diluted with 50 mL of 5% HCl solution and extracted with $2 \times 50$ mL of $CH_2Cl_2$. The combined $CH_2C_{12}$ phases were washed with 100 mL of 5% $NaHCO_3$ solution, dried ($MgSO_4$, filtered and concentrated in vacuo to yield 6.75 g of a purple tinted solid.

Purification was accomplished by chromatography (silica gel, EtOAc) and crystallization of purified fractions ($CHCl_3$/ hexane) to give 3.20 g 70%) of white solid. MP 125°-127° C.

3,4-Bis-methyldithioacetamidobutyronitrile (7)

To a suspension of 455 mg (1.0 mmol) of 6 in 6 mL of EtOH at room temperature under $N_2$ atmosphere was added 2.2 mL of 1 N aqueous NaOH. The mixture was stirred at room temperature for 1.6 hours, and to the resulting clear solution was added 226 ul of methyl methanethiolsulfonate. The mixture was stirred for 3 hours and partitioned between 20 mL of pH 7-buffer solution and $2 \times 20$ mL of $CH_2Cl_2$. The combined aqueous layers were dried $MgSO_4$, filtered and concentrated to give 591 mg of pink residue. Purification by silica gel chromatography (EtOAc) and crystallization from CHCl$_3$/hexane gave a total of 217 mg (64% of white amorphous solid 7. MP 121°–123° C.

Methyl 3,4-bis-methyldithioacetamidobutyrimidate hydrogen chloride salt (1)

A suspension of 141 mg (0.41 mmol) of 7 in 1.66 mL of MeOH and 4.15 mL of Et$_2$O was cooled to −20° C. (CO$_2$/CCl$_4$), and HCl gas was passed through the mixture via septum inlet for 5 minutes, until most of the solids had dissolved and the solution was saturated with HCl. The mixture was placed in the freezer in a desiccator for 66 hours and then concentrated in vacuo to produce a white foamy solid. The solid was broken up, washed with three portions of anhydrous Et$_2$O, dried in vacuo to give 111 mg (66% of 1 as an off-white solid which decomposed on heating and also decomposed after several days in a freezer.

Preparation of Antibody Methyl 3,4-bis-methyl-dithioacetamidobutyrimidate Conjugate A 2 mg/mL stock solution of the N$_2$S$_2$ ligand was prepared in dry acetonitrile. The solution was standardized by determining the disulfide content using 2-nitro-5-thiosulfobenzoate Thannhauser, et al., Anal. Biochem. (1984) 138:181), and the ligand concentration was found to be 5.30 mM.

For conjugation to mouse monoclonal antibody, 0.16 mL of N$_2$S$_2$ ligand-acetonitrile solution was added to the reaction vial and the solvent removed with a stream of dry nitrogen. Antibody (0.62 mL of 8.1 mg/mL solution) and 1.0 mL of 0.2 M sodium bicarbonate buffer pH 9.5 were mixed and then added to the reaction vessel containing the dried ligand. After stirring 30 minutes at room temperature, the entire solution was added to a fresh vial containing the same amount of dried ligand and the solution stirred another 30 minutes. The conjugated antibody was purified by Sephadex G-25 chromatography in 50 mM sodium phosphate pH 7.5, 0.5 M sodium chloride. The protein-containing fractions were pooled and concentrated in an Amicon stirred cell to a concentration of about 2 mg/mL. The solution was made 50 mM in glutathione, stirred 25 minutes, then purified by Sephadex G-25 gel filtration and concentrated as before. The final solution (1.7 mg/mL) was stored at 4° C. until use.

Radiolabeling of Antibody Methyl 3,4-bis-methyldithioacetamidobutyrimidate Conjugate Tc-99m tartrate was prepared in a total volume of 1.1 mL of degassed water with 100 ug SnCl$_2$, 9% (v/v) ethanol, 75 mg disodium tartrate and 3.2 mCi sodium (Tc-99m) pertechnetate. The solution was heated at 50° C. for 15 minutes. To a separate vial was added 100 ul of the Tc-99m tartrate solution, 100 ul of 0.2 M sodium bicarbonate, pH 10, and 100 ug of the antibody conjugate. The total volume was then adjusted to 0.5 mL with 0.15 M sodium chloride and the solution incubated at 50° C. for 60 minutes. Analysis by HPLC (TSK column, 0.2 M sodium phosphate pH 7.4, 0.15 M sodium chloride) showed 95% of the Tc-99m was associated with the antibody conjugate.

Example 10

Preparation of S-terephthaloyl-substituted N$_2$S$_2$ Ligand.

The mono-tert-butyl ester of terephthalic acid 1 was prepared by the method of Buckle and Smith, J. Chem. Soc. (1971) 54:2821.

Succinimidyl ester 2 was prepared by stirring 1 with 1.2 molar equivalents of N-hydroxysuccinimide and 1.3 molar equivalents of 1,3-dicyclohexylcarbodimide in dry THF at room temperature for 14–16 hours. Thin-layer chromatographic analysis indicated the reaction had gone to completion. The dicyclohexylurea was then removed by filtration, and the resulting liquid was concentrated in vacuo to yield 2 as a white solid. Final purification of 2 was accomplished by flash chromatography.

The thioester 3 was prepared by dissolving 1.0 molar equivalents of mercaptoacetic acid and 2.0 molar equivalents of 4-dimethylaminopyridine in dry THF. The succinimidyl ester 2 was added to the stirring solution. After stirring for 5 hours the reaction was complete as indicated by thin-layer chromatographic analysis. The THF was removed in vacuo, and the residue was dissolved in CH$_2$Cl$_2$. The solution was then washed with dilute aqueous HCl and dried over anhydrous MgSO$_4$. Filtration and evaporation of the solvent gave gas 3 a colorless oil which solidified upon standing.

The succinimidyl ester 4 was prepared by the method of Subramanian (R. F. Schneider, et al., J. Nucl. Med. (1984) 5:223–229).

The carboxylic acid 5 was prepared by dissolving 4,5-diaminopentanoic acid dihydrochloride salt in 1:4 hH$_2$O: CH$_3$CN containing 3.0 molar equivalents of triethylamine and subsequently adding 2.0 molar equivalents of the succinimidyl ester 4. After stirring for 14–18 hours at room temperature, TLC analysis showed the reaction to be complete and the solvent was removed in vacuo. The residue was dissolved in ethyl acetate and washed with dilute aqueous HCl, water and brine. The ethyl acetate layer was then dried over anhydrous Na$_2$SO$_4$. After filtration and removal of the solvent, a waxy solid was obtained which was recrystallized from a mixture of ethyl acetate and hexane to give 5 as a white solid.

Tetrafluorophenyl ester 6A was prepared by dissolving 5, along with 1.2 molar equivalents of 2,3,5,6-tetrafluorophenol in dry THF. 1,3-dicyclohexylcarbodiimide (1.2 molar equivalents) was added to the mixture, and the mixture was stirred for 12–15 hours. Analysis by thin-layer chromatography indicated the reaction was complete. The dicyclohexylurea was removed by filtration, and the solvent was removed in vacuo. The residue was purified by flash chromatography to yield the ester 6A as a white solid.

Succinimidyl ester 6B was prepared by dissolving 5 along with 1.2 molar equivalents of N-hydroxysuccinimide in dry THF. 1,3-dicyclohexylcarbodiimide (1.2 molar equivalents) was added to the mixture, and the mixture was stirred at room temperature for 14–18 hours. Thin-layer chromatographic analysis indicated the reaction had gone to completion. The dicyclohexylurea was removed by filtration, and the solvent was removed in vacuo. The residue was dissolved in ethyl acetate and washed with water. The ethyl acetate solution was dried over anhydrous Na$_2$SO$_4$. The drying agent was removed by filtration, and the solvent was removed in vacuo. The resulting residue was purified by flash chromatography to yield the succinimidyl ester 6B as a white solid.

Removal of the tert-butyl protecting groups was accomplished by dissolving the tetrafluorophenyl ester 6A in CH$_2$Cl$_2$ and treating the solution with excess trifluoroacetic acid, initially at 0° C., then stirring to room temperature for 3 hours. Thin-layer chromatographic analysis showed that the reaction had gone to completion. The solvent and excess trifluoracetic acid were then removed in vacuo to yield a white to colorless solid which was recrystallized from CH₃CN/H₂O to give 7A as a white powder.

In the case of the succinimidyl ester 6B, the tert-butyl protecting groups were removed as described above for compound 6A. It was necessary, however, to purify the product 7B by flash chromatography.

These reaction sequences were also carried out starting with the mono tert-butyl ester of isophthalic acid to obtain the analogous metal isomers of the products described above.

Example 11

Conjugation of N-hydroxysuccinimidyl 4,5-diterephthaloylmercaptoacetamidopentanoate to IgG Antibody.

The conjugation was carried out in a total volume of 2.0 mL and contained 480 ug (7.1×10⁻⁷ moles) N₂S₂ ligand active ester 6B, 0.2 mL redistilled DMF (10%), 0.15 M sodium chloride, 0.05 M sodium borate, pH 8.5, and 10.0 mg mouse monoclonal antibody (6.7×10⁻⁸ moles). After stirring 90 minutes at room temperature the reaction was fractionated by gel filtration over Sephadex G-28 in 0.05 M sodium phosphate buffer pH 7.5 with 0.15 M sodium chloride. The excluded volume containing the conjugated antibody was collected. To remove any residual nonprotein material, the conjugate was dialyzed 18 hours against 0.05 M sodium phosphate, pH 7.5, with 0.15 M sodium chloride. Final yield of protein was 100%.

Example 12

Tc-99ᵐ Labeling of 4,5-diterephthalylmercaptoacetamidopentanoyl-IgG Antibody Conjugate.

To 120 ul saline, 200 ul of 0.2 M sodium phosphate buffer, pH 8, and 80 ul of the terephthaloyl sulfur protected N₂S₂ conjugate (4.66 mg/mL), 250 ul of the Tc-99m tartrate (about 4 mCi) prepared as previously described was added. The reaction mixture was heated at 50° C. for 1 hour, which resulted in a Tc-uptake of 90%.

Following the above procedure, the isophthaloyl analog could also be prepared.

It is important that the resulting product provide for maximum formation of the radionuclide conjugates. In addition, there is the concern about the time, since the radioisotopes do decay with time. Thus, by using the compounds of the subject invention, one can rapidly conjugate proteins to provide radionuclide-substituted reagents for use in vivo. The reagents can be provided in pure form, good yield, and the radionuclide metal is stably maintained as a chelate with the protein for use in vivo. Thus, one can safely direct the radionuclide to a desired site, where only low levels of radioactivity will be nonspecifically directed and bound.

Example 13

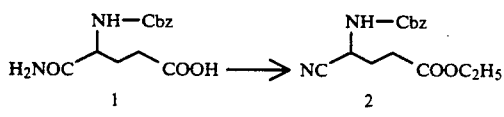

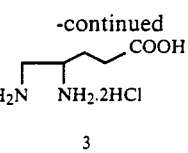

3

Diaminopentanoic Acid.

N-carbobenzyloxyisoglutamine was prepared according to the procedure of R. Struka and M. Zaoral. *Collection of Czechoslav. Chem. Comm.* (1977) 42:560.

N-Carbobenzyloxyisoglutamine Ethyl Ester (1)

A stirred suspension of carbobenzyloxyisoglutamine (28 g, 100 mmol) and p-toluenesulfonic acid monohydrate (1.9 g, 10 mmol) in 560 mL of absolute ethanol was gently refluxed for 12-14 hours or until TLC (1:5:94 HOAc/H₂/CH₃CN) indicated that the reaction was complete.

The reaction mixture was concentrated in vacuo and recrystallized from ethyl acetate/hexane to give a white solid: mp 144°-145° C.

N-Carbobenzyloxy-γ-cyano-γ-aminobutyric Acid Ethyl Ester (2)

To a stirred suspension of Cbz-isoglutamine ethyl ester (15.42 g, 50 mmol and pyridine (8.48 mL, 105 mmol) in 360 mL of anhydrous THF at 0° C. was added dropwise a solution of trifluoroacetic anhydride (7.77 mL, 55 mmol) in 40 mL of THF, at such a rate to maintain a temperature of 0°-5° C. for 1-2 hours or until reaction was complete as evidenced by TLC (5% H₂O/94% CH₃CN/1% HOAc; Cu(OAc)2 stain.

The reaction mixture was concentrated in vacuo to a clear oil. The oil was taken up in ethyl acetate, washed twice with dilute aqueous HCl, once with water, once with brine, and dried over Na₂SO₄. The mixture was filtered and concentrated in vacuo to a clear oil. Recrystallization from cold ethanol/water gave 11.90 g 82%) of white needles: m.p. 61°-62° C.

4,5-Diaminopentanoic Acid Dihhdrogen Chloride (3)

A 500 mL Parr Shaker bottle was charged with 3.0 g of N-carbobenzyloxy-cyano-amino-butyric acid ethyl ester, 500 mg of PtO₂ catalyst (Aldrich), 80 mL of EtOH and 80 mL of 6 N HCl. The mixture was shaken for 16 hours under 50-60 psi H₂ pressure. The mixture was filtered and concentrated. The resulting oily residue was dissolved in 150 mL of 6 N HCl and heated at 70° C. for 4 hours. The mixture was concentrated in vacuo, and to the resulting syrup was added 100 mL of EtOH. The mixture was allowed to stand in the refrigerator, and the resulting solid was collected by filtration to yield approximately 2 g of 3 as a white powder.

S-(1-ethoxyethyl)mercaptoacetic acid (5a)

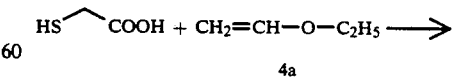

4a

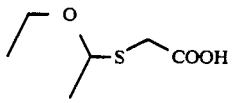

5a

A solution of mercaptoacetic acid (17.4 mL, 250 mmol) in 125 mL of dichloromethane containing p-toluenesulfonic acid monohydrate (0.24 g, 1.26 mmol) was cooled to −18° to −25° C. with stirring. Ethyl vinyl ether (23.9 mL, 250 mmol) in 125 mL of dichloromethane was added dropwise to the cold solution over a period of 90 minutes. The stirring was continued for an additional 30 minutes with the temperature maintained in the −18° to −25° C. range. Then 200 mL of pH=7 phosphate buffer was added, and the reaction mixture was allowed to warm with stirring for 10 to 15 minutes. The mixture was then poured into a flask containing 900 mL of ethyl acetate and 200 mL of water. Layers were separated and the aqueous portion extracted twice with ethyl acetate. The organic layers were combined, washed with brine and dried (MgSO$_4$. Removal of the solvent left 31.4 g of S-(1-ethoxyethyl mercaptoacetic acid 4 as a colorless oil 77% yield): $^1$H NMR (CDCl$_3$) 1.15(t,J−7.0Hz,3H), 1.52(d,J=6.4Hz,3H , 3.36(s,2H), 3.60(m,2H),4.84(q,J=6.4Hz,1H), 11.65(s,1H). The material was used without further purification.

In similar reactions, mercaptoacetic was reacted with 4b and 4c to give 5b and 5c.

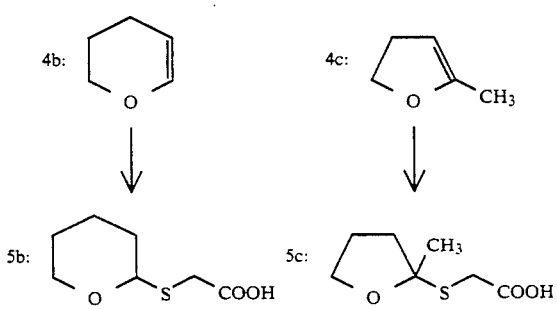

S-(Tetrahydropyran yl mercaptoacetic acid

A solution of mercaptoacetic acid (1.4 mL, 20.0 mmol) in 3,4-dihydro-2H-pyran was cooled to 0° C. with stirring. A catalytic amount (20 mg of p-toluenesulfonic acid monohydrate was cautiously added, and the mixture was allowed to stir at 0° C. for 30 minutes, then to room temperature for 1 hour. The excess 3,4-dihydro-2H-pyran was removed in vacuo to leave an oily residue. The residue was dissolved in tetrahydrofuran containing 2 mL of 1.0 N aqueous HCl and allowed to stir at room temperature for 20 minutes. The tetrahydrofuran was evaporated, and the residue was dissolved in ethyl acetate. The ethyl acetate solution was extracted with 5% aqueous sodium bicarbonate. The bicarbonate extracts were combined and washed with ethyl acetate. Fresh ethyl acetate was added to bicarbonate extracts, and the aqueous layer was acidified to pH 1 with 1.0 N aqueous HCl. The layers were separated, and the aqueous portion was extracted twice with ethyl acetate. The organic layers were combined and dried (MgSO$_4$). Removal of the solvent afforded 3.28 g of 5b as a viscous oil (93% yield): 1H NMR(CDCl3) 1.68(b,6H), 3.34(m,2H), 3.62(m,1H), 3.90(m,1H), 5.05(b,1H , 11.5(s,1H). The material was used without further purification.

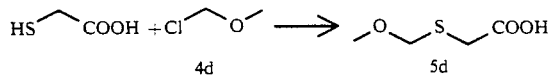

S-Methoxymethyl-mercaptoacetic acid (5d)

To a solution of 1.40 mL (1.84 g, 20 mmol) mercaptoacetic acid and 8.36 mL (6.07 g, 60 mmol) of triethylamine in 25 mL of DMF at 0° C. was added dropwise, over 2 minutes, 3.34 mL (3.54 g, 44 mmol) of chloromethyl methyl ether. The mixture was allowed to come to room temperature and stirred for 16 hours. The mixture was partitioned between 50 mL of Et$_2$O and 50 mL of H$_2$O. The Et$_2$O layer was washed in succession with 50 mL of 5% HCl solution, 50 mL of pH 7 buffer and 50 mL of saturated NaCl solution. The Et$_2$O layer was concentrated in vacuo, and the residual oil was dissolved in 20 mL of THF and mL of 6 N HCl solution. The mixture was stirred for 3 hours and partitioned between 50 mL of saturated NaCl solution and mL of Et$_2$O. The Et$_2$O layer was dried (MgSO$_4$), filtered and concentrated to yield 1.53 g (56%) of 5d which was pure enough to use in the next step: $^1$H NMR (CDCl3 3 33(s,2H , 3.38(s,3H), 4.72(s,2H , 10.01(brd s,1H).

In a similar manner, 2-methoxyethyl chloromethyl ether (4d) was reacted with mercaptoacetic acid to give S-(methoxyethoxy)methylmercaptoacetic acid (5d) in 58% yield as an oil.

Succinimidyl S-(1-ethoxyethyl)mercaptoacetate

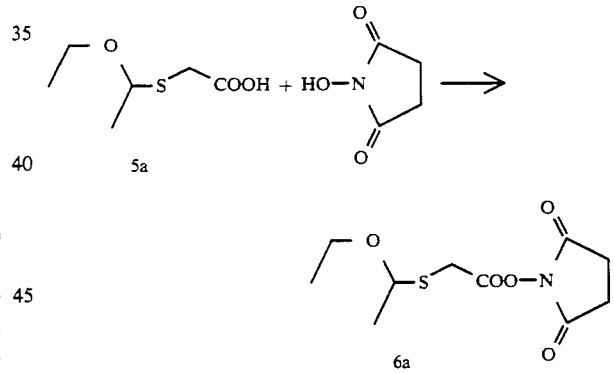

A solution of S-(1 ethoxyethyl )mercaptoacetic acid 5.76 g, 35.1 mmol) and N-hydroxysuccinimide 4.85 g, 42.1 mmol) was prepared in 100 mL of anhydrous THF. To this was added a solution of 1,3-dicycloherylcarbodiimide (8.70 g, 42.1 mmol) in mL of anhydrous THF. The mixture was stirred at room temperature for 2 hours or until TLC analysis indicated complete formation of the succinimidyl ester. The mixture was then filtered, and the filtrate was concentrated in vacuo to a viscous residue. The residue was dissolved in ethyl acetate, washed with water, brine, and dried (MgSO$_4$). Removal of the solvent left the crude succinimidyl ester as an oil, which was further purified by flash chromatography on silica gel, using ethyl acetate-hexanes as the column eluent, to give 5.1 g of S-(1-ethoxyethyl)-mercaptoacetic acid succinimidyl ester as a colorless oil (56% yield): $^1$H NMR (CDCl$_3$) 1.21(t,J=7.0Hz,3H), 1.58(d,J=6.4Hz,3H), 2.83(s,4H), 3.60(m,4H), 4.88(q,J=6.4Hz,1H).

In a similar manner, compounds 6b–6e were prepared.

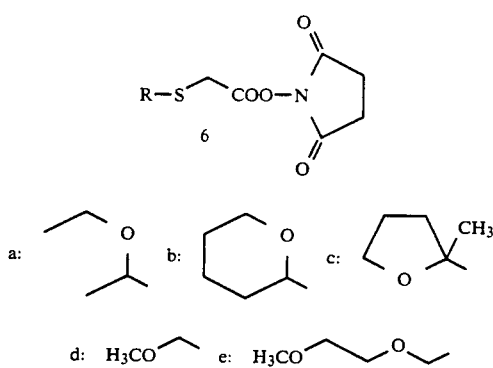

Synthesis of 4,5-Bis[S-(1ethoxyethyl)thioacetamido] Pentanoic Acid

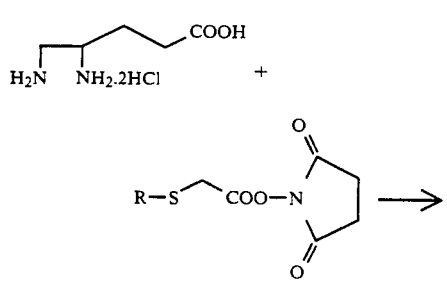

R =

6a

To a stirring suspension of 4,5-diaminopentanoic acid dihydrochloride (1.64 g, 8.0 mmol) in 32 mL of anhydrous dimethylformamide containing triethylamine (6.7 mL, 48.0 mmol) was added S-(1-ethoxyethyl)mercaptoacetic acid succinimidyl ester 4.60 g, 17.6 mmol) dissolved in 12 mL of anhydrous dimethylformamide. The reaction mixture was stirred at room temperature for 90 minutes or until TLC analysis indicated complete formation of 4,5-bis[S-(1-ethoxyethyl)thioacetamido] pentanoic acid. Then the reaction mixture was filtered, and the filtrate was concentrated to a viscous oil. The oil was dissolved in ethyl acetate and washed with successive portions of water until no N-hydroxysuccinimide was evident in the organic phase by TLC. The organic phase was washed with brine and dried (MgSO$_4$). Removal of solvent afforded 2.0 g of 4,5-bis[S-(1-ethoxyethyl)thioacetamido]pentanoic acid as a viscous oil which solidified upon trituration with ether (59% yield): $^1$H NMR (CDCl$_3$) 1.18(t,J=7.2Hz,6H), 1.53(d,J=6.6Hz,6H), 1.88(m,2H), 2.45(t,J=6.8Hz,2H), 3.30(s,4H), 3.55(m,6H), 4.10(m,1H), 4.77(q,J=6.6Hz,2H), 7.33(m,2H), 9.44(br,1H).

In a similar manner, compounds 7b and 7e were prepared.

Synthesis of 2,3,5,6-tetrafluorophenyl-4,5-bis-[S-(1ethoxyethyl)thi-oacetamido]pentanoate To a solution of 4,5-bis[S-(1-ethoxyethyl)thioacetamido] pentanoic acid (1.50 g, 3.53 mmol) and 2,3,5,6-tetrafluorophenol (0.88 g, 5.3 mmol) in 16 mL of anhydrous tetrahydrofuran was added 1,3-dicyclohexylcarbodiimide (0.95 g, 4.6 mmol) with rapid stirring. The mixture was stirred at room temperature for 18 to 24 hours or until TLC analysis indicated complete conversion to the ester. Then the mixture was filtered, and the filtrate was concentrated to give a solid. The solid was dissolved in a minimal amount of ethyl acetate and allowed to stand at 5° C. for 2 hours. The solution was then filtered to remove any precipitated dicyclohexylurea, and the filtrate was concentrated to afford solid 2,3,5,6-tetrafluorophenyl-4,5-bis[S-(1-ethoxyethyl)thioacetamido]pentanoate. The solid was washed with ether to remove any remaining 2,3,5,6-tetrafluorophenol. After drying in vacuo, 1.64 g of 2,3,5,6-tetrafluorophenyl-4,5-bis[S-(1-ethoxyethyl) thioacetamido]pentanoate was obtained (81% yield). $^1$H NMR (CDCl$_3$) 1.22(t,J=7.2Hz,6H), 1.56(d,J=6.6Hz,6H), 2.06(m,2H), 2.83(t,J8HZ,2H), 3.33(s,4H , 3.60(m,6H), 4.15(m,1H), 4.75(q,J=6.6Hz,2H), 7.22(m,3H).

In a similar manner, the 2,3,5,6-tetrafluorophenyl esters of 7b–7e were prepared.

The 2-fluorophenyl (8a), 4-fluorophenyl (9a), 2,4-difluorophenyl (10 , 2-pyrrolidone (11a), succinimidyl (12a), 2,3,5,6-tetrafluorothiophenyl (13a) esters were synthesized by the same method, except that the final purification was achieved by flash chromatography.

The N,N-diethylamino ester 14a) was prepared by the
established isobutylchloroformate mixed anhydride method (*The Peptides*, Vol.1, Ch.6, Johannes Meinhofer, Academic Press, 1979 and "The Practice of Peptide Synthesis," *Reactivity and Structure: Concepts in Organic Chemistry*, Vol.21, pp.113–115, Springer-Verlog, 1984).

The cyanomethylester 15a) was also prepared by established method (*The Peptides*, Vol.1, Ch.6, Johannes Meinhofer, Academic Press, 1979 and "The Practice of Peptide Synthesis," *Reactivity and Structure: Concepts in Organic Chemistry*, Vol.21, pp.109–110, Springer-Verlog, 1984).

Compound 16 was synthesized as follows:

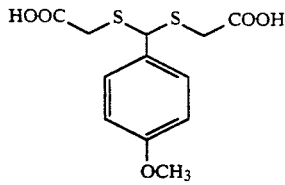

A solution of mercaptoacetic acid (13.9 mL, 200 mmol) and p-anisaldehyde (12.2 mL, 100 mmol) was prepared in 250 mL of dichloromethane. To this was slowly added boron trifluoride etherate (1.0 mL, 8.1 mmol) at room temperature with stirring. The reaction mixture was stirred at room temperature for 8 hours, at which point some of the product 16 had precipitated. Removal of the solvent left 16 as a white solid. The solid was collected and washed with portions of dichloromethane. Drying in vacuo left 19.1 g of 16 as a white solid (63% yield): $^1$H NMR (d6DMSO) 3.24(s,2H , 3.30(s,2H , 3.72(s,3H), 5.24(s,1H), 6.82-7.41(m,4H), 10.40(b,2H).

Preparation of the bis-succinimidyl Ester (17)

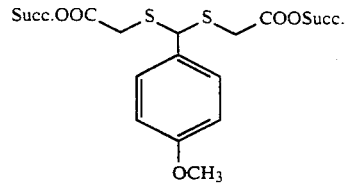

A solution of (4-methoxyphenyl)methanedithiol-S,S'-diacetic acid 16 (10.0 g, 33.1 mmole) and N-hydroxysuccinimide (8.37 g, 72.7 mmol) was prepared in 300 mL of anhydrous tetrahydrofuran. To this was added a solution of 1,3-dicyclohexylcarbodiimide (15.0 g, 72.7 mmole) in 128 mL of anhydrous tetrahydrofuran. After stirring at room temperature for about 4 hours, the reaction mixture was filtered to remove the dicyclohexylurea by-product of the reaction. Removal of the solvent from the filtrate left a white solid. Recrystallization from acetonitrile gave 10.24 g of bis-succinimidyl-(4-methoxyphenyl) methanedithio-S,S'-diacetate 17 (62% yield): 1H NMR (d6DMSO) 2.84(s,8H), 3.74(m,7H), 5.42(s,1H), 7.18(m,4H).

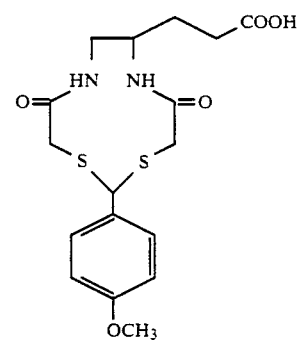

Preparation of (18)

A solution of 4,5-diaminopentanoic acid dihydrochloride (0.601 9, 2.93 mmol) in 58% mL of N,N-dimethylformamide and a solution of bis-succinimidyl-(4-methoxyphenyl ) methanedithiol-S,S'-diacetate (1.46 9, 2.93 mmol) in 290 mL of N,N-dimethylformamide were added simultaneously and dropwise to a solution of triethylamine (0.82 mL, 5.88 mmol ) in 290 mL of N,N-dimethylformamide with rapid stirring over a period of 30 minutes at room temperature. The mixture was then stirred for 4 hours. Removal of the solvent left an oil which was dissolved in ethyl acetate, washed with water and with brine, and dried (MgSO$_4$). Removal of the solvent left a solid. The solid was triturated with ether and collected by filtration. The solid was washed with ether and dried to give 0.91 g of 18 as a white solid (79% yield): $^1$H NMR (d6-DMSO) 1.68(m,2H), 2.30(m,2H , 3.20(m,7H), 3.78(s,3H), 5.04(s,1H), 7.20(m,4H), 7.94(b,2H). MS(EI), m/e 398(M+), 380(M+-H$_2$O).

Preparation of 2,2-propanedithio-S,S'-diacetic Acid (19)

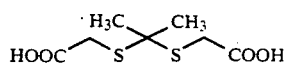

Acid-catalyzed condensation of 2-methoxypropene with mercaptoacetic acid by a method similar to the preparation of S-(1-ethoxyethyl)mercaptoacetic acid (5a) afforded 2,2-propanedithiol-S,S'-diacetic acid as a white crystalline solid in low yield: $^1$H NMR (d$_6$-DMSO) 1.54(s,3H), 3.38(s,2H).

O,O'-bis-succinimidyl(S,S'-isopropylidine)-S,S'-diacetic Acid (20)

To a solution of 897 mg (4.0 mmol) of 19 and 1.01 g (8.8 mmol) of N-hydroxysuccinimide in 20 mL of THF at 0° C. was added 1.81 g (8.8 mmol) of 1,3-dicyclohexylcarbodiimide. The mixture was stirred at 0° C. for 1 hour and at room temperature for 2 hours. The white solids were removed by vacuum filtration, and the filtrate was concentrated to a white solid solution was filtered again, and the filtrate was concentrated to give an oily solid. Recrystallization of the oily solid gave 1.22 g (73%) of a white solid: $^1$H NMR (CDCl$_3$) 1.74(s,6H), 2.89(s,8H), 3.75(s,4H).

S,S'-acetonyl-4,5-bis(thioacetamido) pentanoic acid (20)

To a solution of 205 mg (1 mmol) of 4,5-diaminopentanoic acid dihydrochloride and 557 ul (405 mg, 4 mmol of Et$_3$N in 100 mL of DMF was added over 40 minutes a solution of 224 mg (1 mmol of 19 in 100 mL of DMF. The mixture was stirred for 2 hours and concentrated to a viscous oil in vacuo. Purification by silica gel chromatography yielded an oil which was triturated with ether. The resulting white solid was collected by vacuum filtration to yield 68 mg (21%) of white powder: $^1$H NMR (CD$_3$OD 1 78(s,6H), 1 62-2.00(m,2H , 2.14-2.63(m,2H , 3 29(s,4H), 3.00-3.50 (m,2H), 3.78-4.35(m,1H), 7.30-8.00(bid,2H).

Example 14

Conjugation of Chelates Comprising Esters to an Antibody.

Chelate compounds of the invention comprising various ester groups were conjugated to an antibody. The six chelating compounds tested had the formula:

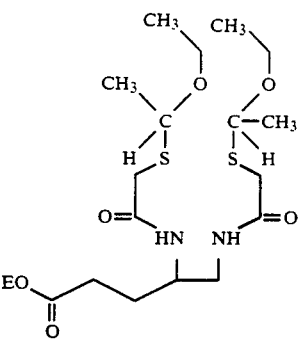

wherein E represents the leaving group of an ester, chosen from o-fluorophenyl; p-fluorophenyl; 2,4-difluorophenyl; 2,3,5,6-tetrafluorophenyl; cyanomethyl; and N-hydroxypyrrolidone groups. The sulfur-protecting groups shown are ethoxyethyl groups. These compounds were prepared as described above. Each of the six compounds was radiolabeled, to form the chelate, as follows:

To 100 ul of a solution containing 5 mg of sodium gluconate and 0 1 mg of SnCl$_2$ in water, 500 ul of $^{99m}$TcO$_4$-(pertechnetate) was added. After incubation at room temperature for 10 minutes to form a Tc-gluconate complex, 100 ul of the chelating compound (dissolved in IPA/AA 90:10, a 1 mg/mL solution), 80 ul of 0.2 N HCl and 200 ul of isopropyl alcohol were added, in that order. The reaction mixture was heated at 75° C. for 15 minutes, then cooled on ice for 5 minutes. Next, 100 ul of 1.0 M sodium bicarbonate buffer or phosphate buffer were added, wherein the pH of the added buffer was such that the pH during the following protein conjugation step was as shown in Table 3 for each of the reactions. Next, 400 ul of a 5 mg/mL buffered solution of an antibody was added, followed by addition of 300 ul of the same buffer. The antibody was a monoclonal antibody designated 9.2.27, which is specific for an antigen which is a 250 kilodalton glycoprotein/proteoglycan complex associated with human melanoma cells. This monoclonal antibody has been described by Morgan, et al., *Hybridoma*, 1:17 (1981). The reaction mixtures were incubated at room temperature for either 15 minutes, 30 minutes or 1 hour, as shown in Table 3. The percentage of the ester-containing chelate in each reaction mixture which was conjugated to the antibody was determined by standard instant thin-layer chromatography (ITLC) in 12% TCA. ITLC is a known procedure, generally described in *Nuclear Medicine Technology and Techniques*, ed. Bernier, D., Longan, J., and Wells, L.; The C. V. Mosby Co., St. Louis, 1981; pp.172-174. The procedure is described in more detail in Example 15. The results are shown in Table 3.

TABLE 3

| ESTER | YIELD (% PURITY) HPLC | YIELD (% PURITY) ITLC | PH DURING CONJUGATION | % CONJUGATION AT ROOM TEMPERATURE 15 MIN | 30 MIN | 1 HR |
|---|---|---|---|---|---|---|
| o-fluorophenyl | 96 | 87/22 | 9.94 | 18 | 17 | 22 |
| p-fluorophenyl | 99 | 94/10 | 9.90 | 11 | 16 | 11 |
| 2,4-difluorophenyl | 96 | 93/7 | 9.80 | 13 | 14 | 14 |
| 2,3,5,6-tetrafluorophenyl | 90 | 86/14 | 9.88 | 49 | 51 | 50 |
| cyanomethyl | 98 | 82/14 | 10.0 | 17 | 15 | — |
| | 97 | — | 8.7 | 19 | 14 | — |
| | 98 | — | 7.5 | 21 | 38 | — |
| | 97 | — | 6.8 | 9 | 10 | — |

TABLE 3-continued

| ESTER | YIELD (% PURITY) | | PH DURING CONJUGATION | % CONJUGATION AT ROOM TEMPERATURE | | |
|---|---|---|---|---|---|---|
| | HPLC | ITLC | | 15 MIN | 30 MIN | 1 HR |
| | 97 | — | 6.3 | 20 | 15 | — |
| N-Hydroxy | 88 | 67 | 10.0 | 22 | 22 | — |
| Pyrrolidone | 81 | — | 8.7 | 22 | 22 | — |
| (NHP) | 88 | — | 7.7 | 15 | 14 | — |

Example 15

Diagnostic Kit.

Figure 1C:
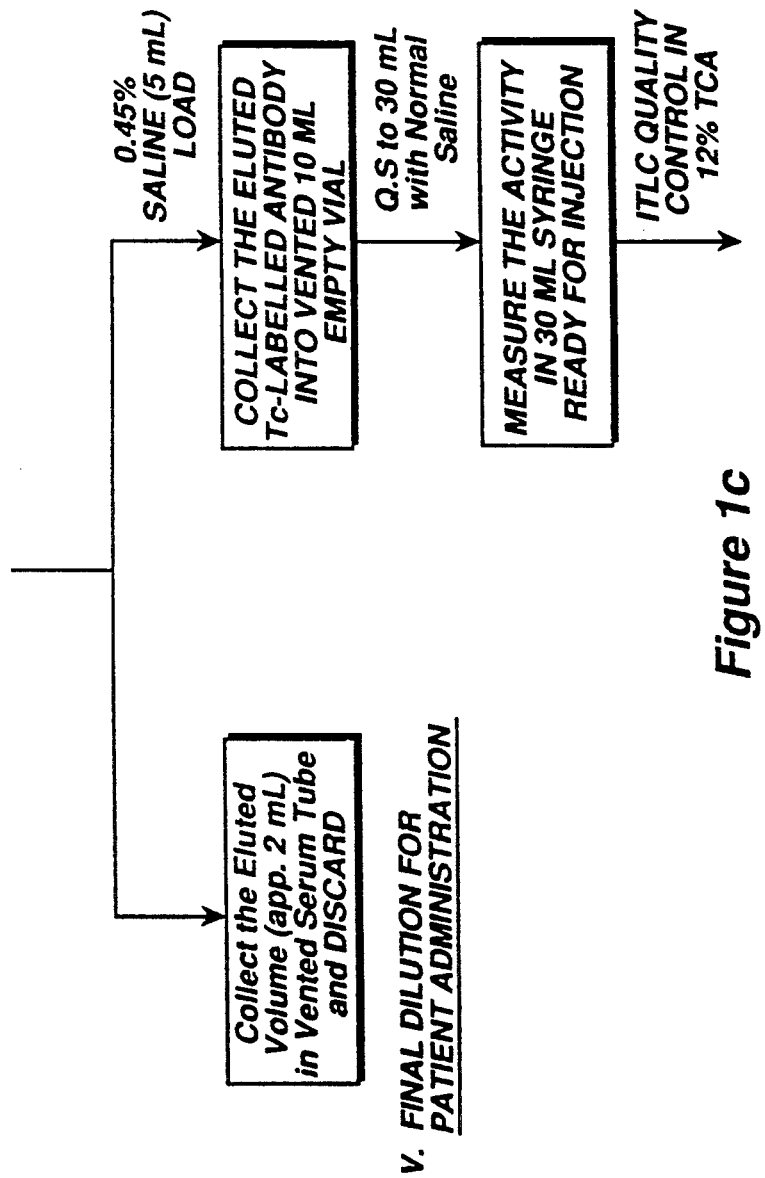

A diagnostic kit containing reagents for preparation of a $^{99m}$Tc-radiolabeled protein conjugate was used as follows, and as outlined in FIG. 1. The procedures were conducted under conditions which ensured the sterility of the product (e.g., sterile vials and sterilized reagents were used where possible, and reagents were transferred using sterile syringes). All of the reagents, buffers and solutions shown on the flow chart were components of the kit. Proper shielding was used once the radioisotope was introduced.

One mL of sterile water for injection was added to a sterile vial containing a stannous gluconate complex (50 mg sodium gluconate and 1.2 mg stannous chloride dihydrate, available from Merck Frosst, Canada, in dry solid form) and the vial was gently agitated until the contents were dissolved. A sterile insulin syringe was used to inject 0.1 mL of the resulting stannous gluconate solution into an empty sterile vial. Sodium pertechnetate 0.75 mL, 75-100 mCi, eluted from a $^{99}$Mo/$^{99}$Tc generator purchased from DuPont, Mediphysics, Mallinckrodt or E. R. Squibb) was added, and the vial was agitated gently to mix the contents, then incubated at room temperature for 10 minutes to form a $^{99m}$Tc-gluconate complex.

In an alternative procedure for providing the $^{99m}$Tc-gluconate exchange complex, the kit includes a vial containing a lyophilized preparation comprising 5 mg sodium gluconate, 0.12 mg stannous chloride dihydrate, about 0.1 mg gentisic acid as a stabilizer compound, and about 20 mg lactose as a filler compound. The amount of gentisic acid may vary, with the stabilizing effect generally increasing up to about 0.1 mg. Interference with the desired reactions may occur when about 0.2 mg or more gentisic acid is added. The amount of lactose also may vary, with amounts between 20 and 100 mg, for example, being effective in aiding lyophilization. Addition of stabilizer and a filler compound is especially important when the vial contained these relatively small amounts of sodium gluconate and stannous chloride (compared to the alternative embodiment above). One mL of sodium pertechnetate (about 100 mCi) was added directly to the lyophilized preparation. The vial was agitated gently to mix the contents, then incubated as described above to form the $^{99m}$Tc-gluconate complex.

A separate vial containing 0.3 mg of a chelating agent in dry solid form was prepared by dispensing a solution of 0.3 mg chelating agent in acetonitrile into the vial, then removing the solvent under N$_2$ gas, and the resulting vial containing the chelating compound was provided in the kit. To this vial was then added 0.87 mL of 100% isopropyl alcohol, and the vial was gently shaken for about 2 minutes to completely dissolve the chelating agent, which was 2,3,5,6-tetrafluorophenyl 4,5-bis[S-(1-ethoxyethyl)thioacetamido]pentanoate, the structure of which is represented by the formula in Example 14, when E is a 2,3,5,6-tetra-fluorophenyl group. Next, 0.58 mL of this solution of the chelating agent was transferred to a vial containing 0.16 mL of glacial acetic acid/0.2 N HCl (2:14), and the vial was gently agitated. Of this acidified solution, 0 5 mL was transferred to the vial containing the $^{99m}$Tc-gluconate complex, prepared above. After gentle agitation to mix, the vial was incubated in a 75° C.±2° C. water bath for 15 minutes, then immediately transferred to a 0° C. ice bath for 2 minutes.

To a separate vial containing 10 mg of the F(ab) fragment of a monoclonal antibody (specific for the above described 250 Kd glycoprotein/proteoglycan melanoma-associated antigen) in 0.5 mL of phosphate-buffered saline, was added 0.37 mL of 1.0 M sodium bicarbonate buffer, pH 10.0. the F(ab) fragment was generated by treating the monoclonal antibody with papain according to conventional techniques. The monoclonal antibody, designated NR-ML-05, recognizes an epitope on the 250 Kd antigen which is different than the epitope recognized by the above-described monoclonal antibody designated 9.2.27. The vial was gently agitated.

The vial containing the acidified solution of the $^{99m}$Tc-labeled chelate (see above) was removed from the ice bath, 0.1 mL of the sodium bicarbonate buffer was added, and the vial was agitated to mix. Immediately, the buffered antibody solution (above) was added, gently agitated to mix and incubated at room temperature for 20 minutes to allow conjugation of the radiolabeled chelate to the antibody.

A column containing an anion exchanger, either DEAE-Sephadex or QAE-Sephadex, was used to purify the conjugate. The column was prepared under aseptic conditions as follows. Five 1 mL QAE-Sephadex columns were connected end-to-end to form a single column. Alternatively, a single 5 mL QAE Sephadex column may be used. The column was washed with 5 mL of 37 mM sodium phosphate buffer, pH 6.8. A 1.2u filter (available from Millipore) was attached to the column, and a 0.2u filter was attached to the 1.2u filter. A 22-gauge sterile, nonpyrogenic needle was attached to the 0.2u filter.

The reaction mixture was drawn up into a 3 mL or 5 mL syringe, and any air bubbles were removed from the solution. After removal of the needle, the syringe was connected to the QAE-Sephadex column on the end opposite the filters. The needle cap was removed from the 22-gauge needle attached to the filter end of the column and the needle tip was inserted into a sterile, nonpyrogenic test tube. Slowly, over 2 minutes, the reaction mixture was injected into the column. The eluant collected in the test tube was discarded. The now empty syringe on top of the column was replaced with a 5 mL syringe containing 5 mL of 75 mM (0.45%) sodium chloride solution (from which air bubbles had been removed). The needle at the other end of the column was inserted aseptically into a sterile, nonpyrogenic 10 mL serum vial. Slowly, over 2 minutes, the NaCl solution was injected-into the column, and the eluent was collected in the serum vial.

The total radioactivity in the serum vial was measured using a dose calibrator. In two separate kit preparations, the yield of radiolabeled antibody was 57.2% and 60.9%, respectively; and the yield generally ranges from about 45% to 65%. The contents of the serum vial were drawn up into a sterile, pyrogen-free, 30cc syringe and diluted to a total volume of 30 mL with sterile 0.9% NaCl for injection into a human melanoma patient. A quality control test was performed on a 0.01 mL aliquot before injection by instant thin layer chromatography, as follows.

Supplies

1 Chromatographic Solvent. Prepare a 12% (w/v) trichloroacetic acid (TCA) in water solution. The solvent can be prepared as a stock reagent and is stable for 30 days when stored at 4° C.

2. Silica Gel Impregnated Glass Fiber Sheets. These are available from Gelman Sciences, Inc., Ann Arbor, Michigan, as ITLC$^{TM}$ SG, 20×20 sheets, Product No. 61886. Pre-cut the strips to a final dimension of 2×10 cm. NOTE: The strips are fragile; use caution during handling. Activate the pre-cut strips according to the manufacturer's instructions. Store the activated strips after activation according to the manufacturer's instructions.

Test Procedure

1. An activated TLC chromatographic strip was carefully removed from a storage container using forceps. Using a lead pencil, the origin was carefully marked with a lead pencil at approximately 1.2 cm from one end of the strip.

2. A small drop (2–5 uL) of product was spotted at the origin. NOTE: It is not necessary to dry the spot prior to beginning chromatographic developing.

3. The chromatographic strip was then placed into the developing chamber, with care taken not to immerse the origin into the solvent bath.

4. The chromatographic strip was developed, allowing the solvent to ascend to about 1 cm from the strip top. The strip was then removed from the developing chamber and allowed to dry.

5. The developed chromatographic strip was cut into three sections as illustrated below, and the sections were identified as origin, middle and solvent front.

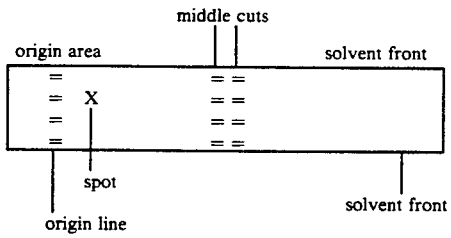

Using the developing system described above, technetium Tc-99m labeled antimelanoma antibody or fragments thereof remain at the origin, and nonprotein-bound Technetium-99m labeled material travels with the solvent front. The middle section of the chromatographic strip may be used to verify complete separation between product and impurity (less than 5% of total Technetium-99m activity should be assayed on this section of the strip).

6. Using a suitable radioactivity counter (e.g., a gamma counter calibrated for $^{99m}$Tc), each section of the strip was counted. If a radioactive counter is used, continue counting long enough to determine a statistically significant net count for each strip section.

7. The radiochemical purity (percent Technetium-99m antimelanoma antibody) was calculated using the following formula:

$$\frac{\text{Net Counts Origin Area}}{\text{Net Counts Solvent + Net Counts Middle Section + Net Counts Origin Area}} \times 100\%$$

If the radiochemical purity is less than 85%, the material should not be injected into a human patient. Using this procedure, radiochemical purities generally range from about 90% to 99%. The total amount of radioactivity also was measured prior to injection. In general, from 10 to 30 mCi will be administered to a human patient.

Prior to administering the radiolabeled F(ab) fragment (the diagnostic radiolabeled antibody fragment), an irrelevant antibody and an unlabeled specific antibody were administered to the patient to improve the diagnostic images, as described above. The irrelevant antibody, provided in a separate vial in the kit, was a whole murine monoclonal antibody directed against a B-cell lymphoma idiotype. The unlabeled specific antibody, also provided in the kit, was a whole antimelanoma monoclonal antibody designated NR-ML-05, described above. Both the irrelevant antibody and the unlabeled specific antibody were administered as described in Example 17.

The entire 30 mL sample containing the radiolabeled antibody fragment was administered to a patient by intravenous infusion. The infusion was completed in from about 5 minutes to about 15 minutes. The antibody fragment concentration in the sample was 0.33 mg/mL.

Target melanoma sites were detected in the patient. The imaging procedure, using a gamma camera, was as described in Example 17, in which patient No. 8501.35 received a radiolabeled diagnostic antibody fragment prepared using a kit according to the invention.

Example 16

Therapeutic Kit: Preparation of Re-188 Labeled Conjugates.

Figure 2B:
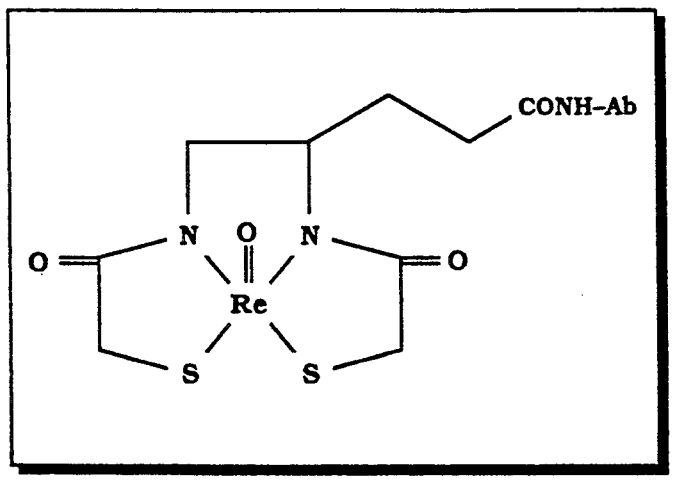
FIG. 2 (a-e) is a flow chart representing the preparation of a polypeptide radiolabeled with a rhenium isotope using a kit in accordance with one embodiment of the invention.
Figure 2C:
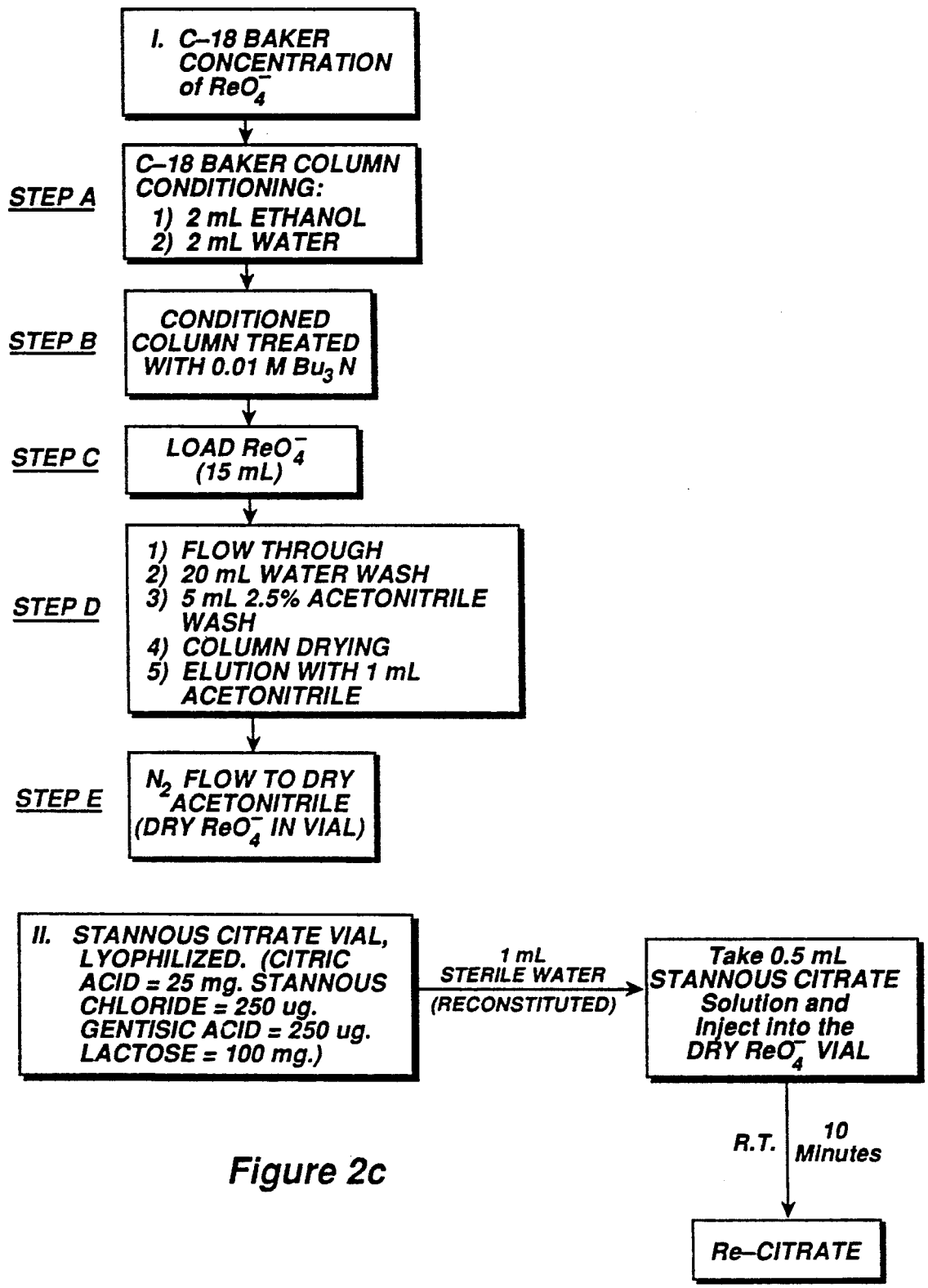
Figure 2E:
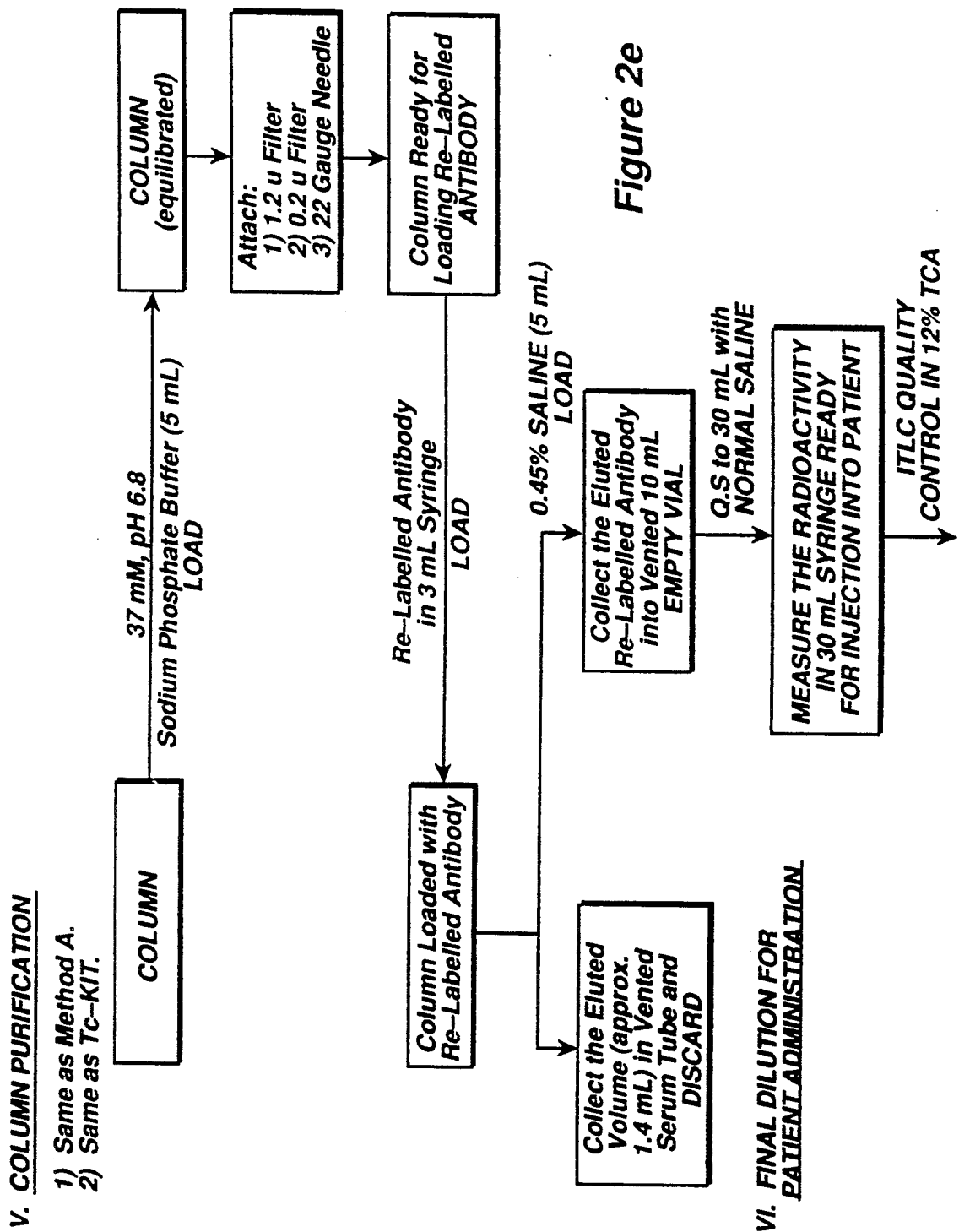

A therapeutic kit containing reagents for preparation of a $^{188}$Re-radiolabeled protein conjugate was used as follows, and as outlined in FIG. 2.

Sodium perrhenate (3 mL, 15 mCi, produced from a W-188/Re-188 research scale generator) was added to a vial containing a lyophilized mixture comprising citric acid, 75 mg; stannous chloride, 0.75 mg; gentisic acid, 0.25 mg; and lactose, 100 mg. The vial was agitated gently to mix the contents, then incubated at room temperature for 10 minutes to form a $^{188}$Re-citrate exchange complex. To a separate vial containing 0.50 mg of 2,3,5,6-tetrafluorophenyl-4,5-bis[S-(1-ethoxyethyl thioacetamido]pentanoate (a C5 N$_2$S$_2$ chelating agent of the invention comprising ethoxyethyl S-protective groups and a 2,3,5,6-tetrafluorophenyl ester group, 0.50 mL of isopropyl alcohol was added and the vial was agitated for 2 minutes to completely dissolve the chelating agent. Next, 0.30 mL of this solution was transferred to the vial containing the $^{188}$Re-citrate complex prepared above. After gentle mixing, the vial was incubated in a 75° C.±2° C. water bath for 15 minutes, then immediately transferred to a 0° C. ice bath for 2 minutes. The yields of $^{188}$Re-labeled chelate then ranged between 75% and 90% as measured by reversed phase $C_{18}$ HPLC analysis. H A column containing a $C_{18}$ reversed phase low-pressure 1 material (Baker $C_{18}$ cartridges) was used to purify the $^{188}$Re-labeled chelate. After conditioning of the cartridge with ethanol and water, the sample was loaded and washed with three times 2 mL of water and three times 2 mL of 20% ethanol/0.01 M phosphate buffer. The column was then-dried in vacuo and eluted with two times 1.0 mL acetonitrile. About 75% of the $^{188}$Re-radioactivity was recovered in greater than 95% purity as the ester chelate compound. The organic solvent was then evaporated under a flow of inert gas.

The chelate was then conjugated to a Fab fragment of a monoclonal antibody specific for the above described 250 Kd antigen on melanoma cells. This monoclonal antibody has been designated NR-ML-05 and is specific for a different epitope on the 250 Kd antigen than the 9.2.27 antibody described previously.

A buffered solution of the antibody fragment (5 mg/mL, 0.5 mL) was added to the purified 188Re-labeled chelate, followed by 0.5 mL of 0.5 M carbonate/bicarbonate buffer pH 9.50. The reaction was kept at room temperature for 15 minutes, then 25 mg of L-lysine, 0.1 mL, was added and the reaction was pursued at room temperature for 15 minutes more.

A column containing Sephadex G-25 material was used to purify the $^{188}$Re conjugate. The reaction mixture was loaded on top of the column, and 1.2 mL aliquots were collected using PBS buffer to rinse the reaction vial and elute the $^{188}$Re conjugate in the third and fourth fractions. The purity of the $^{188}$Re conjugate was usually greater than 97% for about 35 conjugation yields. The conjugate was then further diluted with PBS, and radioactivity was measured prior to injection into the test animals.

In an alternative procedure for preparing the rhenium chelate, the $^{188}$Re (in the form of $ReO_4-$ perrhenate) was concentrated on a reversed phase cartridge as the tetrabutylammonium (TBA) ion pair according to the procedure described in copending U.S. patent application Ser. No. 802,779. The total perrhenate elution of the generator (about 15 mL, in saline) was loaded on the cartridge, which was first conditioned with 2 mL of 0.01 M TBA. The cartridge was washed with water and 2.5% $CH_3CN$, dried under vacuum, and greater than 98% of the perrhenate was eluted with 1 mL $CH_3CN$, which was dried under a flow of nitrogen. This allowed concentration of virtually all the activity under conditions that did not affect the yields of $^{188}$Re-labeled $N_2S_2$ active ester chelates, as presented below. In this alternative embodiment, a kit comprises 25 mg of citric acid, 0.25 mg of stannous chloride, 0.25 mg of gentisic acid and 100 mg of lactose all in a single vial in lyophilized form. This lyophilized preparation was reconstituted with 1.0 ml of water, and 0.5 mL of this solution was added to the dried perrhenate and, after 10 minutes at room temperature, 0.1 mL of a 1.0 mg/mL Ethoxyethyl-$N_2S_2$-TFP ligand in isopropyl alcohol was added. This is the same chelating compound used in Example 15. The reaction was heated at 75o C for 10 minutes, producing $^{188}$Re $N_2S_2$-TFP esters in greater than 90% yields. Conjugation of the chelate to a protein is accomplished as described above.

Example 17

Imaging of Tumors in Humans.

Antibody fragments radiolabeled with $^{99m}$Tc according to the method of the invention were injected into human patients to detect melanoma sites within the body. The antibody fragments used were F(ab')$_2$, Fab' or Fab fragments of one of two monoclonal antibodies specific for the 250 Kd glycoprotein/proteoglycan antigen of melanoma cells, as shown in Table 4. The fragments were generated by standard techniques (i.e., pepsin treatment of the monoclonal antibody to generate the F(ab')$_2$ fragment, papain treatment of the monoclonal antibody to generate the Fab fragment, and treatment with a reducing agent such as dithiothreitol to generate the Fab' fragment). The two monoclonal antibodies designated 9.2.27 and NR-ML-05 are both directed against the 250 Kd of melanoma cells, as described above, but are specific for different epitopes of the antigen.

The chelate compound having the formula

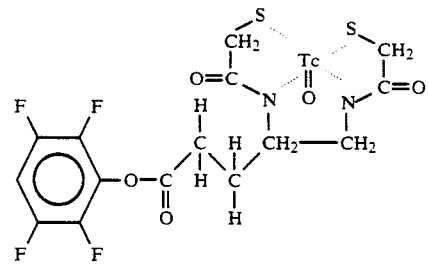

was prepared by one of the methods described herein. For patient number 8501.350, the chelate was prepared and conjugated to the antibody fragment according to the procedures outlined in Examples 13 and 15. For the other four patients, the chelate was prepared and conjugated generally as described in Example 7. The resulting radiolabeled antibody fragments were purified, and a quality control test was performed, as described in Example 15. Approximately 40 minutes to 1 hour and 30' prior to infusion of the radiolabeled antibody, each patient received 41 to 50 mg of an irrelevant antibody in 12 to 20 mLs of sterile saline by intravenous infusion. In addition, each patient received 7.5 mg of a non-radiolabeled specific antibody in 20 mLs of sterile saline by intravenous infusion either simultaneously with, or approximately 5 minutes prior to infusion of the radiolabeled specific antibody. The non-radiolabeled specific antibody was either a whole monoclonal antibody specific for the 250 Kd antigen on melanoma cells (NR-ML-05 for patient number 8501.350 and 9.2.27 for the other patients) or a F(ab')$_2$ fragment of such an antibody. The irrelevant antibody was a monoclonal antibody designated NR2AD, which is a murine IgG$_{2a}$ immunoglobulin that was designed as an anti-idiotype that bound to a single patient's B-cell lymphoma and to no other human tissue.

Into each patient was injected 20 to 30 mLs of sterile saline comprising the radiolabeled antibody fragment, by intravenous infusion. The patients received from 11.4 mCi to about 30 mCi of $^{99m}$Tc radioisotope. The desired upper limit of radioisotope administered is 30 mCi, and the minimum for effective imaging of tumors is generally about 10 mCi. The total amount of protein in the administered solutions ranged from 2.5 mgs to 10 mgs. Imaging by gamma camera was performed at four timepoints: immediately following infusion of the radiolabeled antibody, at about 3 hours post infusion, at from to 8 hours post infusion, and at from 19 to 20 hours post infusion. The best images of the target sites (tumors) were achieved by imaging at from 7 to 8 hours after completion of infusion of the radiolabeled antibody. At the two earlier timepoints, much of the radioactivity was still in the patient's blood; and the amount of radioactivity which had localized in target sites was generally insufficient for good visualization of tumors. Imaging at the 19 to 20 hour time-point (attempted in only 2 of the patients) produced images which generally were fainter and therefore inferior to those of the 7 or 8 hour timepoint due to decay of the $^{99m}$Tc radio-isotope, which has a halflife of about 6 hours. Melanoma sites, including metastases, were detected in each patient. Although some accumulation of radioactivity in the kidneys was detected during these imaging procedures, the kidneys generally are not considered to be target sites in the diagnostic procedures of the invention. In addition, tissue samples were removed from each patient for biopsy at the timepoints indicated in TABLE 4. The various biopsy samples were analyzed in a gamma counter to measure the radioactivity, in terms of counts per minute (cpm), in each biopsy sample. The samples were weighed, and the total cpm in each sample was divided by the number of mg in the sample to give the cpm per mg of tissue. The percentage of the total injected dose of radioactivity (in cpm) which had localized in each of the various tissue types sampled was calculated and is shown in Table 4. The ratio of the radioactivity found in tumor site(s) to the radioactivity found in the other types of tissue also was calculated. The value in the "percent injected dose per mg" column for the tumor tissue in a particular patient was divided by the value in the "percent injected dose per mg" column for each non-tumor tissue sample extracted from the patient to give the tumor:tissue ratio for each non-tumor tissue sample. The results are presented in TABLE 4.

TABLE 4

Tumor Localization of Tc-99m Antimelanoma Antibody

| Treatment Group | Patient No. | Tissue | Time Point (hrs) | % Injected Dose (per mg) | Tumor: Tissue Ratio | Antibody |
|---|---|---|---|---|---|---|
| 5 | 8501.080 | Fat | 23.0 | .0007 | 47.1 | (Fab')$_2$ of 9.2.27 |
| 5 | 8501.080 | Fat and Connective Tissue | 23.0 | .0082 | 4.0 | |
| 5 | 8501.080 | S.C. Tumor | 23.0 | .0330 | | |
| 5 | 8501.080 | Serum | 23.0 | .0151 | 2.1 | |
| 5 | 8501.080 | Skin | 23.0 | .0025 | 13.2 | |
| 5 | 8501.100 | Adjacent Fat | 27.0 | .0028 | 5.6 | (Fab')$_2$ of 9.2.27 |
| 5 | 8501.100 | Fat | 27.0 | .0010 | 15.9 | |
| 5 | 8501.100 | S.C. Tumor | 27.0 | .0159 | | |
| 5 | 8501.100 | Serum | 27.0 | .0118 | 1.3 | |
| 5 | 8501.100 | Skin | 27.0 | .0100 | 1.6 | |
| 6 | 8501.140 | Fat | 22.0 | .0001 | 43.0 | Fab' of 9.2.27 |
| 6 | 8501.140 | Serum | 22.0 | .0010 | 4.3 | |
| 6 | 8501.140 | Skin | 22.0 | .0004 | 11.8 | |
| 6 | 8501.140 | Tissue | 22.0 | .0005 | 8.6 | |
| 6 | 8501.140 | Tumor | 22.0 | .0043 | | |
| 8 | 8501.250 | Serum | 19.0 | .0007 | 5.6 | Fab of 9.2.27 |
| 8 | 8501.250 | Tumor | 23.0 | .0039 | | |
| 9 | 8501.350 | Serum | 23.5 | .0012 | 3.3 | Fab of NR-ML-05 |
| 9 | 8501.350 | Skin | 23.5 | .0010 | 3.9 | |
| 9 | 8501.350 | Tumor | 23.5 | .0039 | | |

Example 18

Preparation of a Chelate Compound Comprising a Thiophenyl Ester Group and Having the Formula:

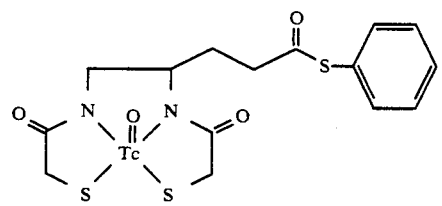

Sodium pertechnetate (0.5 mL was added to a freshly prepared stannous gluconate solution in a vial (0.1 mL containing 5.0 mg gluconic acid and 120 mg stannous chloride) at pH 6.1 to 6.3. The reactants were incubated at room temperature for 10 minutes. To the $^{99m}$Tc-gluconate exchange complex formed in the vial was added 0.1 mL of a $C_5N_2S_2$ chelating compound comprising ethoxyethyl S-protecting groups and a thiophenyl active ether group, designated "ethoxyethyl $C_5N_2S_2$-thiophenylate" (1.0 mg dissolved in a mixture of isopropanol and glacial acetic acid in 9:1 ratio), 55 mL of 0.2 N hydrochloric acid, followed by 0.2 mL of additional isopropanol. The vial contents were heated at 75° C. for 15 minutes to give 80% by HPLC of the technetium-labeled $C_5N_2S_2$-thiophenylate chelate. The solvent system used for HPLC elution of the thiophenylate epimers is 34% acetonitrile, 0.01 M sodium phosphate pH 6. The precipitate observed with 1.0 mg of ligand was rectified by using 20 ug instead. The reactivity of $^{99m}$Tc-$C_5N_2S_2$-thiophenylate was checked by its reaction with lysine as well as with a Fab antibody fragment. To 0.2 mL of L-lysine (100 mg dissolved in 1.0 mL of 0.5 M phosphate buffer pH 10.5) was added 0.1 mL of $^{99m}$Tc-C$_5$N$_2$S$_2$-thiophenylate, which was then incubated at room temperature. The disappearance of all the Tc-C$_5$N$_2$S$_2$-thiophenylate was observed in less than 15 minutes as indicated by HPLC (34% CH$_3$CN, 0.01 M NaPi, pH 6) and by ITLC in both acetonitrile and 12% TCA. Conjugation of the Tc-C$_5$N$_2$S$_2$-thiophenylate with a Fab fragment of monoclonal antibody 9.2.27 (described above) was carried out at 1.1 mg/mL using 1.0 M phosphate buffer with three different pH values, as shown in the following Table 5.

TABLE 5

| | Antibody Conjugation Reactions | |
|---|---|---|
| Reaction No. | pH of Solution during Conjugation | % Tc-labeled Ab HPLC |
| 1 | 6.0 | 24 |
| 2 | 7.0 | 25 |
| 3 | 8.0 | 40 |

Example 19

Biodistribution Studies in Mice for $^{99m}$Tc-labeled Monoclonal Antibody Fragment.

Figure 3A:
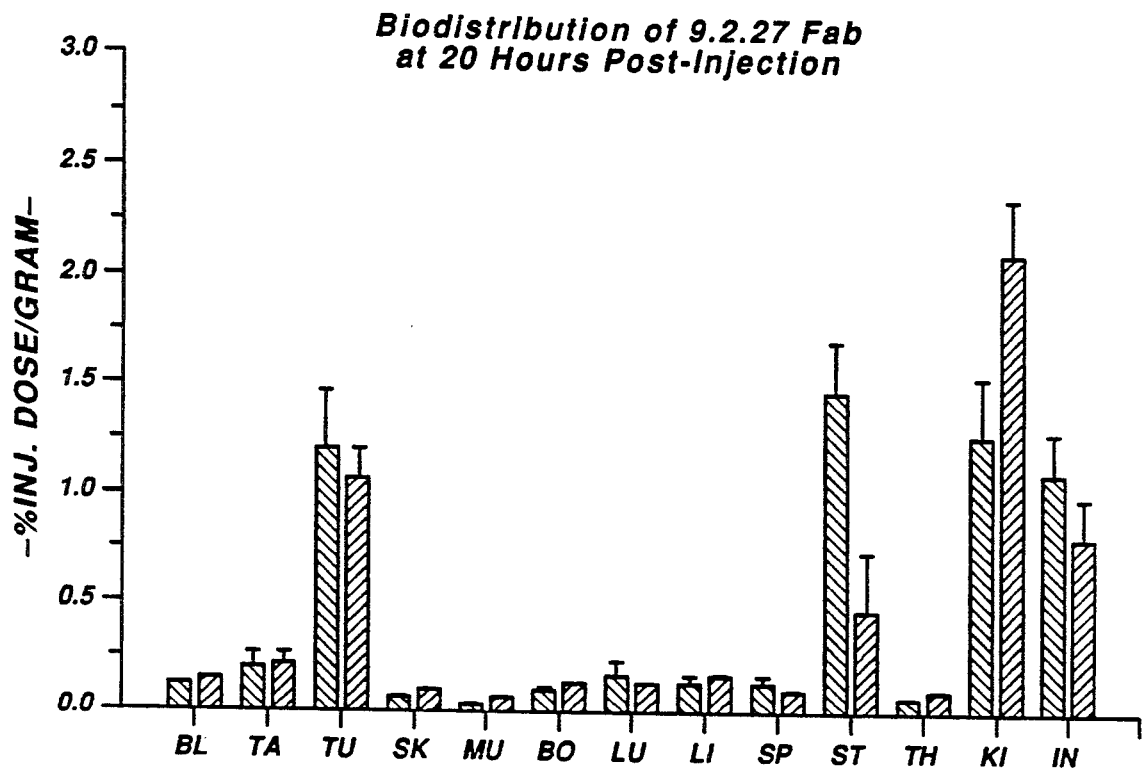
FIGS. 3 (a-b), 4, 5 (a-b), and 6 (a-b) show biodistribution data for various antibody fragments radiolabeled with $^{99m}$Tc or $^{188}$Re in accordance with the invention, and injected into tumor-bearing mice. The antibody fragments are specific for various types of cancer cells.
Figure 3B:
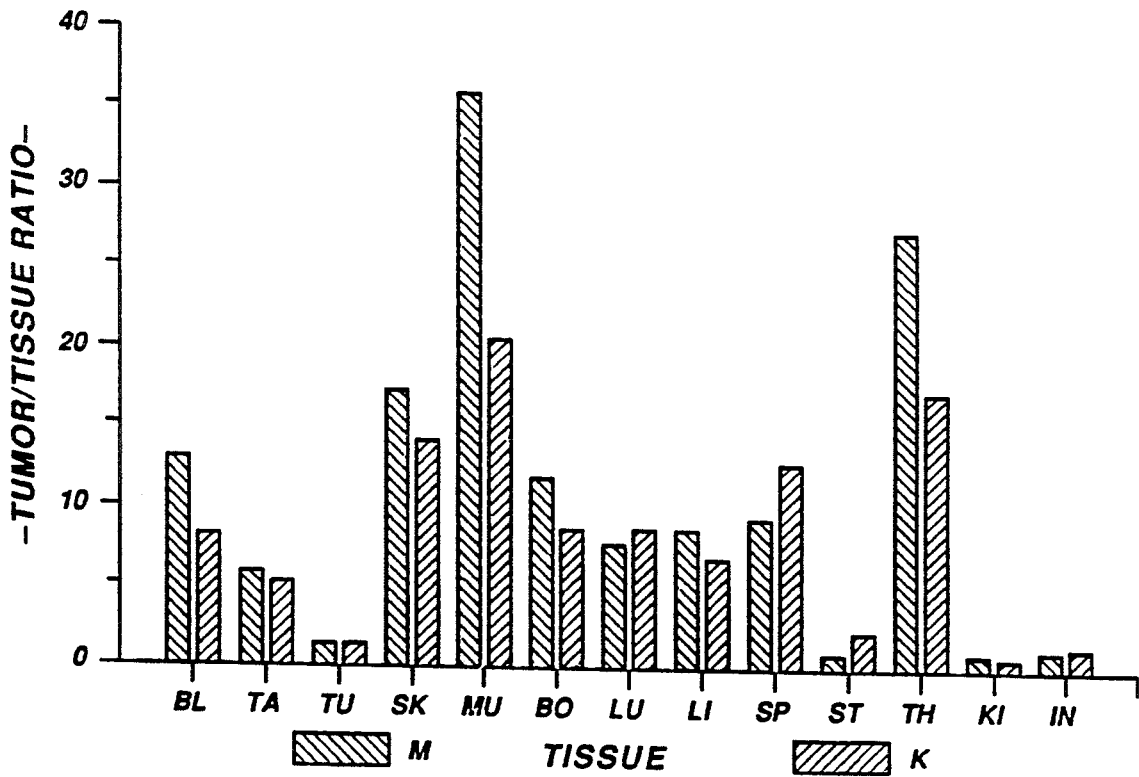

Antibody fragments radiolabeled with $^{99m}$Tc were injected into mice, and biodistribution of the radionuclide protein conjugate was analyzed 20 hours after injection according to the method of Hwang, et al., *Cancer Res.*, 45:4150–4155 (1985). The antibody fragment was a Fab fragment of the above-described monoclonal antibody designed 9.2.27, specific for the 250 Kd antigen of melanoma cells. The results are shown in FIG. 3. The set of data labeled "M" represents data for a protein conjugate prepared, generally as described in Example 7. The set of data labeled "K" represents data for a protein conjugate prepared using the "kit approach" as described in Examples 13 and 15. The data are presented in terms of the percentage of the injected radioactivity per gram of each specified tissue type (FIG. 3A) and the tumor/tissue ratio of injected radioactivity (FIG. 3B). The tissue types represented are as follows: BL=blood; TA=tail; TU=tumor; SK=skin; MU=muscle; BO=bone; LU=lung; LI=liver; SP=spleen; ST=stomach; TH=thyroid; KI=kidney; and IN=intestine. Melanoma sites (tumors) were effectively identified in each of the mice studied. The data represent the average for four mice in each of the two groups ("M" and "K").

Example 20

Biodistribution Studies for $^{188}$Re-labeled Monoclonal Antibody Fragment.

Figure 4:
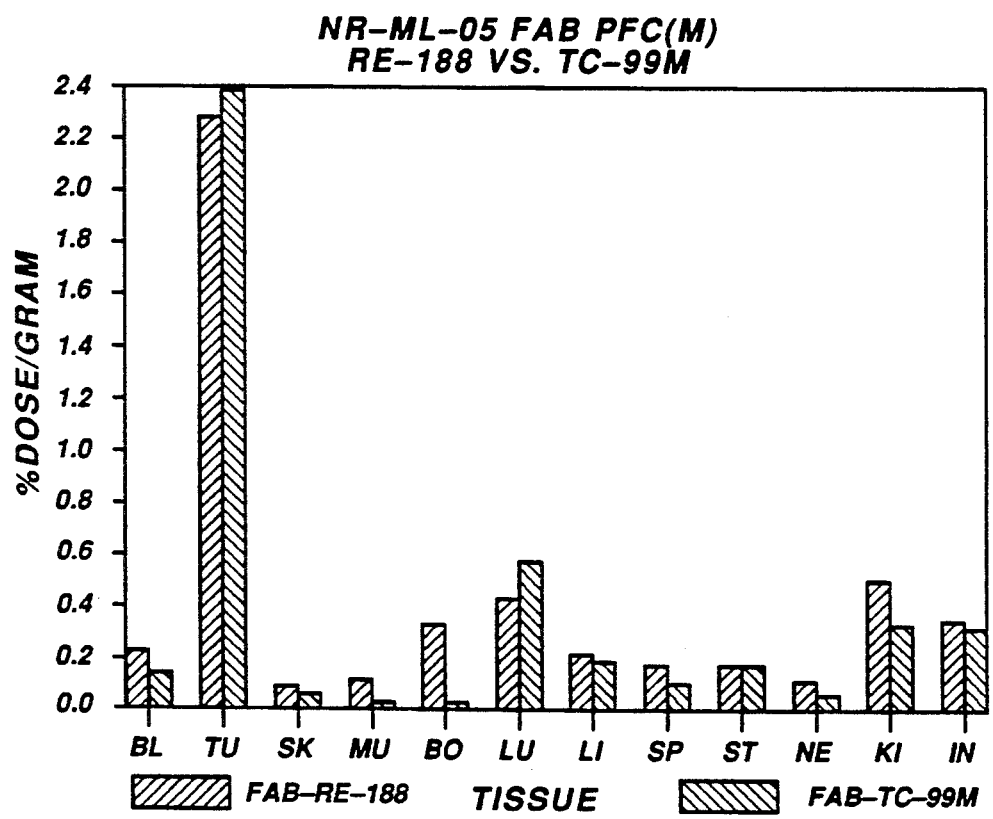

A chelate compound having the formula:

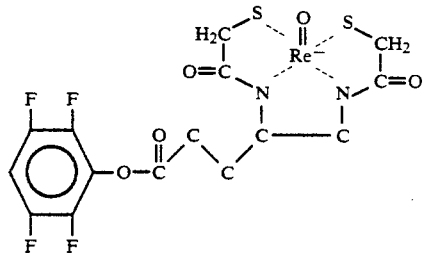

in which the radionuclide metal is $^{188}$Rhenium, was prepared as described in Example 8. The chelate was conjugated to a Fab fragment of a monoclonal antibody specific for the 250 Kd glycoprotein/proteoglycan melanoma associated antigen. The monoclonal antibody is designated NR-ML-05, and the Fab fragment was produced by treatment of the monoclonal antibody with papain according to conventional techniques. The conjugation step and purification of the resulting radiolabeled polypeptide were as described in Example 8. The chelate-polypeptide conjugate was injected into tumor-bearing mice, and biodistribution of the radiolabeled material was analyzed 20 hours after injection according to the method of Hwang, et al., *Cancer Res.* 45:4150–4155 (1985). The results are presented in FIG. 4 in which the percentage of the injected dose of radionuclide present in each of the specified types of tissue (per gram of tissue) is shown, including tumor tissue. The same chelating compound was radiolabeled with $^{99m}$Tc and conjugated to the same Fab fragment as described above) and injected into mice. Biodistribution was detected by the same method used for the $^{188}$Re-labeled conjugate, to provide the comparative data presented in FIG. 4. The tissues analyzed are as follows: BL=blood, TU=tumor, SK=skin, MU=muscle, BO=bone, LU=lung, LI=liver, SP=spleen, ST=stomach, NE=neck (thyroid), KI=kidney, and IN=intestine.

Example 21

Biodistribution studies in mice for various antibody fragments radiolabeled with $^{99m}$Tc.

$^{99m}$Tc-labeled C$_5$N$_2$S$_2$ chelate compounds were conjugated to various antibody fragments in accordance with the invention. The resulting chelate-antibody conjugates were injected into nude mice bearing tumors, and biodistribution of the injected radioactivity was analyzed according to the method of Hwang, et al., Supra.

Figure 5A:
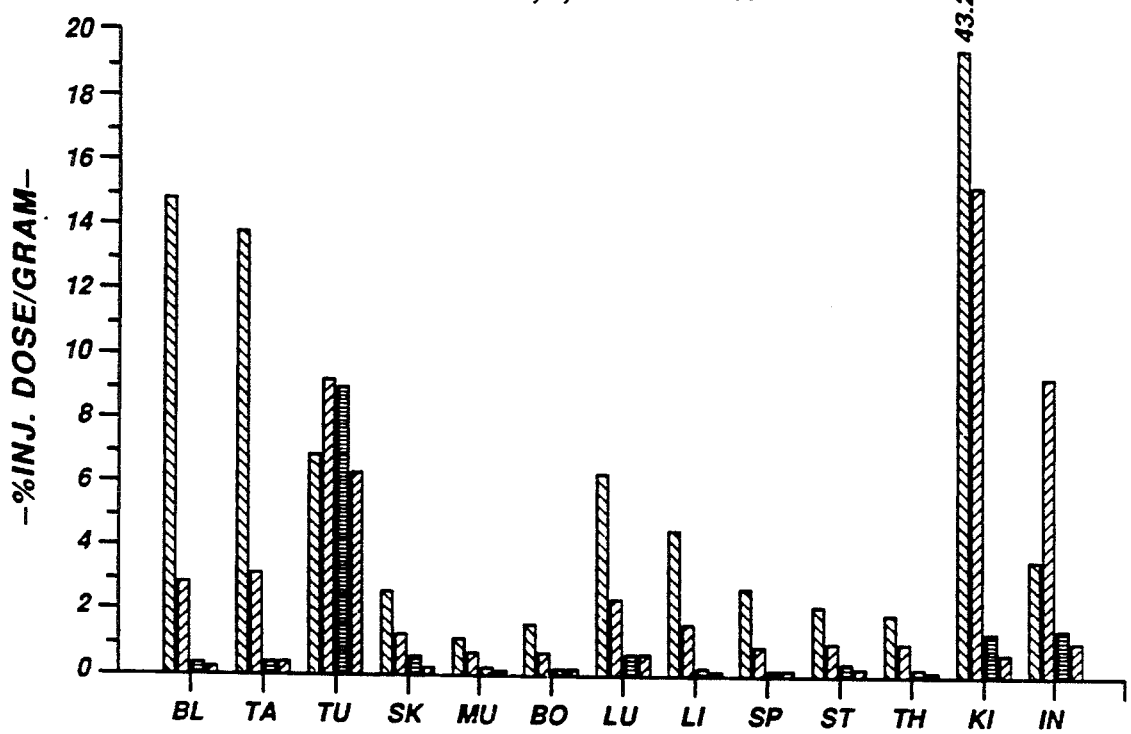
Figure 5B:
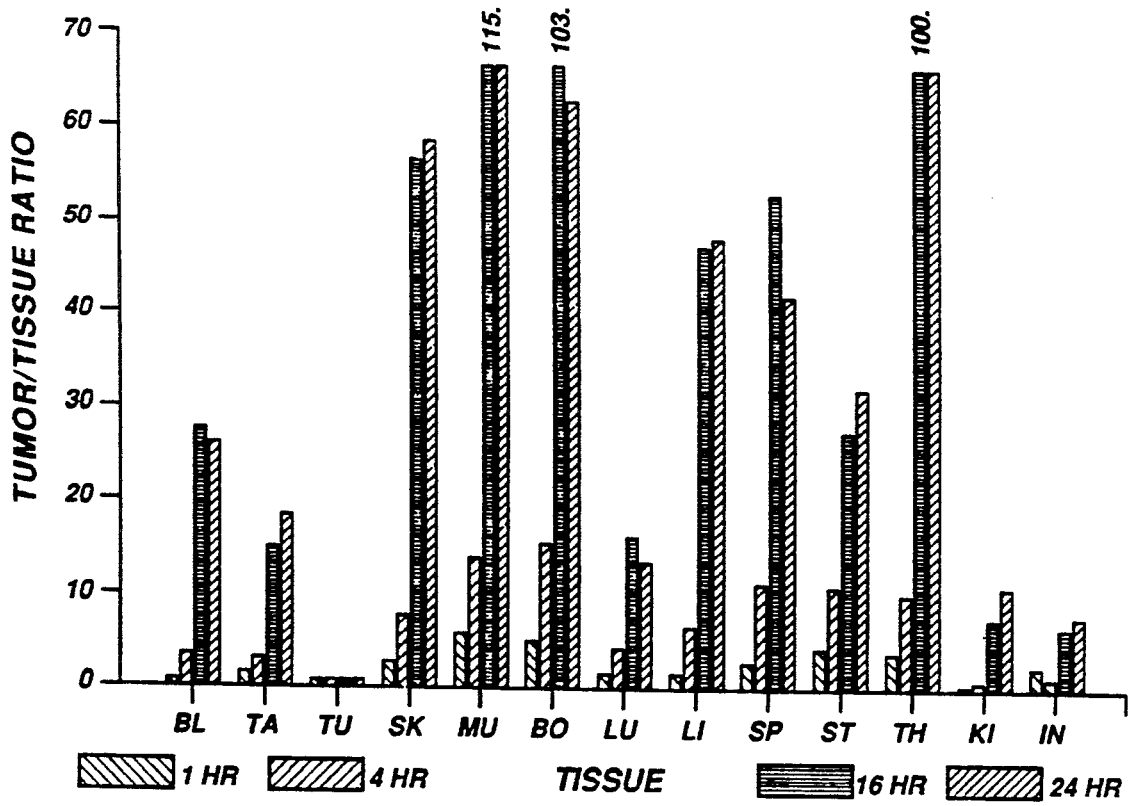

FIG. 5 shows biodistribution data for a $^{99m}$Tc-labeled chelate-antibody conjugate injected into nude mice bearing colon carcinoma xenografts (tumors). The antibody was a Fab fragment of a monoclonal antibody designated NR-CE-01, which is specific for an epitope of carcinoembryonic antigen, an antigen specific for various types of cancer cells, including colon carcinoma. Approximately 10 ug (100 uCi) of the conjugate was injected into each mouse, and biodistribution was analyzed at four timepoints: 1, 4, 16, and 24 hours post injection. FIG. 5A shows the percentage of the injected radioactivity localized in each of the specified types of tissue, including tumor tissue, per gram of tissue at each timepoint. Relative clearance of the radioisotope from non-tumor tissue is demonstrated over time. The abbreviations for the tissue types are as in Example 19. FIG. 5B shows the tumor:tissue ratio of injected radioactivity for each of the specified tissue types. The biodistribution data were calculated as described in Example 17, with the data being the average for four mice sacrificed at each timepoint.

FIGS. 6A and 6B show biodistribution data for two $^{99m}$Tc-C$_5$N$_2$S$_2$ chelate antibody conjugates injected into nude mice bearing colon carcinoma xenografts (tumors). One of the conjugates comprised a Fab fragment of an antibody designated NR-LU-10, specific for a 40 kd glycoprotein associated with various types of adenocarcinoma cells of different histologic origin. The other conjugate comprised a Fab' fragment of an antibody designed L11, specific for carcinoembryonic antigen (but for a different epitope of the antigen than the above-described NR-CE-01 antibody.) Each mouse received 50 ug (about 100 uCi) of one of the conjugates. The mice were sacrificed 20 hours post injection, and biodistribution data were calculated as described above.

Although the foregoing invention has been described in some detail by way of illustration and example for purposes of clarity of understanding, it will be obvious that certain changes and modifications may be practiced with the scope of the appended claims.

WHAT IS CLAIMED:
1. A method for preparing a radiolabeled polypeptide, comprising the steps of:
    a) reacting a metal radionuclide with a reducing agent and a complexing agent to form an exchange complex comprising said radionuclide;
    b) reacting said exchange complex with a chelating compound of the following formula:

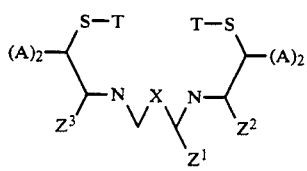

wherein:
    one of $Z^1$, $Z^2$, $Z^3$ or $Z^4$ is RCW(HNRCW)$_n$Y, [RCW(HNV)$_n$Y,] and the others are H$_2$ or =O;
    each R is independently selected from divalent organic radicals of from 1 to 6 carbon atoms and 0 to 2 heteroatoms;
    each W is independently selected from =NH or =O, with the proviso that the W bonded to the carbon atom bonded to Y is H$_2$ when Y is —NH$_2$ or NHNH$_2$;
    n is 0 or 1;
    T is a removable sulfur protective group;
    Y is the leaving group of an active ester, wherein said ester will react with a polypeptide in an aqueous medium to form an amide or amidine bond with said polypeptide; or —NH$_2$; or —NHNH$_2$;
    X is a bond, methylene, or CHZ$^4$; and
    the A's are the same or different and are hydrogen or lower alkyl of from 1 to 6 carbon atoms; whereby said metal radionuclide becomes chelated by said compound to form a corresponding chelate compound; and
    c) reacting said chelate compound with a polypeptide to form a covalent bond between said chelate compound and said polypeptide, thereby forming said radiolabeled polypeptide with the proviso that when Y is —NH$_2$ or —NHNH$_2$, said polypeptide has an oxo group as a result of glycol cleavage of a sugar bound to said polypeptide, and said combining is under reductive amination conditions.

2. The method according to claim 1 wherein said polypeptide is an immunoglobulin or specific binding fragment thereof.

3. The method according to claim 2 wherein said immunoglobulin is a monoclonal antibody.

4. The method according to claim 3 wherein said monoclonal antibody is specific for cancer cells.

5. The method according to claim 4 wherein said cancer cells are melanoma cells.

6. The method according to claim 2 wherein said specific binding fragment is selected from the group consisting of a F(ab), F(ab'), F(ab')$_2$, and F$_v$ fragment of an antibody.

7. The method according to claim 6 wherein said fragment is specific for cancer cells.

8. The method according to claim 7 wherein said cancer cells are melanoma cells.

9. The method according to claim 1 wherein said metal radionuclide is $^{99m}$Tc; said reducing agent is selected from the group consisting of stannous salts, metallic tin, formamidine sulfuric acid, ferric chloride, ferrous sulfate, ferrous ascorbate, and alkali salts of borohydride; and said complexing agent is gluconic acid.

10. The method according to claim 9, wherein said reducing agent is stannous chloride.

11. The method according to claim 1 wherein said metal radionuclide is a rhenium isotope; said reducing agent is selected from a stannous salt, metallic tin, formamidine sulfuric acid, ferric chloride, ferrous sulfate, ferrous ascorbate, and alkali salts of borohydride; and said complexing agent is citric acid.

12. The method according to claim 11 wherein said reducing agent is a stannous salt.

13. The method according to claim 1, wherein X is a bond.

14. The method according to claim 1, wherein Y is the leaving group of an active ester, wherein said ester will react with said polypeptide in an aqueous medium to form an amide bond.

15. The method according to claim 14, wherein said ester is selected from a 2,3,5,6-tetrafluorophenyl ester and a thiophenyl ester.

16. The method according to claim 1, wherein X is a bond, Z$_3$ is =O, and one of Z$_1$ or Z$_2$ is

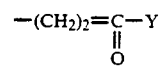

and the other is =O or H$_2$.

17. The method according to claim 1, wherein the two Ts are taken together to represent a sulfur protective group which, together with sulfur atoms to be protected, defines a thioacetal group represented by the formula:

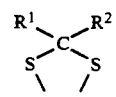

wherein R$^1$ and R$^2$ are the same or different and are selected from the group consisting of hydrogen; lower alkyl groups; and an aromatic ring having an electron donating group bonded directly to said aromatic ring.

18. The method according to claim 1, wherein each T, when taken together with the sulfur group to be protected, defines a hemithioacetal sulfur protective group of the formula:

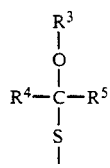

wherein R³ and R⁴ each represent a lower alkyl group, and R⁵ represents hydrogen or a lower alkyl group.

19. The method according to claim 1, wherein each T, when taken together with the sulfur group to be protected, defines a hemithioacetal sulfur protective group of the formula:

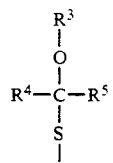

wherein R³ and R⁴ are taken together with the carbon atom and the oxygen atom shown in said formula to define a nonaromatic ring, and R⁵ represents hydrogen or a lower alkyl group.

20. The method according to claim 1, wherein said radionuclide is selected from the group consisting of $^{99m}Tc$, $^{188}Re$, $^{186}Re$, $^{67}Cu$, $^{64}Cu$, $^{212}Pb$, $^{212}Bi$, and $^{109}Pd$.

* * * * *

UNITED STATES PATENT AND TRADEMARK OFFICE
CERTIFICATE OF CORRECTION

PATENT NO.   :  5,120,526

DATED        :  June 9, 1992

INVENTOR(S)  :  Fritzberg et al.

It is certified that error appears in the above-identified patent and that said Letters Patent is hereby corrected as shown below:

In column 55, line 28 [claim 1], please delete [RCW(HNV)$_n$Y,]

In column 56, line 40 [claim 16], please insert a space between "Z$_3$" and "is"

In column 56, lines 40-45 [claim 16] that portion of the formula reading $$=\underset{\underset{O}{\|}}{C}-Y \quad \text{should read} \quad -\underset{\underset{O}{\|}}{C}-Y$$

Signed and Sealed this

Fourteenth Day of November, 1995

*Attest:*

BRUCE LEHMAN

*Attesting Officer*       *Commissioner of Patents and Trademarks*